United States Patent
Zembower et al.

(10) Patent No.: US 7,648,978 B2
(45) Date of Patent: Jan. 19, 2010

(54) SMALL MOLECULE MODULATORS OF CYTOKINE ACTIVITY

(75) Inventors: David E. Zembower, La Grange, IL (US); Jasbir Singh, Naperville, IL (US); Rama K. Mishra, Chicago, IL (US)

(73) Assignee: Angion Biomedica Corp., Great Neck, NY (US)

( * ) Notice: Subject to any disclaimer, the term of this patent is extended or adjusted under 35 U.S.C. 154(b) by 527 days.

(21) Appl. No.: 11/238,285

(22) Filed: Sep. 28, 2005

(65) Prior Publication Data

US 2006/0116365 A1 Jun. 1, 2006

Related U.S. Application Data

(60) Provisional application No. 60/675,241, filed on Apr. 27, 2005, provisional application No. 60/613,740, filed on Sep. 28, 2004.

(51) Int. Cl.
*A61P 25/00* (2006.01)
*A61K 31/55* (2006.01)
*C07D 403/02* (2006.01)
(52) U.S. Cl. .................. 514/217.05; 540/599
(58) Field of Classification Search ............ 514/217.05; 540/599
See application file for complete search history.

(56) References Cited

U.S. PATENT DOCUMENTS

| | | | |
|---|---|---|---|
| 4,806,535 A | 2/1989 | Faith et al. | |
| 5,997,868 A * | 12/1999 | Goldberg et al. | ......... 424/158.1 |
| 6,011,009 A * | 1/2000 | Goldberg et al. | ............... 514/8 |
| 6,635,642 B1 | 10/2003 | Jackson et al. | |
| 2003/0073692 A1 | 4/2003 | Pulici et al. | |

FOREIGN PATENT DOCUMENTS

WO WO2006036981 4/2006

OTHER PUBLICATIONS

International Search Report for PCT/US2005/34669 mailed Jul. 27, 2006, 7 pages.
Written Opinion of the ISA for PCT/US2005/34669 mailed Mar. 28, 2007, 11 pages.
Bold, G. et al. "CGP 79787D (PTK787/ZK222584), CGP 84738, NVP-AAC789, NVP-AAD777 and Related 1-anilino-(4-pyridylmethyl)phthalazines as Inhibitors of VEGF- and BFGF-Induced Angiogenesis" Drugs of the Future, Barcelona, ES, vol. 27, No. 1, 2002, pp. 43-55, XP008018115.
Oe et al., J. Hepatol. 2001, 34(6), 832-839.
Tsuzuki et al., Acta Neurochir. Suppl. 2000, 76, 311-316.
Jin et al., J. Pharmacol. Exp. Ther. 2003, 304(2), 654-660.
Franquesa et al., Gene Ther. 2005, 12(21), 1551-1558.
Dohi et al., Am. J. Respir. Crit. Care Med. 2000, 162(6), 2302-2307.
Watanabe et al., Mol. Ther. 2005, 12(1), 58-67.
Matsuno et al., Gene Ther. 2003, 10(18), 1559-1566.
Tashiro et al., Transplantation 2003, 76(5), 761-765.
Lopez-Talavera et al., Endocrinology 2004, 145(2), 467-474.
Nakamura et al., J. Clin. Invest. 2000, 106(12), 1511-1519.
Zhou et al., Biochem. Biophys. Res. Commun. 2006, 344(2), 658-666.
Nakagami et al., Diabetes 2002, 51(8), 2604-2611.
Numata et al., Inflamm. Bowel Dis. 2005, 11(6), 551-558.
Yoshida et al., Growth Factors 2004, 22(2), 111-119.
Ono et al., J. Surg. Res. 2004, 120(1), 47-55.
Shimamura et al., Circulation 2004, 109(3), 424-431.
Powell et al., Vasc. Med. 2004, 9(3), 193-198.
Morishita et al., Hypertension 2004, 44(2), 203-209.
Morishita et al., Curr. Gene Ther. 2004, 4(2), 199-206.
Hwang et al., Life Sci. 2003, 72(7), 851-861.
Fujimoto et al., J. Gastroenterol. Hepatol. 2000, suppl. D33-36.
Ueki et al., Nat. Med. 1999, 5(2), 226-230.
Chi et al., World J. Gastroenterol. 2005, 11(10), 1496-1502.
Yang et al., Am. J. Physiol. Renal Physiol. 2003, 284(2), F349-357.
Herrero-Fresnada et al., Kidney Int. 2006, 70(2), 265-274.
Examiner Search Report dated May 6, 2008 and cited in Office Action mailed May 14, 2008.
Demirayak et al., "Some Pyrrole Substituted Aryl Pyridazinone and Phthalazinone Derivatives and Their Antihypertensive Activities" *European Journal of Medicinal Chemistry*, 39(2004) 1089-1095.

* cited by examiner

*Primary Examiner*—Brenda L Coleman
(74) *Attorney, Agent, or Firm*—Choate, Hall & Stewart LLP

(57) ABSTRACT

The present invention provides compounds having formula (I) or (II):

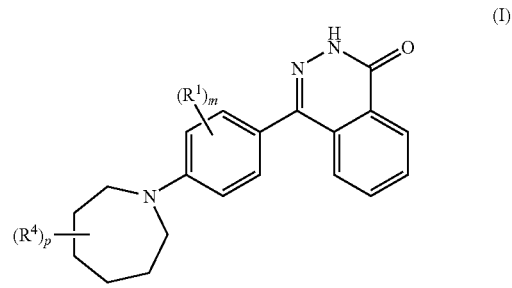

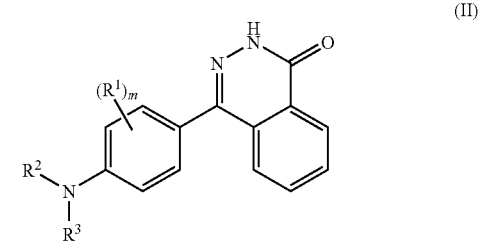

and pharmaceutically acceptable derivatives thereof, wherein m, p, $R^1$, $R^2$, $R^3$ and $R^4$ are as described generally and in classes and subclasses herein, and additionally provides pharmaceutical compositions thereof, and methods for the use thereof for the treatment of any of a number of diseases, disorders or conditions associated with HGF/SF or other cytokine activity.

32 Claims, 12 Drawing Sheets

A

B

C

D

A

B

C

A

B

C

D

SMALL MOLECULE MODULATORS OF CYTOKINE ACTIVITY

PRIORITY

This application claims priority to provisional applications Ser. No. 60/613,740, filed Sep. 28, 2004, and Ser. No. 60/675,241, filed Apr. 27, 2005, both of which are incorporated by reference herein in their entireties.

GOVERNMENT SUPPORT

This work was supported in part by the U.S. Government, grant IR43CA096077 from the Public Health Service, National Institutes of Health. The U.S. Government may have certain rights in this invention.

BACKGROUND OF THE INVENTION

Scatter factor (SF; also known as hepatocyte growth factor [HGF], and hereinafter referred to and abbreviated as HGF/SF) is a pleiotropic growth factor that stimulates cell growth, cell motility, morphogenesis and angiogenesis. HGF/SF is produced as an inactive monomer (~100 kDa) which is proteolytically converted to its active form. Active HGF/SF is a heparin binding heterodimeric protein composed of a 62 kDa α chain and a 34 kDa β chain. HGF/SF is a potent mitogen for parenchymal liver, epithelial and endothelial cells (Matsumoto, K, and Nakamura, T., 1997, Hepatocyte growth factor (HGF) as a tissue organizer for organogenesis and regeneration. Biochem. Biophys. Res. Commun. 239, 639-44; Boros, P. and Miller, C. M., 1995, Hepatocyte growth factor: a multifunctional cytokine. Lancet 345, 293-5). It stimulates the growth of endothelial cells and also acts as a survival factor against endothelial cell death (Morishita, R, Nakamura, S, Nakamura, Y, Aoki, M, Moriguchi, A, Kida, I, Yo, Y, Matsumoto, K, Nakamura, T, Higaki, J, Ogihara, T, 1997, Potential role of an endothelium-specific growth factor, hepatocyte growth factor, on endothelial damage in diabetes. Diabetes 46:138-42). HGF/SF synthesized and secreted by vascular smooth muscle cells stimulates endothelial cells to proliferate, migrate and differentiate into capillary like tubes in vitro (Grant, D. S, Kleinman, H. K., Goldberg, I. D., Bhargava, M. M., Nickoloff, B. J., Kinsella, J. L., Polverini, P., Rosen, E. M., 1993, Scatter factor induces blood vessel formation in vivo. Proc. Natl. Acad. Sci. USA 90:1937-41; Morishita, R., Nakamura, S., Hayashi, S., Taniyama, Y., Moriguchi, A., Nagano, T., Taiji, M., Noguchi, H., Takeshita, S., Matsumoto, K., Nakamura, T., Higaki, J., Ogihara, T., 1999, Therapeutic angiogenesis induced by human recombinant hepatocyte growth factor in rabbit hind limb ischemia model as cytokine supplement therapy. Hypertension 33:1379-84). HGF/SF containing implants in mouse subcutaneous tissue and rat cornea induce growth of new blood vessels from surrounding tissue. HGF/SF protein is expressed at sites of neovascularization including in tumors (Jeffers, M., Rong, S., Woude, G. F., 1996, Hepatocyte growth factor/scatter factor-Met signaling in tumorigenicity and invasion/metastasis. J. Mol. Med. 74:505-13; Moriyama, T., Kataoka, H., Koono, M., Wakisaka, S., 1999, Expression of hepatocyte growth factor/scatter factor and its receptor c-met in brain tumors: evidence for a role in progression of astrocytic tumors Int. J. Mol. Med. 3:531-6). These findings suggest that HGF/SF plays a significant role in the formation and repair of blood vessels under physiologic and pathologic conditions. Further discussion of angiogenic proteins may be found in U.S. Pat. Nos. 6,011,009 and 5,997,868, both of which are incorporated herein by reference in their entireties.

In certain embodiments, the present invention is directed toward the identification of small organic molecules that exhibit HGF/SF activity and are thus useful in the treatment or prevention of conditions or diseases in which HGF/SF activity is desirable.

All citations in the present application are incorporated herein by reference in their entireties. The citation of any reference herein should not be construed as an admission that such reference is available as "Prior Art" to the instant application.

SUMMARY OF THE INVENTION

As discussed above, there remains a need for the development of novel therapeutics that mimick or modulate HGF/SF activity. The present invention is directed to novel therapeutics capable of mimicking or modulating the activities of various cytokines, including but not limited to hepatocyte growth factor (HGF; also known as scatter factor (SF)), epidermal growth factor (EGF), vascular endothelial growth factor (VEGF) and nerve growth factor (NGF), by way of non-limiting examples, or at least providing one or more of the same biological activities as the foregoing exemplary but non-limiting cytokines. Moreover, the compounds of the invention are capable of activating, agonizing or inducing phosphorylation of, and/or directly activating, the signaling pathways of various receptor tyrosine kinases, including but not limited to the HGF/SF receptor (c-met), the EGF receptor, the VEGF receptor and the NGF receptor.

In general, certain novel inventive compounds have the structure shown in Formula (I) below:

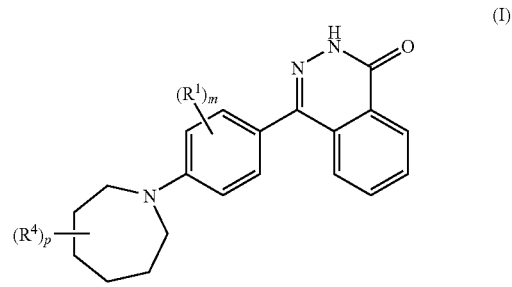

(I)

wherein m, p, $R^1$ and $R^4$ are as described generally and in classes and subclasses herein, tautomers thereof, pharmaceutical compositions thereof, which compounds are useful as modulators of HGF/SF activity as well as that of other receptor tyrosine kinases.

In certain other embodiments, the present invention provides compounds of Formula ($II^4$):

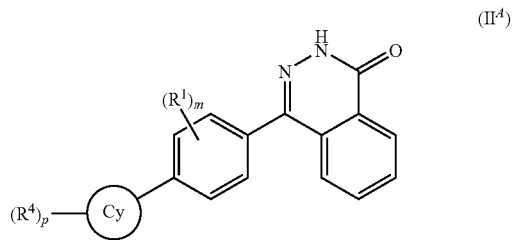

($II^4$)

wherein m, p, $R^1$ and $R^4$ are as described generally and in classes and subclasses herein, tautomers thereof, pharmaceutical compositions thereof, which compounds are useful as modulators of HGF/SF activity as well as that of other receptor tyrosine kinases.

In another aspect, the invention is directed to compositions comprising of any of the compounds disclosed herein.

In another aspect, the invention provides methods for the use of any of the compounds disclosed herein for modulating HGF/SF activity in a patient or a biological sample, in particular providing anti-fibrotic and anti-apoptotic activities. The compounds and pharmaceutical compositions of the invention have properties of HGF/SF and are useful in the treatment of any disease, disorder or condition in which prophylactic or therapeutic administration of HGF/SF would be useful.

In another aspect, the invention provides methods for the use of any of the compounds disclosed herein for treating or lessening the severity of a disease, disorder or condition associated with HGF/SF or other cytokine activity.

In yet other aspects, the invention provides methods for the prophylaxis or treatment of conditions and diseases in which promoting or mimicking the activity of cytokines is desired, or biological activities resulting from activating, agonizing or inducing phosphorylation of c-met or other receptor tyrosine kinases. In a preferred embodiment, the activity is inducing endothelial cell proliferation or angiogenesis. In another embodiment, the activity is to induce proliferation of other cells, such as epithelial cells, neuronal cells, Schwann cells, or oligodendrocyte cells. In a further embodiment, the activity is to induce growth of neuronal axons. In yet another embodiment, the activity is induction of myelin production. In yet another embodiment, the activity is protection against apoptosis. In yet another embodiment, the activity is anti-fibrotic. The compounds described herein are useful in the treatment of conditions and diseases where inducing endothelial cell proliferation or therapeutic angiogenesis is beneficial, where inducing proliferation of cells such as epithelial cells, neuronal cells, Schwann cells, and oligodendrocyte cells is beneficial, where inducing axonal growth is beneficial, where induction of myelin production is beneficial, where protection against apoptosis is beneficial, where anti-fibrosis is beneficial, or where all or some of the foregoing activities are beneficial, including but not limited to fibrotic liver disease, hepatic ischemia-reperfusion injury, cerebral infarction, ischemic heart disease, renal disease or lung (pulmonary) fibrosis, multiple sclerosis or various neurodegenerative diseases. In certain embodiments, the method is useful for treating a disease or condition, or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; other cardiovascular diseases; diabetes; renal failure; renal fibrosis, lung fibrosis or idiopathic pulmonary fibrosis; multiple sclerosis; and neurodegenerative diseases such as but not limited to metachromatic leukodystrophy, Refsum's disease, adrenoleukodystrophy, Krabbe's disease, phenylketonuria, Canavan disease, Pelizaeus-Merzbacher disease and Alexander's disease. In certain exemplary embodiments, the method is for the treatment of wounds for acceleration of healing; promoting vascularization of a damaged and/or ischemic organ, transplant or graft; amelioration of ischemia/reperfusion injury in the brain, heart, liver, kidney, or other tissues or organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus. Use of the compound is also provided for prophylaxis or preventing the occurrence of the diseases in subjects, and in particular subjects susceptible to of exhibiting risk factors for, the aforementioned diseases and conditions. Common among the foregoing conditions is benefit therein by promoting endothelial cell growth, angiogenesis or formation of new blood vessels. Moreover, the compounds of the invention are beneficial in providing biological activities resulting from activating, agonizing, phosphorylating, or in any other way activating the signaling pathway of the HGF/SF receptor, c-met, or other receptor tyrosine kinases.

Definitions

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}$$SO_2$—, —$NR^{G2}$$SO_2$$NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched) or branched aliphatic hydrocarbons as defined by IUPAC, which are optionally substituted with one or more functional groups. As defined herein, "aliphatic" is intended to include optionally substituted alkyl, alkenyl and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargy1), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "cycloalkyl", as used herein, refers to cyclcic alkyl groups, specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like. Additional examples of generally applicable substituents are illustrated by the specific embodiments shown in the Examples that are described herein.

The term "heteroaliphatic", as used herein, refers to aliphatic moieties in which one or more carbon atoms in the main chain have been replaced with a heteroatom. Thus, a heteroaliphatic group refers to an aliphatic chain which contains one or more oxygen, sulfur, nitrogen, phosphorus or silicon atoms in place of carbon atoms in the aliphatic main chain. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one or more hydrogen atoms thereon with aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic". Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring having p-orbitals perpendicular to the plane of the ring at each ring atom, and satisfying the Huckel rule where the number of pi electrons in the ring is (4n+2) wherein n is an integer. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

As defined herein, "aryl" and "heteroaryl" groups (including bicyclic aryl groups) can be unsubstituted or substituted, wherein substitution includes replacement of one or more of the hydrogen atoms thereon independently with any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thio-alkyl include, but are not limited to, methylthio, ethylthio, propylthio, isopropylthio, n-butylthio, and the like.

The term "alkylamino" refers to a group having the structure —NHR' wherein R' is aliphatic or alicyclic, as defined herein. The term "aminoalkyl" refers to a group having the structure $NH_2R'$—, wherein R' is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R' is an alkyl, alkenyl, or alkynyl group containing 1-8 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N$(R_x)_2$; —OC(=O)$R_x$; —$OCO_2R_x$; —OC(=O)N$(R_x)_2$; —N$(R_x)_2$; —$OR_x$; —$SR_x$; —S(O)$R_x$; —S(O)$_2R_x$; —$NR_x$(CO)$R_x$; —N$(R_x)CO_2R_x$; —N$(R_x)S(O)_2R_x$; —N$(R_x)$C(=O)N$(R_x)_2$; —S(O)$_2$N$(R_x)_2$; wherein each occurrence of $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—$NH_2$), secondary (—$NHR_x$), tertiary (—$NR_xR_y$) or quaternary (—$N^+R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R, where R is an aliphatic, alicyclic, heteroaliphatic, heterocyclic, aromatic or heteroaromatic moiety, as defined herein.

The term "$C_{2-6}$alkenylene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Another example is an N-methyl derivative of a compound, which is susceptible to oxidative metabolism resulting in N-demethylation. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

The term "tautomerization" refers to the phenomenon wherein a proton of one atom of a molecule shifts to another atom. See, Jerry March, Advanced Organic Chemistry: Reactions, Mechanisms and Structures, Fourth Edition, John Wiley & Sons, pages 69-74 (1992). The term "tautomer" as used herein, refers to the compounds produced by the proton shift.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-alkyl and N-aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "isolated" when applied to the compounds of the present invention, refers to such compounds that are (i) separated from at least some components with which they are associated in nature or when they are made and/or (ii) produced, prepared or manufactured by the hand of man.

As used herein the term "biological sample" includes, without limitation, cell cultures or extracts thereof; biopsied material obtained from an animal (e.g., mammal) or extracts thereof; and blood, saliva, urine, feces, semen, tears, or other body fluids or extracts thereof; or purified versions thereof. For example, the term "biological sample" refers to any solid or fluid sample obtained from, excreted by or secreted by any living organism, including single-celled microorganisms (such as bacteria and yeasts) and multicellular organisms (such as plants and animals, for instance a vertebrate or a mammal, and in particular a healthy or apparently healthy human subject or a human patient affected by a condition or disease to be diagnosed or investigated). The biological sample can be in any form, including a solid material such as a tissue, cells, a cell pellet, a cell extract, cell homogenates, or cell fractions; or a biopsy, or a biological fluid. The biological fluid may be obtained from any site (e.g. blood, saliva (or a mouth wash containing buccal cells), tears, plasma, serum, urine, bile, seminal fluid, cerebrospinal fluid, amniotic fluid, peritoneal fluid, and pleural fluid, or cells therefrom, aqueous or vitreous humor, or any bodily secretion), a transudate, an exudate (e.g. fluid obtained from an abscess or any other site of infection or inflammation), or fluid obtained from a joint (e.g. a normal joint or a joint affected by disease such as rheumatoid arthritis, osteoarthritis, gout or septic arthritis). The biological sample can be obtained from any organ or tissue (including a biopsy or autopsy specimen) or may comprise cells (whether primary cells or cultured cells) or medium conditioned by any cell, tissue or organ. Biological samples may also include sections of tissues such as frozen sections taken for histological purposes. Biological samples also include mixtures of biological molecules including proteins, lipids, carbohydrates and nucleic acids generated by partial or complete fractionation of cell or tissue homogenates. Although the sample is preferably taken from a human subject, biological samples may be from any animal, plant, bacteria, virus, yeast, etc. The term animal, as used herein, refers to humans as well as non-human animals, at any stage of development, including, for example, mammals, birds, reptiles, amphibians, fish, worms and single cells. Cell cultures and live tissue samples are considered to be pluralities of animals. In certain exemplary embodiments, the non-human animal is a mammal (e.g., a rodent, a mouse, a rat, a rabbit, a monkey, a dog, a cat, a sheep, cattle, a primate, or a pig). An animal may be a transgenic animal or a human clone. If desired, the biological sample may be subjected to preliminary processing, including preliminary separation techniques.

BRIEF DESCRIPTION OF THE DRAWING

FIGS. 14A-C: treatment initiated at the time of TAA induction, showing hydroxyproline content (A), alpha-SMA level (B) and collagen-1 gene expression (C). Delayed oral treatment, FIGS. 14D-F: showing hydroxyproline (D), portal pressure (E) and fibrotic score (F).

DETAILED DESCRIPTION OF CERTAIN PREFERRED EMBODIMENTS OF THE INVENTION

Figure 1:
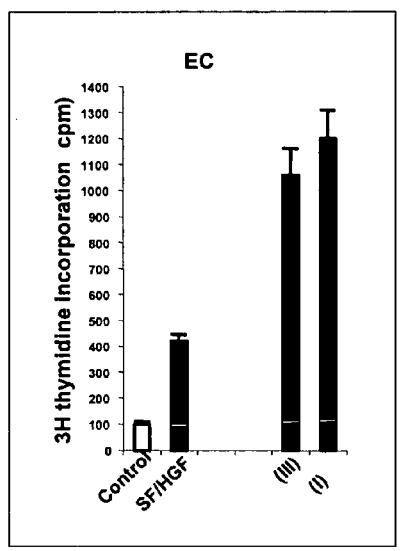
FIG. 1A-D show the increase in HUVEC proliferation by compounds of the invention (A) compared to control and HGF, and dose-response curves using three compounds of the invention (B-D).
Figure 1:
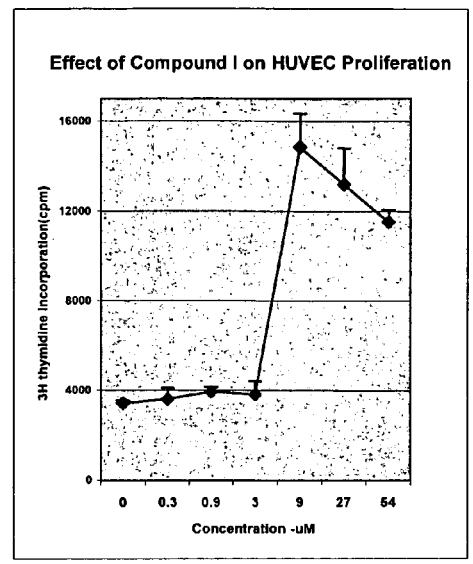
Figure 1:
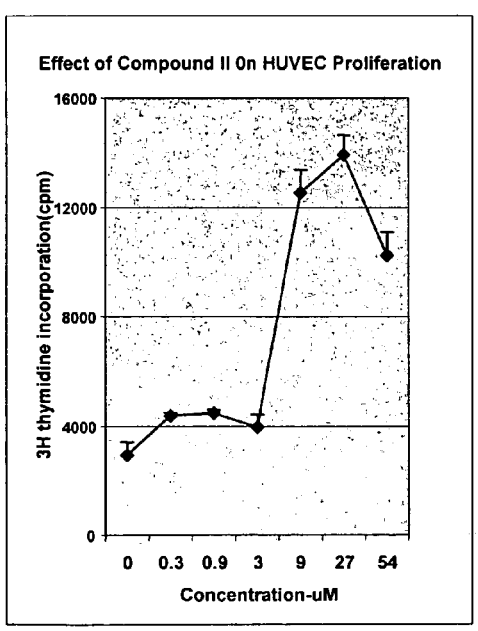
Figure 1:
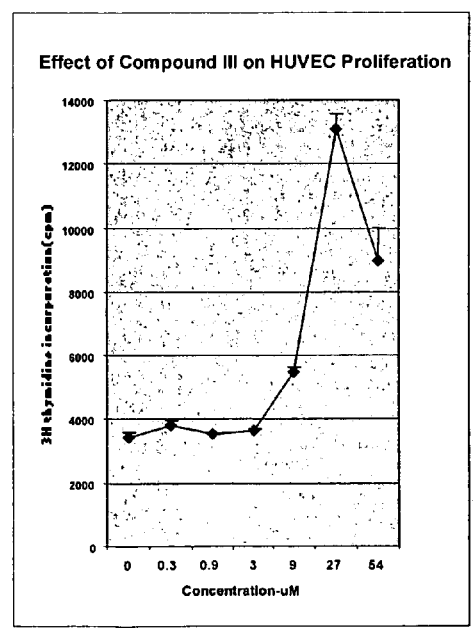

The compounds of the invention are capable of mimicking or modulating the activities of cytokines, such as hepatocyte growth factor (HGF; also known as scatter factor (SF)), epidermal growth factor (EGF), vascular endothelial growth factor (VEGF) and nerve growth factor (NGF), or provide one or more of the same biological activities as the foregoing exemplary but non-limiting cytokines. Moreover, the compounds of the invention are capable of activating, agonizing or inducing phosphorylation of, and/or directly-activating the signaling pathways of various receptor tyrosine kinases, including but not limited to the HGF/SF receptor (c-met), EGF receptor, VEGF receptor or NGF receptor. The compounds of the invention also induce the phosphorylation of c-met or agonize, activate or phosphorylate other receptor tyrosine kinases, such as but not limited to those mentioned above. In preferred embodiments, inventive compounds are small molecule HGF/SF mimics or agonists. Without wishing to be bound by any particular theory, in certain other embodiments, small-molecule compounds of the invention modulate the activity of the HGF/SF receptor, c-met. In further embodiments, compounds of the invention bind to c-met.

Having such biological activities, the compounds of the invention, optionally provided in a pharmaceutical composition, find use in the prophylaxis or treatment of conditions and diseases in which promoting or mimicking the activity of the aforementioned cytokines, among others, is desired, or exhibiting biological activities resulting from activating, agonizing or inducing phosphorylation of c-met or other receptor tyrosine kinases. In a preferred embodiment, the activity is inducing endothelial cell proliferation or angiogenesis. In another embodiment, the activity is to induce proliferation of other cells, such as epithelial cells, neuronal cells, Schwann cells, or oligodendrocyte cells. In a further embodiment, the activity is to induce growth of neuronal axons. In yet another embodiment, the activity is induction of myelin production. In yet another embodiment, the activity is protection against apoptosis. In yet another embodiment, the activity is anti-fibrotic.

The compounds of the invention are useful in the treatment of conditions and diseases where inducing endothelial cell proliferation or therapeutic angiogenesis is beneficial, where inducing proliferation of cells such as epithelial cells, neuronal cells, Schwann cells, or oligodendrocyte cells is beneficial, where inducing axonal growth is beneficial, where induction of myelin production is beneficial, where protection against apoptosis is beneficial, where anti-fibrosis is beneficial, or where all or some of these activities are beneficial, including but not limited to fibrotic liver disease, hepatic ischemia-reperfusion injury, cerebral infarction, ischemic heart disease, renal disease or lung (pulmonary) fibrosis. In certain embodiments, the method is useful for treating a disease or condition, or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke, traumatic head injury, spinal cord injury, and other cerebrovascular diseases; diabetes; myocardial ischemia; atherosclerosis; peripheral vascular disease; other cardiovascular diseases; renal failure; renal fibrosis; and idiopathic pulmonary fibrosis. In certain exemplary embodiments, the method is for the treatment of wounds for acceleration of healing; promoting vascularization of a damaged and/or ischemic organ, transplant or graft; amelioration of ischemia/reperfusion injury in the brain, heart, liver, kidney, and other tissues and organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus.

Another disease amenable to treatment by the compounds and compositions of the invention is multiple sclerosis (MS). MS usually manifests itself between the 20th and 50th years of life. Current estimates are that approximately 2.5 million people worldwide have MS, with between 250,000 and 350,000 cases in the United States, 50,000 cases in Canada, 130,000 cases in Germany, 85,000 cases in the United Kingdom, 75,000 cases in France, 50,000 cases in Italy, and 11,000 cases in Switzerland. MS attacks the white matter of the central nervous system (CNS). In its classic manifestation (90% of all cases), it is characterized by alternating relapsing/remitting phases with periods of remission growing shorter over time. Its symptoms include any combination of spastic paraparesis, unsteady gait, diplopia, and incontinence.

Another category of diseases also amenable to treatment herein are the hereditary neurodegenerative disorders. This category includes the eight identified leukodystrophies: metachromatic leukodystrophy, Refsum's disease, adrenoleukodystrophy, Krabbe's disease, phenylketonuria, Canavan disease, Pelizaeus-Merzbacher disease and Alexander's disease. The first six are storage disorders. The lack or the malfunctioning of an enzyme causes a toxic buildup of chemical substances. In Pelizaeus-Merzbacher disease myelin is never formed (dysmyelination) because of a mutation in the gene that produces a basic protein of CNS myelin. The etiology of Alexander's disease remains largely unknown. The clinical course of hereditary demyelinating disorders, which usually tend to manifest themselves in infancy or early childhood, is tragic. Previously normal children are deprived, in rapid progression, of sight, hearing, speech, and ambulation. Equally tragic is their prognosis: death within a few years.

Use of the compound for prophylaxis or preventing the occurrence of the diseases in subjects, and in particular subjects susceptible to of exhibiting risk factors for, the aforementioned diseases and conditions. Common among the foregoing conditions is benefit therein by promoting endothelial cell growth, angiogenesis or formation of new blood vessels. These are merely exemplary of the biological activities of the present compounds.

Compounds of this invention include those generally set forth above and described specifically herein, and are illustrated in part by the various classes, subgenera and species disclosed herein.

Additionally, the present invention provides pharmaceutically acceptable derivatives of the inventive compounds, and methods of treating a subject using these compounds, pharmaceutical compositions thereof, or either of these in combination with one or more additional therapeutic agents.

1) General Description of Compounds of the Invention

In certain embodiments, compounds of the invention include compounds of the general Formula (I) as further defined below:

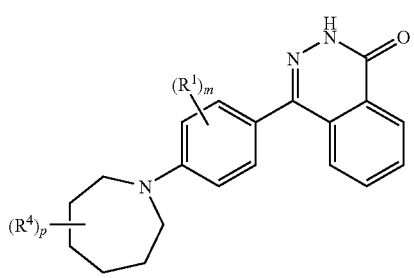

(I)

or pharmaceutically acceptable derivative thereof;
wherein m is an integer from 1 to 4;
p is an integer from 1 to 6;
each occurrence of $R^1$ and $R^4$ is independently hydrogen, halogen, hydroxyl, —$NO_2$, —$NH_2$, —CN, an optionally substituted aliphatic, alicyclic, heteroaliphatic, heterocyclic, aromatic or heteroaromatic moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted aliphatic, alicyclic, heteroaliphatic, heterocyclic, aromatic, heteroaromatic or acyl moiety;

$R^a$, for each occurrence, is independently selected from the group consisting of hydrogen and an optionally substituted aliphatic, alicyclic, heteroaliphatic, heterocyclic, aromatic, or heteroaromatic moiety;

$R^b$ and $R^c$, for each occurrence, are independently selected from the group consisting of hydrogen; hydroxy; $SO_2R^d$; and aliphatic, alicyclic, heteroaliphatic, heterocyclic, aromatic, heteroaromatic or acyl moiety;

$R^d$, for each occurrence, is independently selected from the group consisting of hydrogen; —$N(R^e)_2$; aliphatic, alicyclic, heteroaliphatic, heterocyclic, aromatic or heteroaromatic; and $R^e$, for each occurrence, is independently hydrogen or aliphatic.

In certain other embodiments, compounds of formula (I) are defined as follows:
m is an integer from 1 to 4;
p is an integer from 1 to 6;
each occurrence of $R^1$ and $R^4$ is independently hydrogen, halogen, hydroxyl, —$NO_2$, —$NH_2$, —CN, an optionally substituted alkyl, heteroalkyl, cycloalkyl, heterocyclic, aryl or heteroaryl moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted alkyl, heteroalkyl, cycloalkyl, heterocyclic, aryl, heteroaryl or acyl moiety;

$R^a$, for each occurrence, is independently hydrogen or an optionally substituted alkyl, heteroalkyl, cycloalkyl, heterocyclic, aryl or heteroaryl moiety;

$R^b$ and $R^c$, for each occurrence, are independently hydrogen, hydroxy, $SO_2R^d$, or an alkyl, heteroalkyl, cycloalkyl, heterocyclic, aryl, heteroaryl or acyl moiety;

$R^d$, for each occurrence, is independently hydrogen, —$N(R^e)_2$, alkyl, heteroalkyl, cycloalkyl, heterocyclic, aryl or heteroaryl; and $R^e$, for each occurrence, is independently hydrogen or alkyl.

In another aspect, the invention provides compounds of formula (II):

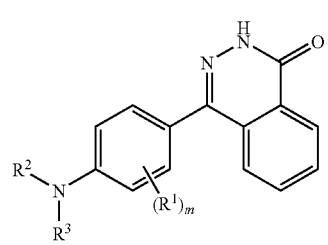

(II)

or pharmaceutically acceptable derivatives thereof;
m is an integer from 1 to 4;
each occurrence of $R^1$ is independently hydrogen, halogen, hydroxyl, —$NO_2$, —$NH_2$, —CN, an optionally substituted aliphatic, alicyclic, heteroaliphatic, heterocyclic, aromatic or heteroaromatic moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted aliphatic, alicyclic, heteroaliphatic, heterocyclic, aromatic, heteroaromatic or acyl moiety;

$R^2$ and $R^3$ are independently hydrogen, hydroxyl, —$NH_2$, an optionally substituted aliphatic, heteroaliphatic, alicyclic, heterocyclic, aromatic or heteroaromatic moiety, —$OR^R$, —$S(=O)_nR^d$, —$NR^bR^c$, —$C(=O)R^a$ or —$C(=O)OR^a$; wherein n is 0-2, $R^R$ is an optionally substituted aliphatic, heteroaliphatic, alicyclic, heterocyclic, aromatic or heteroaromatic or acyl moiety; or $R^2$ and $R^3$ taken together with the nitrogen to which they are attached form an optionally substituted heteroaromatic or heterocyclic group other than an optionally substituted homopiperidinyl group comprising 4-10 ring members and 0-3 additional heteroatoms selected from the group consisting of O, N and S; the heteroaromatic or heterocyclic group optionally further substituted with one or more optionally substituted aliphatic, alicyclic, heteroaliphatic, heterocyclic, aromatic, heteroaromatic or acyl groups;

$R^a$, for each occurrence, is hydrogen or an optionally substituted aliphatic, alicyclic, heteroaliphatic, heterocyclic, aromatic, or heteroaromatic moiety;

$R^b$ and $R^c$, for each occurrence, are independently hydrogen, hydroxy, $SO_2R^d$, or an optionally substituted aliphatic, alicyclic, heteroaliphatic, heterocyclic, aromatic, heteroaromatic or acyl moiety;

$R^d$, for each occurrence, is independently hydrogen, $-N(R^e)_2$, or an optionally substituted aliphatic, alicyclic, heteroaliphatic, heterocyclic, aromatic or heteroaromatic moiety; and $R^e$, for each occurrence, is independently hydrogen or aliphatic.

In certain other embodiments, compounds of formula (II) are defined as follows:

m is an integer from 1 to 4;

each occurrence of $R^1$ is independently hydrogen, halogen, hydroxyl, $-NO_2$, $-NH_2$, $-CN$, an optionally substituted alkyl, heteroalkyl, cycloalkyl, heterocyclic, aryl or heteroaryl moiety, $-OR^R$, $-S(=O)_nR^d$, $-NR^bR^c$, $-C(=O)R^a$, $-OPO_2OR^a$ or $-C(=O)OR^a$; wherein n is 0-2, $R^R$ is an optionally substituted alkyl, heteroalkyl, cycloalkyl, heterocyclic, aryl, heteroaryl or acyl moiety;

$R^2$ and $R^3$ are independently hydrogen, hydroxyl, $-NH_2$, an optionally substituted alkyl, heteroalkyl, cycloalkyl, heterocyclic, aryl or heteroaryl moiety, $-OR^R$, $-S(=O)_nR^d$, $-NR^bR^c$, $-C(=O)R^a$ or $-C(=O)OR^a$; wherein n is 0-2, $R^R$ is an optionally substituted alkyl, heteroalkyl, cycloalkyl, heterocyclic, aryl, heteroaryl or acyl moiety; or $R^2$ and $R^3$ taken together with the nitrogen to which they are attached form a optionally substituted heteroaryl or heterocyclic group other than an optionally substituted homopiperidinyl group comprising 4-10 ring members and 0-3 additional heteroatoms selected from the group consisting of O, N and S; the heteroaryl or heterocyclic group optionally further substituted with one or more optionally substituted alkyl, cycloalkyl, heteroalkyl, heterocyclic, aryl, heteroaryl or acyl groups;

wherein $R^a$, for each occurrence, is independently hydrogen or an optionally substituted alkyl, heteroalkyl, cycloalkyl, heterocyclic, aryl or heteroaryl moiety;

$R^b$ and $R^c$, for each occurrence, are independently hydrogen, hydroxy, $SO_2R^d$, or an alkyl, heteroalkyl, cycloalkyl, heterocyclic, aryl, heteroaryl or acyl moiety;

$R^d$, for each occurrence, is independently hydrogen, $-N(R^e)_2$, alkyl, heteroalkyl, cycloalkyl, heterocyclic, aryl or heteroaryl; and $R^e$, for each occurrence, is independently hydrogen or alkyl.

In certain embodiments, the present invention defines certain classes of compounds which are of special interest. For example, one class of compounds of special interest includes those compounds having the structure of formula ($II^A$) in which the compound has the structure:

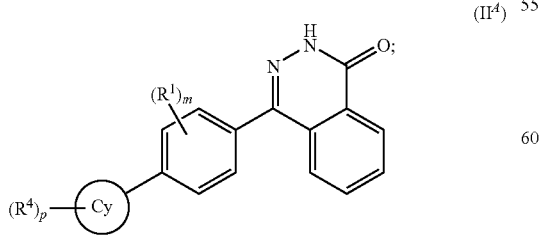

($II^A$)

wherein m, p, $R^1$ and $R^4$ are as defined in classes and subclasses herein; and Cy is an optionally substituted N-linked 5- to 10-membered heterocyclic group other than an optionally substituted homopiperidinyl group.

Another class of compounds of special interest includes those compounds having the structure of formula ($II^B$) in which the compound has the structure:

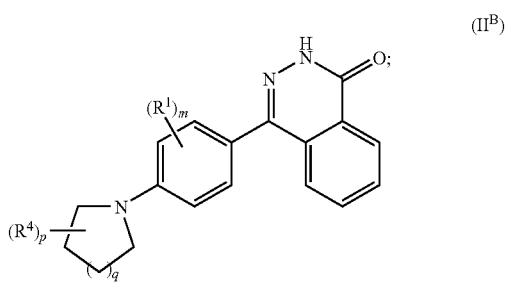

($II^B$)

wherein m, p, $R^1$ and $R^4$ are as defined in classes and subclasses herein; and q is an integer selected from 1, 2 or 4.

In certain embodiments, for compounds of formula ($II^A$) having the structure:

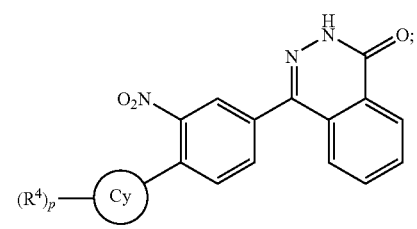

$-Cy-(R^4)_p$ is not one of the following structures:

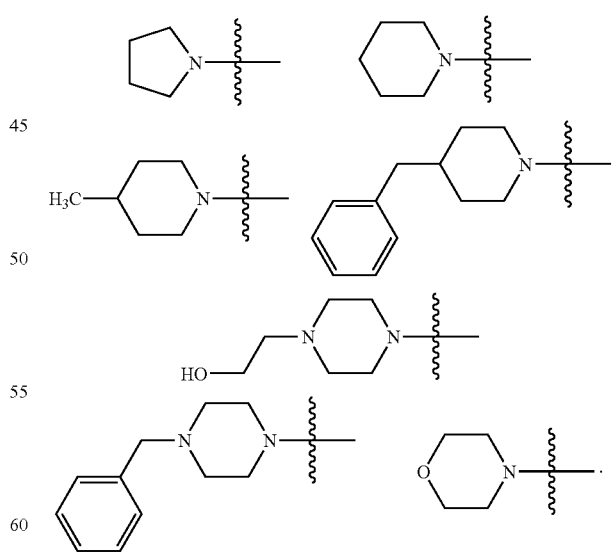

In certain embodiments, for compounds of formula ($II^A$), the following groups do not occur simultaneously as defined:

m is 1; $R^1$ is H and $-Cy-(R^4)_p$ is one of the following structures:

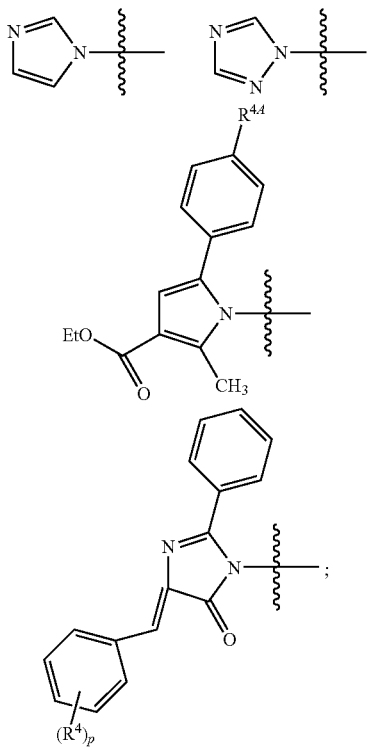

wherein R⁴ᴬ is hydrogen, methyl, methoxy, chloro or —NO₂ and p and R⁴ are as defined above.

A number of important subclasses of each of the foregoing classes of compounds of formulae (I) and (II) deserve separate mention; these subclasses include subclasses of the foregoing classes in which:

i) each occurrence of $R^1$ is independently hydrogen, halogen, hydroxyl, —NO₂, —NH₂, —CN, an optionally substituted alkyl, heteroalkyl, cycloalkyl, heterocyclic, aryl or heteroaryl moiety, —OR$^R$, —S(=O)$_n$R$^d$, —NR$^b$R$^c$, —C(=O)R$^a$, —OPO₂OR$^a$ or —C(=O)OR$^a$; wherein n is 0-2, R$^R$ is an optionally substituted alkyl, heteroalkyl, cycloalkyl, heterocyclic, aryl, heteroaryl or acyl moiety; wherein R$_a$ is as defined in subset lxvi) below;

ii) at least one occurrence of $R^1$ is hydrogen;

iii) at least one occurrence of $R^1$ is —NO₂;

iv) at least one occurrence of $R^1$ is —NH²;

v) at least one occurrence of $R^1$ is —COOH, —C(=O)OCH₃, —COCH₃, —CONH₂, —SO₂OH, —SO₂CH₃, -SO₂CF₃, —OPO₂OH, —NHC(=O)CH₃, —NHC(=O)CF₃, —NHC(=O)CH₃, —NHC(=O)CF₃, —NHSO₂CH₃ or —NHSO₂CF₃.

vi) at least one occurrence of $R^1$ is halogen;

vii) at least one occurrence of $R^1$ is an optionally substituted N-linked heterocyclic group;

viii) at least one occurrence of $R^1$ is an optionally substituted N-pyrrolyl group;

ix) at least one occurrence of $R^1$ is an aliphatic moiety;

x) at least one occurrence of $R^1$ is an alkyl moiety;

xi) at least one occurrence of $R^1$ is a lower alkyl moiety;

xii) m is 1 and at least one occurrence of $R^1$ is ortho to the bond to the phthalazinone ring;

xiii) m is 1 and at least one occurrence of $R^1$ is meta to the bond to the phthalazinone ring;

xiv) each occurrence of $R^1$ is independently hydrogen, —NO₂, —NH², —COOH, —C(=O)OCH₂, —COCH₃, —CONH₂, —SO₂OH, —SO₂CH₃, —SO₂CF₃, —OPO₂OH, —NHC(=O)CH₃, —NHC(=O)CF₃, —NHSO₂CH₃, —NHSO₂CF₃, halogen, an optionally substituted N-linked heterocyclic group or an aliphatic moiety;

xv) each occurrence of $R^1$ is independently hydrogen, —NO₂, —NH₂, —COOH, —C(=O)OCH₃, —COCH₃, —CONH₂, —SO₂OH, —SO₂CH₃, —SO₂CF₃, —OPO₂OH, —NHC(=O)CH₃, —NHC(=O)CF₃, —NHSO₂CH₃, —NHSO₂CF₃, halogen, an optionally substituted N-pyrrolyl group or a lower alkyl moiety;

xvi) $R^2$ and $R^3$ are independently hydrogen, hydroxyl, —NH₂, an optionally substituted alkyl, heteroalkyl, cycloalkyl, heterocyclic, aryl or heteroaryl moiety, —OR$^R$, —S(=O)$_n$R$^d$, —NR$^b$R$^c$, —C(=O)R$^a$ or —C(=O)OR$^a$; wherein n is 0-2, R$^R$ is an optionally substituted alkyl, heteroalkyl, cycloalkyl, heterocyclic, aryl, heteroaryl or acyl moiety; or $R^2$ and $R^3$ taken together with the nitrogen to which they are attached form a optionally substituted heteroaryl or heterocyclic group other than a homopiperidinyl group comprising 4-10 ring members and 0-3 additional heteroatoms selected from the group consisting of O, N and S; the heteroaryl or heterocyclic group optionally further substituted with one or more optionally substituted alkyl, cycloalkyl, heteroalkyl, heterocyclic, aryl, heteroaryl or acyl groups; wherein R$_a$ is as defined in subset lxvi) below;

xvii) $R^2$ and $R^3$ are independently hydrogen, hydroxyl, —NH₂, an optionally substituted alkyl, heteroalkyl, cycloalkyl, heterocyclic, aryl or heteroaryl moiety, —OR$^R$, —S(=O)$_n$R$^d$, —NR$^b$R$^c$, —C(=O)R$^a$ or —C(=O)OR$^a$; wherein n is 0-2, R$^R$ is an optionally substituted alkyl, heteroalkyl, cycloalkyl, heterocyclic, aryl, heteroaryl or acyl moiety; wherein R$_a$ is as defined in subset lxvi) below;

xviii) $R^2$ and $R^3$ are independently hydrogen, lower alkyl or aryl;

xix) $R^2$ and $R^3$ are independently hydrogen or lower alkyl;

xx) $R^2$ and $R^3$ are independently a hydrophobic group;

xxi) $R^2$ and $R^3$ are independently an aliphatic group;

xxii) $R^2$ and $R^3$ are independently an unsubstituted aliphatic group;

xxiii) $R^2$ and $R^3$ are independently a cyclic or acyclic $C_{6-12}$alkyl, $C_{6-12}$alkenyl, or $C_{6-12}$alkynyl group;

xxiv) $R^2$ and $R^3$ are independently an unsubstituted cyclic or acyclic $C_{6-12}$alkyl, $C_{6-12}$alkenyl, or $C_{6-12}$alkynyl group;

xxv) $R^2$ and $R^3$ are independently is an -(alkyl)aryl group;

xxvi) $R^2$ and $R^3$ are independently a unsubstituted -(alkyl) aryl group;

xxvii) $R^2$ and $R^3$ taken together with the nitrogen to which they are attached form a optionally substituted heteroaryl or heterocyclic group other than a homopiperidinyl group comprising 4-10 ring members and 0-3 additional heteroatoms selected from the group consisting of O, N and S; the heteroaryl or heterocyclic group optionally further substituted with one or more optionally substituted alkyl, cycloalkyl, heteroalkyl, heterocyclic, aryl, heteroaryl or acyl groups;

xxviii) $R^2$ and $R^3$ taken together with the nitrogen atom to which they are attached form an optionally substituted pyrrolyl, pyrrolidinyl, imidazolyl, imidazolidinyl, pyrazolyl, pyrazolidinyl, 1,2,3-triazolyl, piperidinyl, morpholinyl, thiomorpholinyl, piperazinyl, indolyl, isoindolyl, indolinyl, indazolyl, benzimidazolyl or purinyl moiety;

xxix) $R^2$ and $R^3$ taken together with the nitrogen to which they are attached form an optionally substituted 6-membered heterocyclic group comprising 0-3 additional heteroatoms selected from the group consisting of O, N and S;

xxx) $R^2$ and $R^3$, taken together, represent the hydrophobic portion of an optionally substituted N-linked ring;

xxxi) $R^2$ and $R^3$, taken together, represent the hydrophobic portion of an N-linked ring substituted with hydrophobic groups, such as one or more aliphatic groups;

xxxii) $R^2$ and $R^3$, taken together, represent the hydrophobic portion of an optionally substituted piperidinyl ring;

xxxiii) $R^2$ and $R^3$, taken together, represent the hydrophobic portion of a piperidinyl ring substituted with hydrophobic groups, such as one or more aliphatic groups;

xxxiv) each occurrence of $R^4$ is independently hydrogen, halogen, hydroxyl, —$NO_2$, —$NH_2$, —CN, an optionally substituted alkyl, heteroalkyl, cycloalkyl, heterocyclic, aryl or heteroaryl moiety, —$OR^R$, —$S(=O)_nR^d$, —$NR^bR^c$, —$C(=O)R^a$, —$OPO_2OR^a$ or —$C(=O)OR^a$; wherein n is 0-2, $R^R$ is an optionally substituted alkyl, heteroalkyl, cycloalkyl, heterocyclic, aryl, heteroaryl or acyl moiety; wherein $R_a$, $R_b$, $R_c$ and $R_d$ are as defined in subsets lxvi), lxvii) and lxviii) below;

xxxv) at least one occurrence of $R^4$ is hydrogen;

xxxvi) at least one occurrence of $R^4$ is a hydrophobic group;

xxxvii) at least one occurrence of $R^4$ is an optionally substituted aliphatic group;

xxxviii) at least one occurrence of $R^4$ is an unsubstituted aliphatic group;

xxxix) at least one occurrence of $R^4$ is an optionally substituted cyclic or acyclic $C_{6-12}$alkyl, $C_{6-12}$alkenyl, or $C_{6-12}$alkynyl group;

xl) at least one occurrence of $R^4$ is an unsubstituted cyclic or acyclic $C_{6-12}$alkyl, $C_{6-12}$alkenyl, or $C_{6-12}$alkynyl group;

xli) at least one occurrence of $R^4$ is an optionally substituted -alkyl)aryl group;

xlii) at least one occurrence of $R^4$ is a unsubstituted -alkyl)aryl group;

xliii) at least one occurrence of $R^4$ is —$NR^bR^c$;

xliv) at least one occurrence of $R^4$ is —$NH_2$;

xlv) at least one occurrence of $R^4$ is —$C(=O)OR^a$; wherein $R_a$ is as defined in subset lxvi) below;

xlvi) at least one occurrence of $R^4$ is —$CO_2H$;

xlvii) p is $\geq 3$ and each occurrence of $R^4$ is independently a cyclic or acyclic $C_{1-6}$alkyl, $C_{2-6}$alkenyl, $C_{2-6}$alkynyl or —($C_{1-6}$alkyl)aryl group;

xlviii) p is $\geq 3$ and each occurrence of $R^4$ is independently methyl, ethyl, propyl, butyl, pentyl, hexyl, i-propyl or benzyl;

xlixi) each occurrence of $R^4$ is independently hydrogen, halogen, an optionally substituted aliphatic group, —$NR^bR^c$, or —$C(=O)OR^a$, wherein $R_a$, $R_b$ and $R_c$ are as defined in subsets lxvi) and lxvii) below;

l) each occurrence of $R^4$ is independently hydrogen, halogen, an optionally substituted cyclic or acyclic $C_{6-12}$alkyl, $C_{6-12}$alkenyl, or $C_{6-12}$alkynyl group, an optionally substituted -(alkyl)aryl group, —$NH_2$ or —$CO_2H$;

li) m is 0;

lii) m is 1;

liii) m is 2;

liv) m is 3;

lv) m is 4;

lvi) p is 0;

lvii) p is 1;

lviii) p is 2;

lix) p is 3;

lx) p is 4;

lxi) p is 5;

lxii) p is 6;

lxiii) q is 1;

lxiv) q is 2;

xlv) q is 4;

lxvi) $R^a$, for each occurrence, is independently hydrogen or an optionally substituted alkyl, heteroalkyl, cycloalkyl, heterocyclic, aryl or heteroaryl moiety;

lxvii) $R^b$ and $R^c$, for each occurrence, are independently hydrogen, hydroxy, $SO_2R^d$, or an alkyl, heteroalkyl, cycloalkyl, heterocyclic, aryl, heteroaryl or acyl moiety;

lxviii) $R^d$, for each occurrence, is independently hydrogen, —$N(R^e)_2$, alkyl, heteroalkyl, cycloalkyl, heterocyclic, aryl or heteroaryl;

lxix) $R^e$, for each occurrence, is independently hydrogen or alkyl; and/or lx) Cy is one of:

wherein q is 1, 2 or 4 and p and $R^4$ are as defined in classes and subclasses herein, and $R^{4A}$ is hydrogen, hydroxy, $SO_2R^d$, or an alkyl, heteroalkyl, cycloalkyl, heterocyclic, aryl, heteroaryl or acyl moiety; wherein $R^d$ is as defined in classes and subclasses herein.

It will be appreciated that for each of the classes and subclasses described above and herein, any one or more occurrences of groups such as aliphatic, heteroaliphatic, alkyl, heteroalkyl may independently be substituted or unsubstituted, linear or branched, saturated or unsaturated; and any one or more occurrences of alicyclic, heterocyclic, cycloalkyl, aryl, heteroaryl, cycloaliphatic, cycloheteroaliphatic may be substituted or unsubstituted.

The reader will also appreciate that all possible combinations of the variables described in i)- through lx) above (e.g., $R^1$-$R^4$, m, p and q, among others) are considered part of the invention. Thus, the invention encompasses any and all compounds of formula I, and subclasses thereof, generated by taking any possible permutation of variables $R^1$-$R^4$, m, p and q, and other variables/substituents (e.g., $R_{a-e}$, etc.) as further defined for $R^1$-$R^4$, described in i)- through lx) above, leading to a stable compound.

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives Thereof):

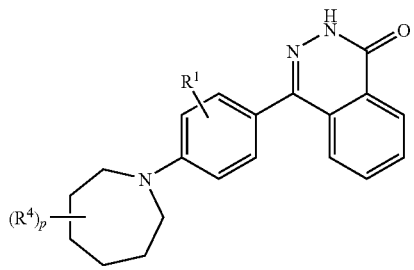

wherein p, $R^1$ and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

II) Compounds of the Formula (and Pharmaceutically Acceptable Derivatives Thereof):

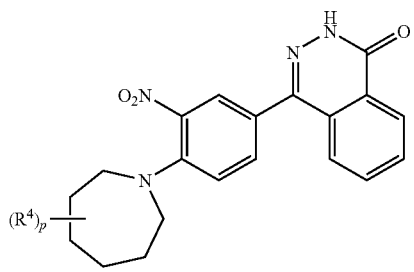

wherein p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

III) Compounds of the Formula (and Pharmaceutically Acceptable Derivatives Thereof):

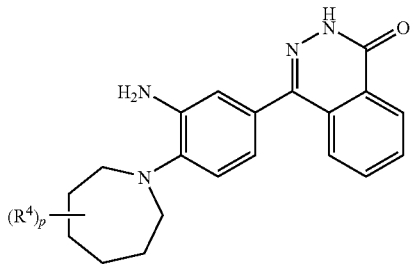

wherein p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

IV) Compounds of the Formula (and Pharmaceutically Acceptable Derivatives Thereof):

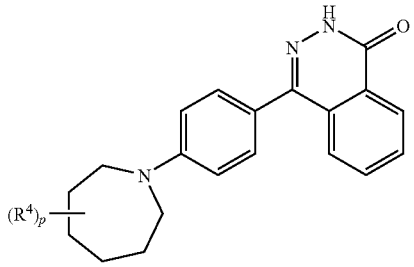

wherein p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

V) Compounds of the Formula (and Pharmaceutically Acceptable Derivatives Thereof):

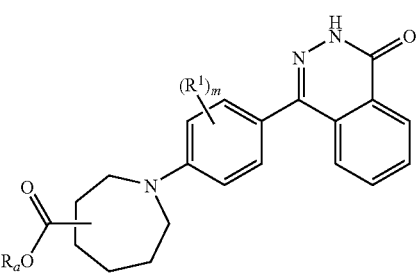

wherein m, $R^1$ and $R_a$ are as defined in classes and subclasses herein. In certain embodiments, $R_a$ is hydrogen. In certain embodiments, $R_a$ is lower alkyl. In certain embodiments, $R_a$ is a hydrophilic group. In certain embodiments, $R_a$ is an optionally substituted cyclic or acyclic $C_{6-12}$alkyl, $C_{6-12}$alkenyl, or $C_{6-12}$alkynyl group. In certain embodiments, $R_a$ is an optionally substituted -(alkyl)aryl group.

VI) Compounds of the Formula (and Pharmaceutically Acceptable Derivatives Thereof):

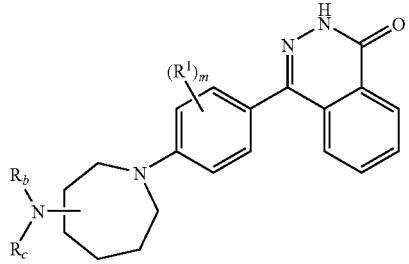

wherein m, $R^1$, $R_b$ and $R_c$ are as defined in classes and subclasses herein. In certain embodiments, $R_b$ and $R_c$ are independently hydrogen or lower alkyl. In certain embodiments, $R_b$ and $R_c$ are independently a hydrophilic group. In certain embodiments, $R_b$ and $R_c$ are independently an optionally substituted cyclic or acyclic $C_{6-12}$alkyl, $C_{6-12}$alkenyl, or $C_{6-12}$alkynyl group. In certain embodiments, $R_b$ and $R_c$ are independently an optionally substituted -(alkyl)aryl group.

VII) Compounds of the Formula (and Pharmaceutically Acceptable Derivatives Thereof):

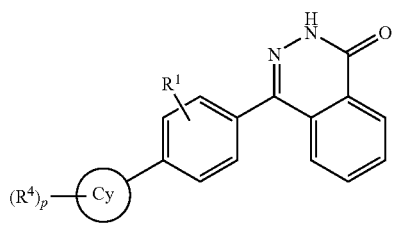

wherein Cy, p, $R^1$ and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

VIII) Compounds of the Formula (and Pharmaceutically Acceptable Derivatives Thereof):

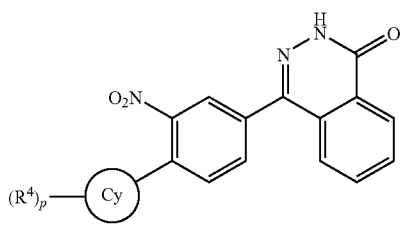

wherein Cy, p and $R^4$ are as defined in classes and subclasses herein; with the proviso that -Cy-$(R^4)_p$ is not one of the following structures:

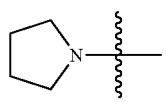 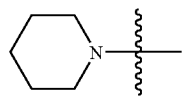

-continued

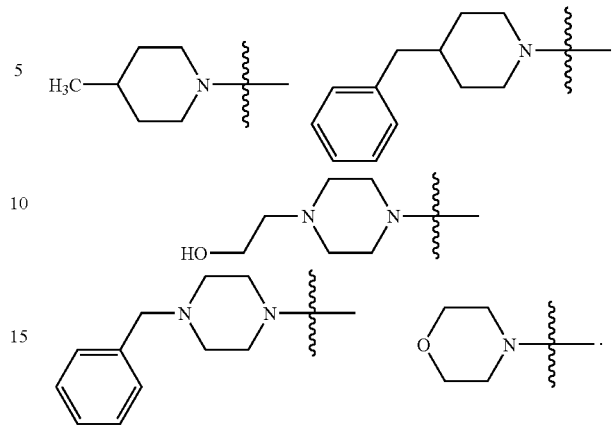

In certain embodiments, p is 1-4 and each occurrence of $R^4$ is independently hydrogen or lower alkyl. In certain embodiments, at least one occurrence of $R^4$ is a hydrophilic group.

IX) Compounds of the Formula (and Pharmaceutically Acceptable Derivatives Thereof):

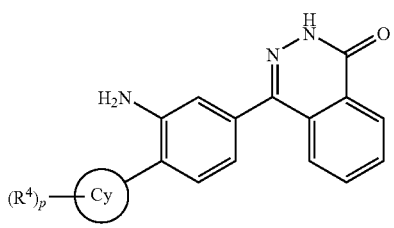

wherein Cy, p and $R^4$ are as defined in classes and subclasses herein. In certain embodiments, p is 1-4 and each occurrence of $R^4$ is independently hydrogen or lower alkyl. In certain embodiments, at least one occurrence of $R^4$ is a hydrophilic group.

X) Compounds of the Formula (and Pharmaceutically Acceptable Derivatives Thereof):

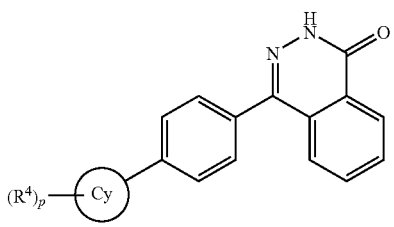

wherein Cy, p and $R^4$ are as defined in classes and subclasses herein, with the proviso that -Cy-$(R^4)_p$ is not one of the following structures:

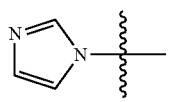 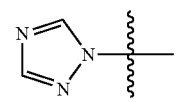

-continued

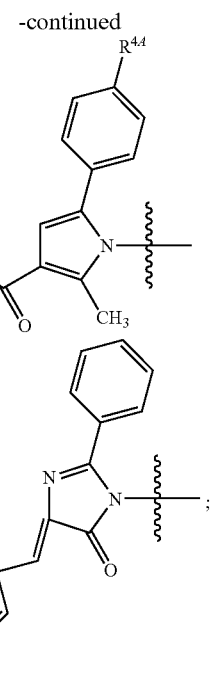

wherein R[4A] is hydrogen, methyl, methoxy, chloro or —NO$_2$ and p and R[4] are as defined in classes and subclasses herein.

In certain embodiments, p is 1-4 and each occurrence of R[4] is independently hydrogen or lower alkyl. In certain embodiments, at least one occurrence of R[4] is a hydrophilic group.

XI) Compounds of the Formula (and Pharmaceutically Acceptable Derivatives Thereof):

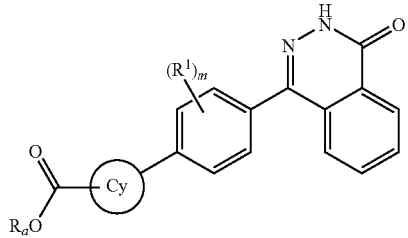

wherein Cy, m, R[1] and R$_a$ are as defined in classes and subclasses herein. In certain embodiments, R$_a$ is hydrogen. In certain embodiments, R$_a$ is lower alkyl.

XII) Compounds of the Formula (and Pharmaceutically Acceptable Derivatives Thereof):

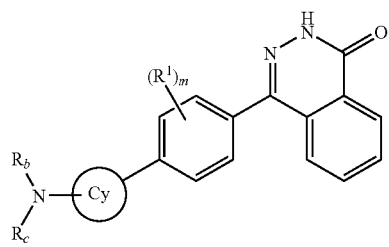

wherein Cy, m, R[1], R$_b$ and R$_c$ are as defined in classes and subclasses herein. In certain embodiments, R$_b$ and R$_c$ are independently hydrogen or lower alkyl.

In certain embodiments, for compounds of classes I-XII above, at least one occurrence of R[4] is a hydrophobic group. In certain embodiments, each occurrence of R[4] is independently a hydrophobic group. In certain embodiments, the hydrophobic group is an aliphatic group. In certain embodiments, the hydrophobic group is an unsubstituted aliphatic group. In certain embodiments, the hydrophobic group is a cyclic or acyclic C$_{6-12}$alkyl, C$_{6-12}$alkenyl, or C$_{6-12}$alkynyl group. In certain embodiments, the hydrophobic group is an unsubstituted cyclic or acyclic C$_{6-12}$alkyl, C$_{6-12}$alkenyl, or C$_{6-12}$alkynyl group. In certain embodiments, the hydrophobic group is a -(alkyl)aryl group. In certain embodiments, the hydrophobic group is an unsubstituted -(alkyl)aryl group.

In certain embodiments, for compounds of classes V and VI above, m is 0-2. In certain embodiments, m is 0. In certain embodiments, m is 1.

In certain embodiments, for compounds of classes I-XII above, p is 0-2. In certain embodiments, p is 0. In certain embodiments, p is 1.

Non-limiting examples of compounds of the invention in Formula (I) include:

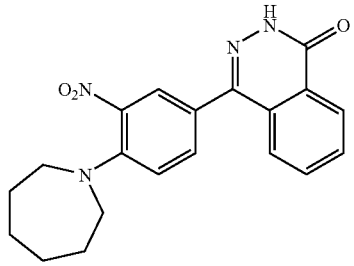

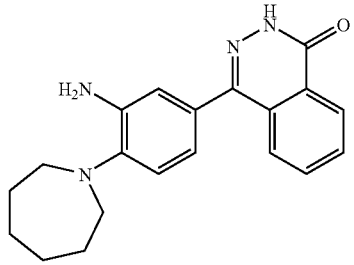

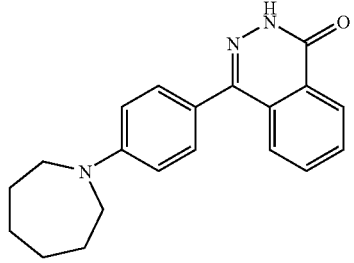

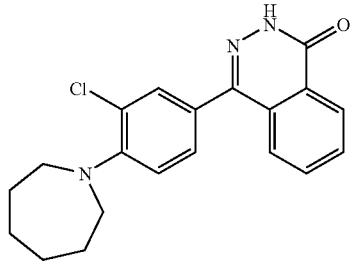

-continued
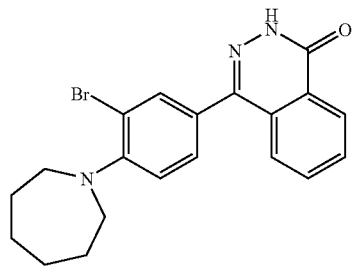
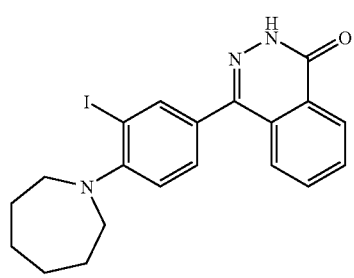
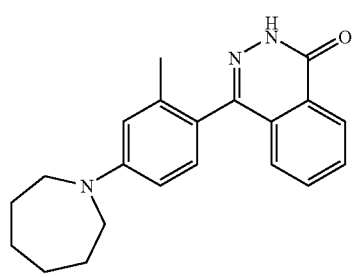
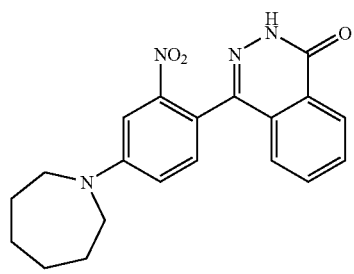
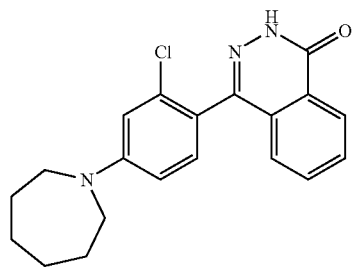
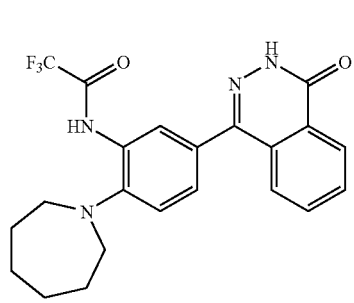
-continued
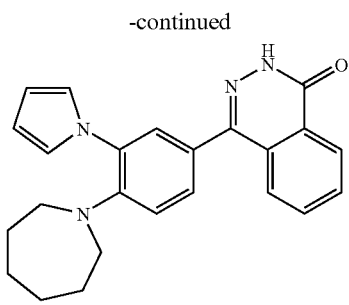
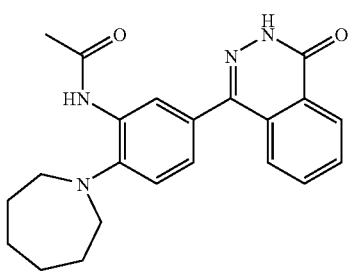
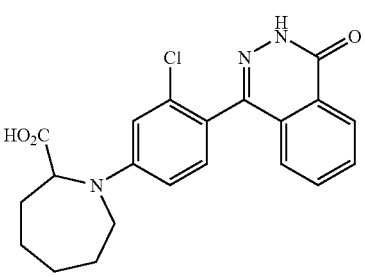
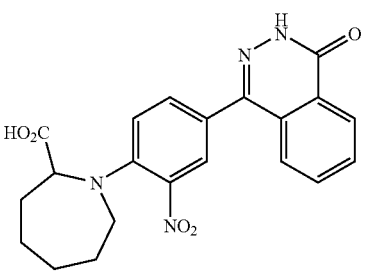
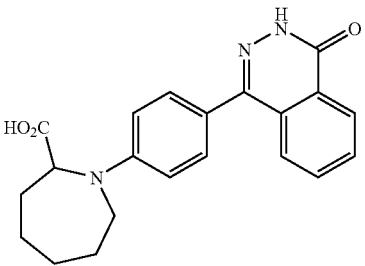
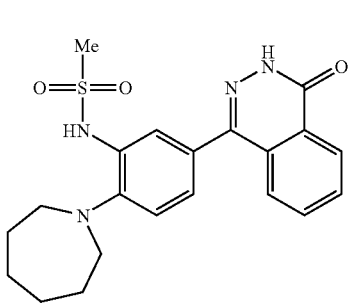

-continued
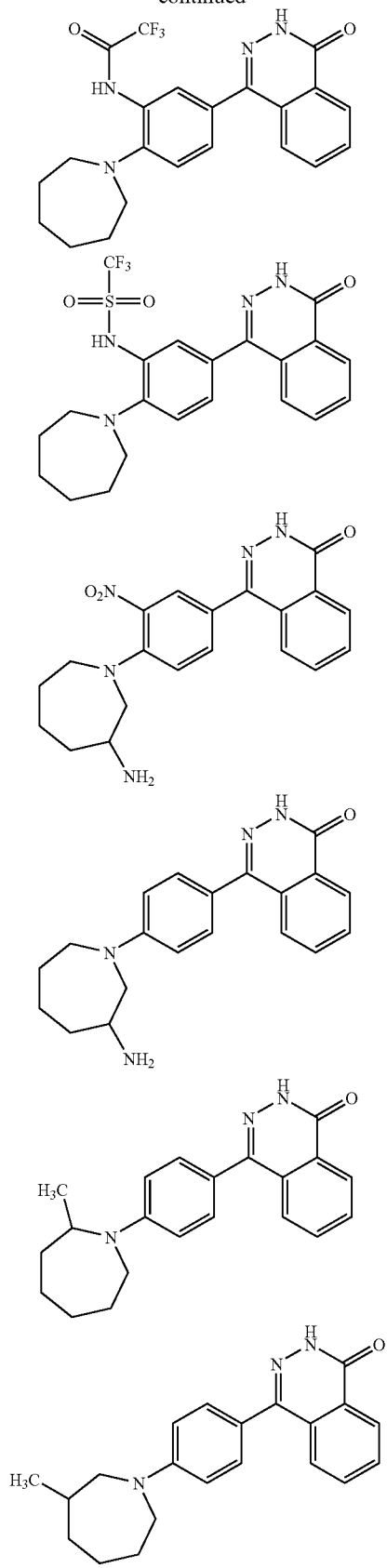
Examples of compounds of Formula (II) where $R^2$ and $R^3$ do not form a ring include:
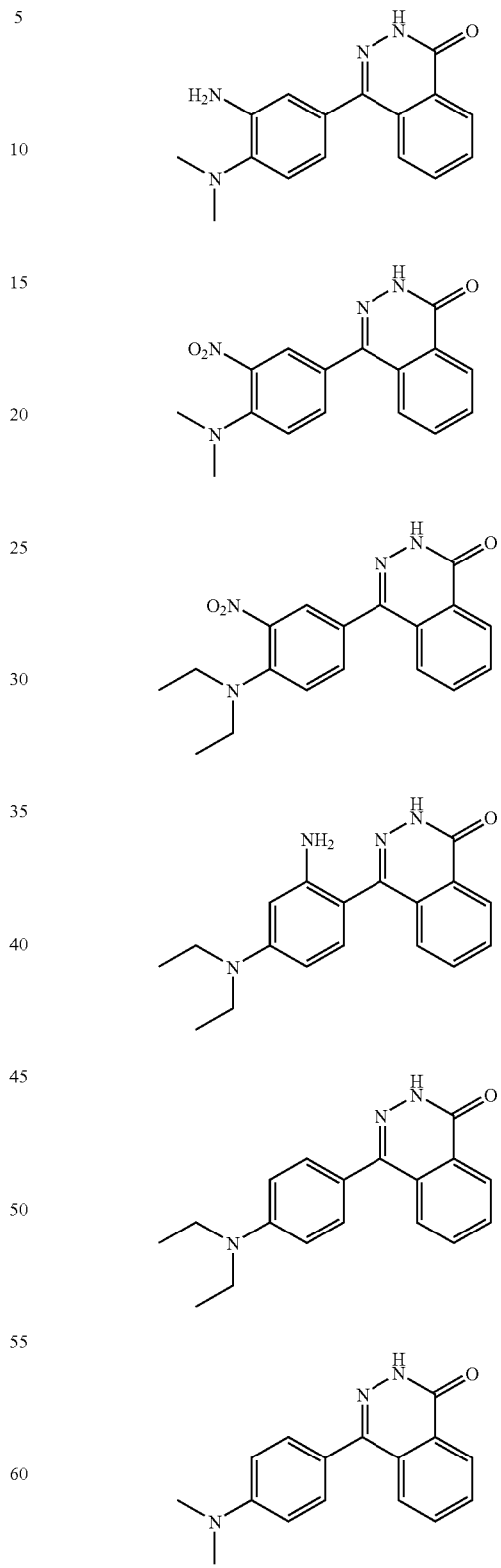
In certain embodiments, compounds of Formula (II) do not have the following structure:

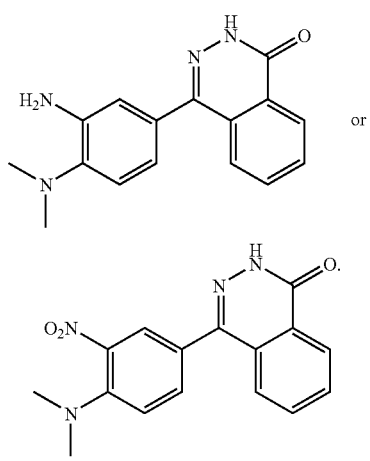
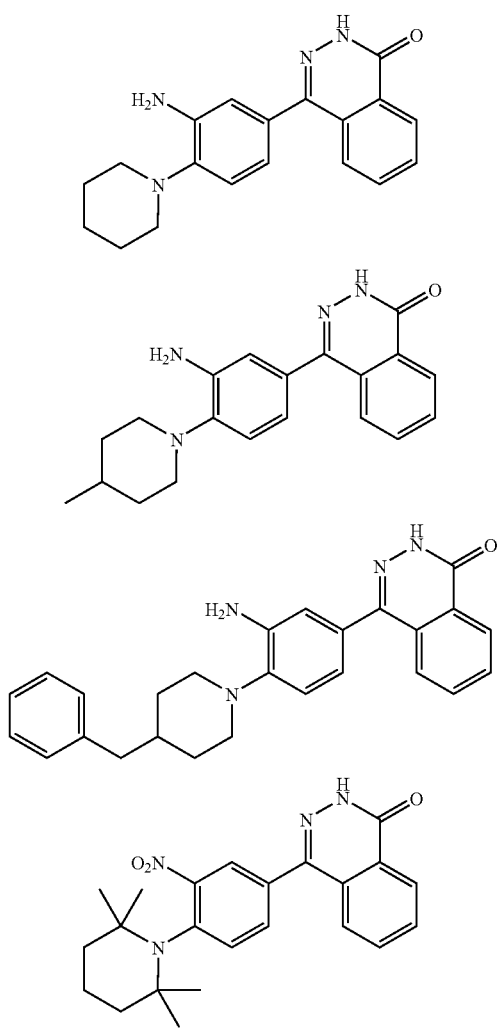
Non-limiting examples of compounds of Formula (II) wherein the —NR²R³ moiety forms a ring, optionally further substituted, include the following compounds:
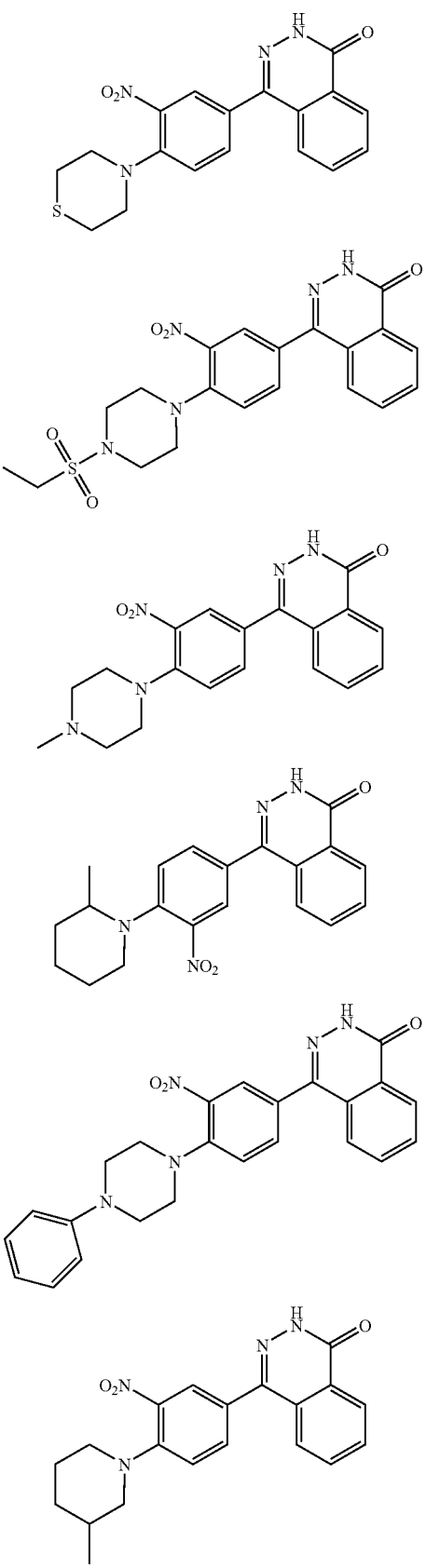

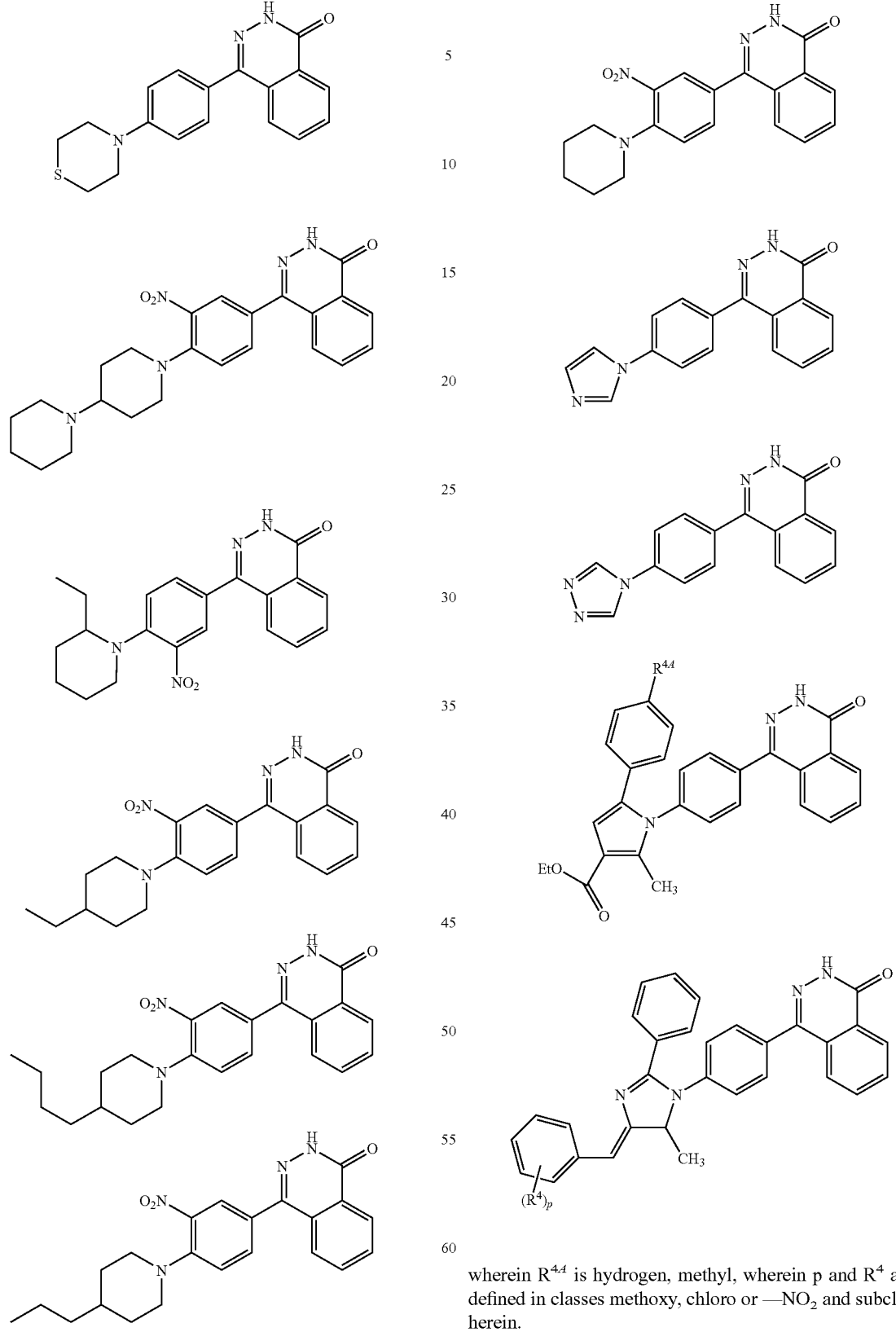
wherein $R^{4A}$ is hydrogen, methyl, wherein p and $R^4$ are as defined in classes methoxy, chloro or —$NO_2$ and subclasses herein.
In certain embodiments, compounds of Formula (II) exclude the following compounds:
In certain embodiments, compounds of Formula (II) exclude the following compounds, whose compositions and uses are embraced in the present invention:

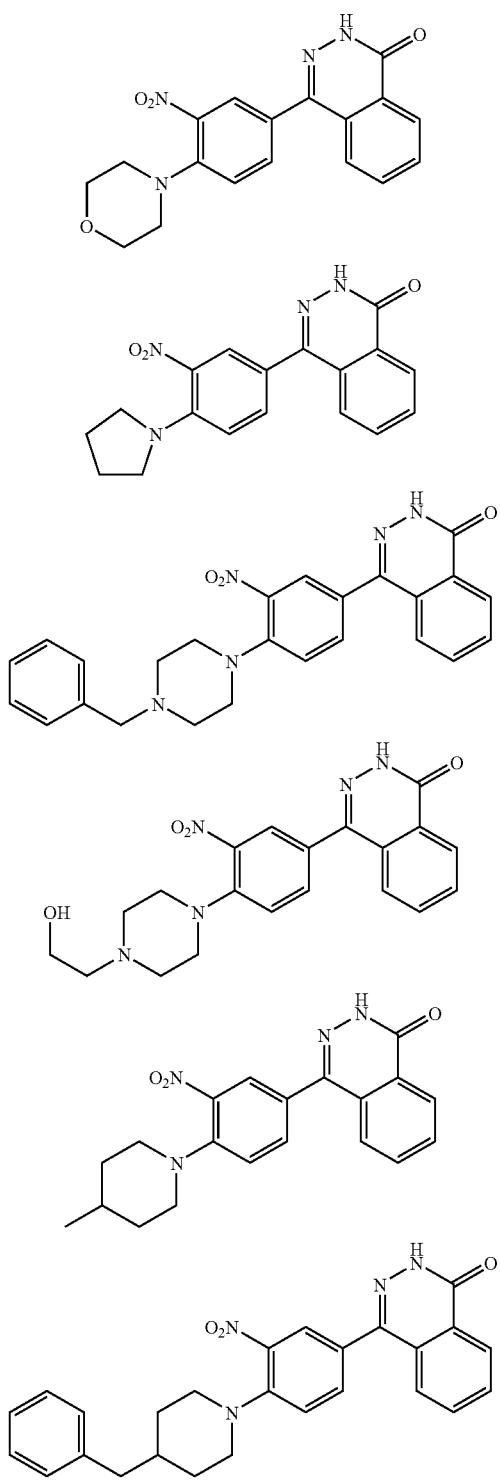

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

As discussed above, this invention provides novel compounds with a range of biological properties. Preferred compounds of this invention have biological activities relevant for the treatment of diseases, conditions or disorders where increase of HGF/SF activity would be beneficial.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. Certain compounds of the present invention are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated bygone of ordinary skill in the art that the synthetic methods, as described herein, utilize a variety of protecting groups. It will be appreciated that the compounds, as described herein, may be substituted with any number of substituents or functional moieties.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

2) Pharmaceutical Compositions

As discussed above this invention provides compounds that have biological properties useful for the treatment of any of a number of conditions or diseases in which cytokines such as but not limited to HGF/SF, EGF, VEGF or NGF, or the activities thereof, have a therapeutically useful role.

Accordingly, in another aspect of the present invention, pharmaceutical compositions are provided, which comprise any one or more of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an approved agent to treat the same or related indication, or it may be any one of a number of agents undergoing approval in the Food and Drug Administration that ultimately obtain approval for the treatment of any disorder related to HGF/SF activity. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a compound of this invention which upon administration to a patient in need is capable of providing, directly or indirectly, a compound as otherwise described herein, or a metabolite or residue thereof.

In one aspect, the invention is directed to compositions including pharmaceutical compositions comprising at least one compound of Formula (I).

In yet another embodiment, the invention is directed to compositions including pharmaceutical compositions comprising compounds of Formula (II). In certain embodiments, compositions comprising the following compounds are excluded:

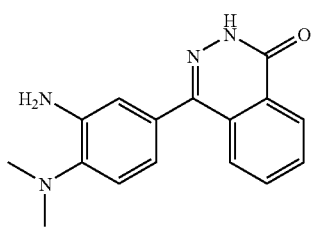

and

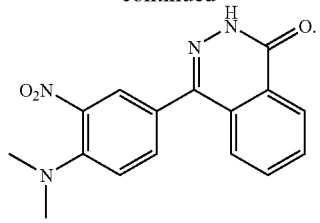

In yet another embodiment, the invention is directed to compositions including pharmaceutical compositions comprising compounds of Formula (II$^4$). In certain embodiments, compositions comprising the following compounds are excluded:

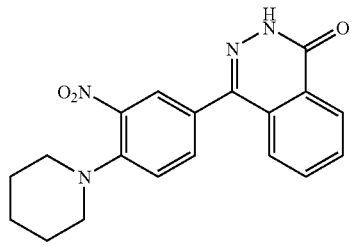

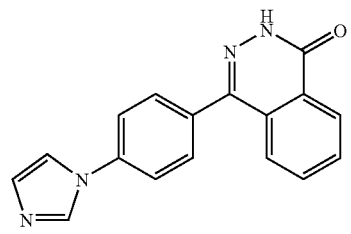

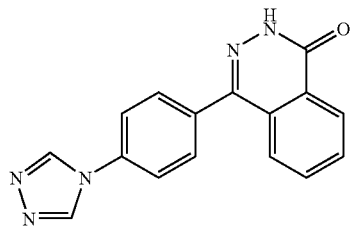

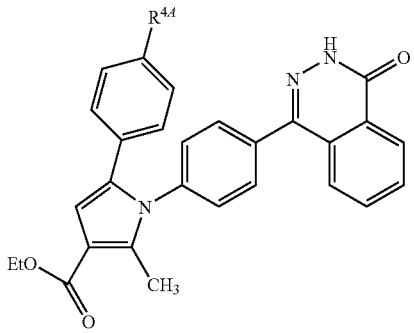

wherein R$^{44}$ s hydrogen, methyl, methoxy, chloro or ——NO$_2$

-continued

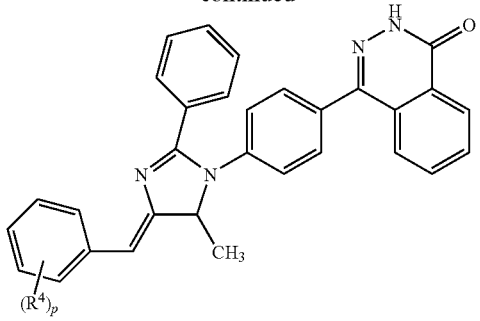

wherein p and R⁴ are as defined in classes and subclasses herein.

In yet another embodiment, the invention is directed to compositions including pharmaceutical compositions comprising compounds of Formula (II$^B$). In certain embodiments, compositions comprising the following compound are excluded:

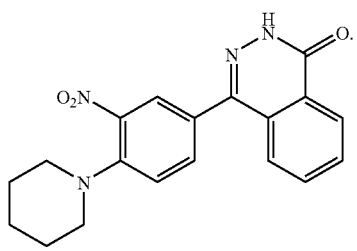

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood, or N-demethylation of a compound of the invention. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc;

excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut (peanut), corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methyl pyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Formulations for intraocular administration are also included. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with an anti-inflammatory agent), or they may achieve different effects (e.g., control of any adverse effects). In non-limiting examples, one or more compounds of the invention may be formulated with at least one cytokine, growth factor or other biological, such as an interferon, e.g., alpha interferon, or with at least another small molecule compound. Non-limiting examples of pharmaceutical agents that may be combined therapeutically with compounds of the invention include: antivirals and antifibrotics such as interferon alpha, combination of interferon alpha and ribavirin, Lamivudine, Adefovir dipivoxil and interferon gamma; anticoagulants such as heparin and warfarin; antiplatelets e.g., aspirin, ticlopidine and clopidogrel; other growth factors involved in regeneration, e.g., VEGF and FGF and mimetics of these growth factors; antiapoptotic agents; and motility and morphogenic agents.

In certain embodiments, the pharmaceutical compositions of the present invention further comprise one or more additional therapeutically active ingredients (e.g., anti-inflammatory and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and antisickness drugs.

3) Research Uses, Clinical Uses, Pharmaceutical Uses and Methods of Treatment

Research Uses

According to the present invention, the inventive compounds may be assayed in any of the available assays known in the art for identifying compounds having the ability to (1) induce endothelial cell growth and angiogenesis, (2) induce proliferation of other cells such as epithelial cells, neuronal cells, Schwann cells, and oligodendrocyte cells, (3) induce axonal growth, (4) induce myelin production, (5) inhibit apoptosis, (6) reduce fibrosis, (7) activate HGF signaling pathways, or (8) exhibit some or all of these activities. For example, the assay may be cellular or non-cellular, in vivo or in vitro, high- or low-throughput format, etc.

Thus, in one aspect, compounds of this invention which are of particular interest include those with HGF/SF-like activity, which: exhibit HGF/SF activity; exhibit the ability to mimic or agonize HGF/SF activities or the HGF/SF receptor c-met; stimulate cell proliferation, and in particular endothelial cell proliferation; exhibit angiogenic activity, the promotion of formation of new blood vessels; induce oligodendrocyte cell proliferation and axonal growth; induce myelin production; protect against apoptosis; and reduce fibrosis. In another aspect, compounds of this invention which are of particular interest include those with activities that mimic other cytokines, including but not limited to EGF, VEGF, and NGF, activate their receptors, activate the signaling pathways of their receptors, and exhibit various biological activities.

Clinical Uses of the Compounds of the Invention

In yet other aspects, the invention provides methods for using a compound of Formula (I) or a composition comprising a compound of Formula (I) for the prophylaxis or treatment of conditions and diseases in which promoting or mimicking the activity of cytokines is desired, or biological activities resulting from activating, agonizing or inducing phosphorylation of c-met or other receptor tyrosine kinases. In a preferred embodiment, the activity is inducing endothelial cell proliferation or angiogenesis. In another embodiment, the activity is to induce proliferation of other cells, such as epithelial cells, neuronal cells, Schwann cells, or oligodendrocyte cells. In a further embodiment, the activity is to induce growth of neuronal axons. In yet another embodiment, the activity is induction of myelin production. In yet another embodiment, the activity is protection against apoptosis. In yet another embodiment, the activity is anti-fibrotic. The compounds described herein are useful in the treatment of conditions and diseases where inducing endothelial cell proliferation or therapeutic angiogenesis is beneficial, where inducing proliferation of cells such as epithelial cells, neuronal cells, Schwann cells, and oligodendrocyte cells is beneficial, where inducing axonal growth is beneficial, where induction of myelin production is beneficial, where protection against apoptosis is beneficial, where anti-fibrosis is beneficial, or where all or some of the foregoing activities are beneficial, including but not limited to fibrotic liver disease, hepatic ischemia-reperfusion injury, cerebral infarction, ischemic heart disease, renal disease or lung (pulmonary) fibrosis, multiple sclerosis or various neurodegenerative diseases. In certain embodiments, the method is useful for treating a disease or condition, or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; other cardiovascular diseases; diabetes; renal failure; renal fibrosis or idiopathic pulmonary fibrosis; multiple sclerosis; and neurodegenerative diseases such as but not limited to metachromatic leukodystrophy, Refsum's disease, adrenoleukodystrophy, Krabbe's disease, phenylketonuria, Canavan disease, Pelizaeus-Merzbacher disease and Alexander's disease. In certain exemplary embodiments, the method is for the treatment of wounds for acceleration of healing; promoting vascularization of a damaged and/or ischemic organ, transplant or graft; amelioration of ischemia/reperfusion injury in the brain, heart, liver, kidney, or other tissues or organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus. Use of the compound is also provided for prophylaxis or preventing the occurrence of the diseases in subjects, and in particular subjects susceptible to of exhibiting risk factors for, the aforementioned diseases and conditions. Common among the foregoing conditions is benefit therein by promoting endothelial cell growth, angiogenesis or formation of new blood vessels. Moreover, the compounds of the invention are beneficial in providing biological activities resulting from activating, agonizing, phosphorylating, or in any other way activating the signaling pathway of the HGF/SF receptor, c-met, or other receptor tyrosine kinases.

In yet other aspects, the invention provides methods for using a compound of Formula (II) or a composition comprising a compound of Formula (II) for the prophylaxis or treatment of conditions and diseases in which promoting or mimicking the activity of cytokines is desired, or biological activities resulting from activating, agonizing or inducing phosphorylation of c-met or other receptor tyrosine kinases. In a preferred embodiment, the activity is inducing endothelial cell proliferation or angiogenesis. In another embodiment, the activity is to induce proliferation of other cells, such as epithelial cells, neuronal cells, Schwann cells, or oligodendrocyte cells. In a further embodiment, the activity is to induce growth of neuronal axons. In yet another embodiment, the activity is induction of myelin production. In yet another embodiment, the activity is protection against apoptosis. In yet another embodiment, the activity is anti-fibrotic. The compounds described herein are useful in the treatment of conditions and diseases where inducing endothelial cell proliferation or therapeutic angiogenesis is beneficial, where inducing proliferation of cells such as epithelial cells, neuronal cells, Schwann cells, and oligodendrocyte cells is beneficial, where inducing axonal growth is beneficial, where induction of myelin production is beneficial, where protection against apoptosis is beneficial, where anti-fibrosis is beneficial, or where all or some of the foregoing activities are beneficial, including but not limited to fibrotic liver disease, hepatic ischemia-reperfusion injury, cerebral infarction, ischemic heart disease, renal disease or lung (pulmonary) fibrosis, multiple sclerosis or various neurodegenerative diseases. In certain embodiments, the method is useful for treating a disease or condition, or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; other cardiovascular diseases; diabetes; renal failure; renal fibrosis or idiopathic pulmonary fibrosis; multiple sclerosis; and neurodegenerative diseases such as but not limited to metachromatic leukodystrophy, Refsum's disease, adrenoleukodystrophy, Krabbe's disease, phenylketonuria, Canavan disease, Pelizaeus-Merzbacher disease and Alexander's disease. In certain exemplary embodiments, the method is for the treatment of wounds for acceleration of healing; promoting vascularization of a damaged and/or ischemic organ, transplant or graft; amelioration of ischemia/reperfusion injury in the brain, heart, liver, kidney, or other tissues or organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus. Use of the compound is also provided for prophylaxis or preventing the occurrence of the diseases in subjects, and in particular subjects susceptible to of exhibiting risk factors for, the aforementioned diseases and conditions. Common among the foregoing conditions is benefit therein by promoting endothelial cell growth, angiogenesis or formation of new blood vessels. Moreover, the compounds of the invention are beneficial in providing biological activities resulting from activating, agonizing, phosphorylating, or in any other way activating the signaling pathway of the HGF/SF receptor, c-met, or other receptor tyrosine kinases.

1. Fibrotic Liver Disease: Liver fibrosis is the scarring response of the liver to chronic liver injury; when fibrosis progresses to cirrhosis, morbid complications can develop. In fact, end-stage liver fibrosis or cirrhosis is the seventh leading cause of death in the United States, and afflicts hundreds of millions of people worldwide; deaths from end-stage liver disease in the United States are expected to triple over the next 10-15 years, mainly due to the hepatitis C epidemic1. In addition to the hepatitis C virus, many other forms of chronic liver injury also lead to end-stage liver disease and cirrhosis, including other viruses such as hepatitis B and delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency).

Treatment of liver fibrosis has focused to date on eliminating the primary injury. For extrahepatic obstructions, biliary decompression is the recommended mode of treatment whereas patients with Wilson's disease are treated with zinc acetate. In chronic hepatitis C infection, interferon has been used as antiviral therapies with limited response: ~20% when used alone or ~50% response when used in combination with ribavirin. In addition to the low-level of response, treatment with interferon with or without ribavirin is associated with numerous severe side effects including neutropenia, thrombocytopenia, anemia, depression, generalized fatigue and flu-like symptoms, which are sufficiently significant to necessitate cessation of therapy. Treatments for other chronic liver diseases such as hepatitis B, autoimmune hepatitis and Wilson's disease are also associated with many side effects, while primary biliary cirrhosis, primary sclerosing cholangitis and non-alcoholic fatty liver disease have no effective treatment other than liver transplantation.

The advantage of treating fibrosis rather than only the underlying etiology, is that antifibrotic therapies should be broadly applicable across the full spectrum of chronic liver diseases. While transplantation is currently the most effective cure for liver fibrosis, mounting evidence indicates that not only fibrosis, but even cirrhosis is reversible. Unfortunately patients often present with advanced stages of fibrosis and cirrhosis, when many therapies such as antivirals can no longer be safely used due to their side effect profile. Such patients would benefit enormously from effective antifibrotic therapy, because attenuating or reversing fibrosis may prevent many late stage complications such as infection, ascites, and loss of liver function and preclude the need for liver transplantation. The compounds of the invention are beneficial for the treatment of the foregoing conditions, and generally are angiogenic and stimulate endothelial cell proliferation in this and other organ or tissues.

2. Hepatic Ischemia-Reperfusion Injury: Currently, transplantation is the most effective therapeutic strategy for liver fibrosis. However, in spite of the significant improvement in clinical outcome during the last decade, liver dysfunction or failure is still a significant clinical problem after transplantation surgery. Ischemia-reperfusion (IR) injury to the liver is a major alloantigen-independent component affecting transplantation outcome, causing up to 10% of early organ failure, and leading to the higher incidence of both acute and chronic rejection. Furthermore, given the dramatic organ shortage for transplantation, surgeons are forced to consider cadaveric or steatotic grafts or other marginal livers, which have a higher susceptibility to reperfusion injury. In addition to transplantation surgery, liver IR injury is manifested in clinical situations such as tissue resections (Pringle maneuver), and hemorrhagic shock.

The damage to the postischemic liver represents a continuum of processes that culminate in hepatocellular injury. Ischemia activates Kupffer cells, which are the main sources of vascular reactive oxygen species (ROS) formation during the initial reperfusion period. In addition to Kupffer cell-induced oxidant stress, with increasing length of the ischemic episode, intracellular generation of ROS by xanthine oxidase and in particular mitochondria may also contribute to liver dysfunction and cell injury during reperfusion. Endogenous antioxidant compounds, such as superoxide dismutase, catalase, glutathione, alphatocopherol, and beta-carotene, may all limit the effects of oxidant injury but these systems can quickly become overwhelmed by large quantities of ROS. Work by Lemasters and colleagues, has indicated that in addition to formation of ROS, intracellular calcium dyshomeostasis is a key contributor to liver IR injury. Cell death of hepatocytes and endothelial cells in this setting is characterized by swelling of cells and their organelles, release of cell contents, eosinophilia, karyolysis, and induction of inflammation, characteristic of oncotic necrosis. More recent reports indicate that liver cells also die by apoptosis, which is morphologically characterized by cell shrinkage, formation of apoptotic bodies with intact cell organelles and absence of an inflammatory response.

Indeed, minimizing the adverse effects of IR injury could significantly increase the number of patients that may successfully undergo liver transplantation. Pharmacologic interventions that reduce cell death and/or enhance organ regeneration represent a therapeutic approach to improve clinical outcome in liver transplantation, liver surgery with vascular exclusion and trauma and can therefore reduce recipient/patient morbidity and mortality. The compounds of the invention are beneficial for the treatment of the foregoing conditions.

3. Cerebral Infarction. Stroke and cerebrovascular disease are a leading cause of morbidity and mortality in the US: at least 600,000 Americans develop strokes each year, and about 160,000 of these are fatal. Research on the pathophysiological basis of stroke has produced new paradigms for prevention and treatment, but translation of these approaches into improved clinical outcomes has proved to be painfully slow. Preventive strategies focus primarily on reducing or controlling risk factors such as diabetes, hypertension, cardiovascular disease, and lifestyle; in patients with severe stenosis, carotid endarterectomy may be indicated. Cerebral angioplasty is used investigationally, but the high restenosis rates observed following coronary angioplasty suggest this approach may pose unacceptable risk for many patients. Therapeutic strategies focus primarily on acute treatment to reduce injury in the ischemic penumbra, the region of reversibly damaged tissue surrounding an infarct. Thrombolytic therapy has been shown to improve perfusion to the ischemic penumbra, but it must be administered within three hours of the onset of infarction. Several neuroprotective agents that block specific tissue responses to ischemia are promising, but none have yet been approved for clinical use. While these therapeutic approaches limit damage in the ischemic penumbra, they do not address the underlying problem of inadequate blood supply due to occluded arteries. An alternative strategy is to induce formation of collateral blood vessels in the ischemic region; this occurs naturally in chronic ischemic conditions, but stimulation of vascularization via therapeutic angiogenesis has potential therapeutic benefit.

Recent advances in imaging have confirmed the pathophysiological basis of the clinical observations of evolving stroke. Analysis of impaired cerebral blood flow (CBF) in the region of an arterial occlusion supports the hypothesis that a central region of very low CBF, the ischemic core, is irreversibly damaged, but damage in surrounding or intermixed zones where CBF is of less severely reduced, the ischemic penumbra, can be limited by timely reperfusion. Plate recently reviewed the evidence suggesting that therapeutic angiogenesis may be useful for treatment or prevention of stroke. First, analysis of cerebral vasculature in stroke patients showed a strong correlation between blood vessel density and survival and a higher density of microvessels in the ischemic hemisphere compared to the contralateral region. Second, studies in experimental models of cerebral ischemia indicate expression of angiogenic growth factors such as vascular endothelial growth factor (VEGF) or HGF/SF is induced rapidly in ischemic brain tissue. Third, administration of VEGF or HGF/SF can reduce neuronal damage and infarct volume in animal models. Similar evidence provided the rationale for developing therapeutic angiogenesis for treating peripheral and myocardial ischemia, which has been shown to produce clinical improvements in early studies in humans. The compounds of the invention are beneficial for the treatment of the foregoing conditions.

4. Ischemic heart disease is a leading cause of morbidity and mortality in the US, afflicting millions of Americans each year at a cost expected to exceed $300 billion/year. Numerous pharmacological and interventional approaches are being developed to improve treatment of ischemic heart disease including reduction of modifiable risk factors, improved revascularization procedures, and therapies to halt progression and/or induce regression of atherosclerosis. One of the most exciting areas of research for the treatment of myocardial ischemia is therapeutic angiogenesis. Recent studies support the concept that administration of angiogenic growth factors, either by gene transfer or as a recombinant protein, augments nutrient perfusion through neovascularization. The newly developed, supplemental collateral blood vessels constitute endogenous bypass conduits around occluded native arteries, improving perfusion to ischemic tissue. Some of the best-studied cytokines with angiogenic activity are vascular endothelial growth factor (VEGF), basic fibroblast growth factor (bFGF) and hepatocyte growth factor/scatter factor (HGF/SF). The compounds of the invention are beneficial for the treatment of the foregoing conditions.

Furthermore, advantage may be taken of the antifibrotic activities of the compounds of the invention in the area of heart disease by incorporating compounds in or on indwelling devices such as stents inserted into coronary arteries to maintain patency as part of an angioplasty procedure. Such devices can be coated with a controlled release formulation of one or more compounds of the invention, optionally including other agents, to prevent or impede fibrosis of the device and restenosis of the artery. The anti-fibrotic activity of the inventive compounds may likewise be used analogously-in or on devices used elsewhere in the body.

5. Renal Disease. Chronic renal dysfunction is a progressive, degenerative disorder that ultimately results in acute renal failure and requires dialysis as an intervention, and renal transplantation as the only potential cure. Initiating conditions of renal dysfunction include ischemia, diabetes, underlying cardiovascular disease, or renal toxicity associated with certain chemotherapeutics, antibiotics, and radiocontrast agents. Most end-stage pathological changes include extensive fibrinogenesis, epithelial atrophy, and inflammatory cell infiltration into the kidneys.

Acute renal failure is often a complication of diseases including diabetes or renal ischemia, procedures such as heminephrectomy, or as a side effect of therapeutics administered to treat disease. The widely prescribed anti-tumor drug cis-diamminedichloroplatinum (cisplatin), for example, has side effects that include a high incidence of nephrotoxicity and renal dysfunction, mainly in the form of renal tubular damage that leads to impaired glomerular filtration. Administration of gentamicin, an aminoglycoside antibiotic, or cyclosporin A, a potent immunosuppressive compound, causes similar nephrotoxicity. The serious side effects of these effective drugs restrict their use. The development of agents that protect renal function and enhance renal regeneration after administration of nephrotoxic drugs will be of substantial benefit to numerous patients, especially those with malignant tumors, and may allow the maximal therapeutic potentials of these drugs to be realized. The compounds of the invention are beneficial for the treatment of the renal diseases mentioned above.

6. Lung (Pulmonary) Fibrosis. Idiopathic pulmonary fibrosis (IPF) accounts for a majority of chronic interstitial lung diseases, and has an estimated incidence rate of 10.7 cases for 100,000 per year, with an estimated mortality of 50-70%. IPF is characterized by an abnormal deposition of collagen in the lung with an unknown etiology. Although the precise sequence of the pathogenic sequelae is unknown, disease progression involves epithelial injury and activation, formation of distinctive subepithelial fibroblast/myofibroblast foci, and excessive extracellular matrix accumulation. The development of this pathological process is preceded by an inflammatory response, often dominated by macrophages and lymphocytes, which is mediated by the local release of chemoattractant factors and upregulation of cell-surface adhesion molecules. Lung injury leads to vasodilatation and leakage of plasma proteins into interstitial and alveolar spaces, as well as activation of the coagulation cascade and deposition of fibrin. Fibroblasts migrate into this provisional fibrin matrix where they synthesize extracellular matrix molecules. In non-pathogenic conditions, excess fibrin is usually degraded by plasmin, a proteinase that also has a role in the activation of matrix metalloproteinases (MMPs). Activated MMPs degrade extracellular matrix and participate in fibrin removal, resulting in the clearance of the alveolar spaces and the ultimate restoration of injured tissues. In pathological conditions, however, these processes can lead to progressive and irreversible changes in lung architecture, resulting in progressive respiratory insufficiency and an almost universally terminal outcome in a relatively short period of time. Fibrosis is the final common pathway of a variety of lung disorders, and in this context, the diagnosis of pulmonary fibrosis implies the recognition of an advanced stage in the evolution of a complex process of abnormal repair. While many studies have focused on inflammatory mechanisms for initiating the fibrotic response, the synthesis and degradation the extracellular matrix represent the central event of the disease. It is this process that presents a very attractive site of therapeutic intervention.

The course of IPF is characterized by progressive respiratory insufficiency, leading to death within 3 to 8 years from the onset of symptoms. Management of interstitial lung disease in general, and in particular idiopathic pulmonary fibrosis, is difficult, unpredictable and unsatisfactory. Attempts have been made to use antiinflammatory therapy to reverse inflammation, relief, stop disease progression and prolong survival. Corticosteroids are the most frequently used antiinflammatory agents and have been the mainstay of therapy for IPF for more than four decades, but the efficacy of this approach is unproven, and toxicities are substantial. No studies have compared differing dosages or duration of corticosteroid treatment in matched patients. Interpretation of therapy efficacy is obscured by several factors including heterogeneous patient populations, inclusion of patients with histologic entities other than usual interstitial pneumonia, lack of objective, validated endpoints, and different criteria for "response." Cytotoxic drugs such as azathioprine and cyclophosphamide have also being used in combination with low dose oral corticosteroids. The results of such treatments vary from no improvement to significant prolongation of survival. Overall, currently available treatments for lung fibrosis are sub-optimal. Potential new therapies have emerged from the use of animal models of pulmonary fibrosis and recent advances in the cellular and molecular biology of inflammatory reactions. Such therapies involve the use of cytokines, oxidants and growth factors that are elaborated during the fibrotic reaction. Despite the use of newer strategies for treatment, the overall prognosis for patients with interstitial lung disease has had little quantifiable change, and the population survival remains unchanged for the last 30 years. Interferon gamma (IFN) may be effective in the treatment of IPF in some patients but its role is controversial. Literature indicated that IFN-gamma may be involved in small airway disease in silicotic lung. Others showed that IFN-gamma mediates bleomycin-induced pulmonary inflammation and fibrosis. Recently, hepatocyte growth factor (HGF), also known as scatter factor (SF) has emerged as an attractive target for the development of antifibrotic agents. The compounds of the invention are beneficial for the treatment of the foregoing condition, among other fibrotic diseases.

7. Spinal Cord Injury. It is estimated that the annual incidence of spinal cord injury (SCI), not including those who die at the scene of the accident, is approximately 11,000 new cases each year. The number of people in the United States who are alive in December 2003 who have SCI has been estimated to be approximately 243,000 persons. After initial injury, about half of those affected will remain completely paralyzed below the level of their spinal lesion. In the other half, the lesion is "incomplete" and some movement and/or sensation is preserved. Only 17% of those injured recover enough function to walk again. The higher up spinal cord lesion, the greater the involvement of paralysis and the greater mortality. Half of the surviving spinal cord injures are quadriplegic (paralysis of all four limbs) and half are paraplegic (paralysis of both legs). Compounds of the invention hold promise as a new approach to the clinical management of SCI, because they reduces neuronal cell death, promotes neuronal cell proliferation, scattering, axonal growth, and functional recovery after SCI.

8. Promotion of angiogenesis. Underlying the successful treatment of the aforementioned diseases is the induction of endothelial cell proliferation and formation of new blood vessels to restore vasculature in ischemic and fibrotic tissues. As noted above, recent studies support the concept that administration of angiogenic growth factors, either by gene transfer or as a recombinant protein, augments nutrient perfusion through neovascularization. The newly developed, supplemental collateral blood vessels constitute endogenous bypass conduits around occluded native arteries, improving perfusion to ischemic tissue. Some of the best-studied cytokines with angiogenic activity are vascular endothelial growth factor (VEGF), basic fibroblast growth factor (bFGF) and hepatocyte growth factor/scatter factor (HGF/SF). The compounds of the invention are beneficial for the treatment of the foregoing conditions.

9. Multiple Sclerosis. The most common of these is multiple sclerosis (MS), which usually manifests itself between the 20th and 50th years of life. Current estimates are that approximately 2.5 million people worldwide have MS, with between 250,000 and 350,000 cases in the United States, 50,000 cases in Canada, 130,000 cases in Germany, 85,000 cases in the United Kingdom, 75,000 cases in France, 50,000 cases in Italy, and 11,000 cases in Switzerland.

MS attacks the white matter of the central nervous system (CNS). In its classic manifestation (90% of all cases), it is characterized by alternating relapsing/remitting phases with periods of remission growing shorter over time. Its symptoms include any combination of spastic paraparesis, unsteady gait, diplopia, and incontinence. The compounds of the invention have utility in the treatment of MS.

10. Hereditary Neurodegenerative Disorders. This category includes the eight identified leukodystrophies: metachromatic leukodystrophy, Refsum's disease, adrenoleukodystrophy, Krabbe's disease, phenylketonuria, Canavan disease, Pelizaeus-Merzbacher disease and Alexander's disease. The first six are storage disorders. The lack or the malfunctioning of an enzyme causes a toxic buildup of chemical substances. In Pelizaeus-Merzbacher disease myelin is never formed (dysmyelination) because of a mutation in the gene that produces a basic protein of CNS myelin. The etiology of Alexander's disease remains largely unknown.

The clinical course of hereditary demyelinating disorders, which usually tend to manifest themselves in infancy or early childhood, is tragic. Previously normal children are deprived, in rapid progression, of sight, hearing, speech, and ambulation. Equally tragic is their prognosis: death within a few years.

11. Peripheral vascular disease. Peripheral vascular disease (PVD) is a nearly pandemic condition that has the potential to cause loss of limb, or even loss of life. PVD manifests as insufficient tissue perfusion caused by existing atherosclerosis that may be acutely compounded by either emboli or thrombi. Many people live daily with PVD; however, in settings such as acute limb ischemia, this pandemic disease can be life threatening and can require emergency intervention to minimize morbidity and mortality.

PVD, also known as arteriosclerosis obliterans, is primarily the result of atherosclerosis. The atheroma consists of a core of cholesterol joined to proteins with a fibrous intravascular covering. The atherosclerotic process gradually may progress to complete occlusion of medium and large arteries. The disease typically is segmental, with significant variation from patient to patient. Vascular disease may manifest acutely when thrombi, emboli, or acute trauma compromises perfusion. Thromboses are often of an atheromatous nature and occur in the lower extremities more frequently than in the upper extremities. Multiple factors predispose patients for thrombosis. These factors include sepsis, hypotension, low cardiac output, aneurysms, aortic dissection, bypass grafts, and underlying atherosclerotic narrowing of the arterial lumen.

The compounds of the invention have utility in treating PVD.

Exemplary Assays

Efficacy of the compounds of the invention on the aforementioned disorders and diseases or the potential to be of benefit for the prophylaxis or treatment thereof may be demonstrated in various studies, ranging from biochemical effects evaluated in vitro and effects on cells in culture, to in-vivo models of disease, wherein direct clinical manifestations of the disease can be observed and measured, or wherein early structural and/or functional events occur that are established to be involved in the initiation or progression of the disease. The positive effects of the compounds of the invention have been demonstrated in a variety of such assays and models, for a number of diseases and disorders. One skilled in the art can readily determine following the guidance described herein that a compound of the invention is a cytokine mimic and is useful therapeutically in the same manner as a cytokine.

1. In vitro Stimulation of Cell Proliferation, Myelin Production and Axonal Growth a. Stimulation of Cellular proliferation. The compounds of invention induce proliferation of human umbilical vein endothelial cells (HUVEC), monkey bronchial epithelial cells, neuronal cells, Schwann cells and oligodendrocytes as measured, for example, using the method of [$^3$H]-thymidine incorporation.

b. Stimulation of Axonal growth. Human cortical neuronal cells (HCN-2 from ATCC) are seeded in a flask in full medium (with 10% serum) and incubated for 24 hr. The medium is changed to one containing 1% serum and compounds are added. The cells are incubated with the compounds for 72 hr followed by observation of axonal growth.

c. Stimulation of Myelin production. Compounds of the invention induce myelin production by Schwann cells in vitro. Myelin production is assessed by staining with fluoromyelin.

2. Cellular Signaling a. Phosphorylation of receptors and signaling proteins. In human umbilical vein endothelial cells (HUVECs), monkey bronchial epithelial cells, MDCK cells, and Schwann cells, the compounds of the invention induce phosphorylation of c-met and other receptors. The assay is performed by Western blot analysis using antibodies specific to target proteins.

b. Intracellular signaling induced by compounds of the invention. In cells the compounds induce phosphorylation of extracellular receptor kinase (ERK), as determined by Western blot analysis.

3. Gene Expression a. Reduced Expression of Fibrotic markers. Compounds inhibit expression of alpha SMA in rat kidney fibroblasts.

4. Apoptosis.

a. Apoptosis in endothelial cells and other cells is induced by serum starvation, hydrogen peroxide, adriamycin, or ethanol when the cells are treated with the compounds. The extent of apoptosis and the protective effect by the compounds are measured by annexin V staining.

5. Angiogenesis a. Aortic ring assay. Thoracic artery rings from rats are embedded in Matrigel and grown for 5 days in the presence or absence of compounds of the invention. Treatment with compounds of the invention causes an increased outgrowth from the rings.

b. In vivo Matrigel assay. Matrigel mixed with a compound of the invention or vehicle is injected into the abdominal subcutaneous tissue of C57BL/6 mice. When harvested 10 days later, the compound is found to induce blood vessel formation into the Matrigel plugs, demonstrating that the compound can exert its angiogenic effects in vivo.

6. Effects on Cellular Migration

Assays demonstrate the following effects of the compounds of the invention on cellular migration:

a. Induction of Endothelial Cell Migration.

b. Increase Schwann Cell Migrationn c. Decrease Monocyte Migration

7. Hepatic Disease Models a. Antifibrotic Activity in Hepatic Stellate Cells. Serum starved (activated) LX2 cells (an immortalized human hepatic stellate cell line) that are treated with HGF/SF or a compound of the invention show a decrease in collagen I mRNA expression, as well as expression of other fibrotic marker genes, related to significant antifibrotic activity.

b. Liver Disease endpoints. The rat model of thioacetamide (TAA)-induced liver fibrosis and the rat bile duct ligation model of fibrosis showed improvements by the compounds of the invention, in a panel of functional and histological tests: gross morphology, mass, portal pressure, presence of ascites, enzymes (AST, ALT), collagen content, interstitial fibrosis and expression of fibrotic marker genes such as collagen 1, alpha-smooth muscle actin and MMP-2.

8. Protection Against Renal Dysfunction a. Clinical model: arterial occlusion. In a mouse model of transient unilateral renal artery occlusion, compounds of the invention are shown to restore function to injured kidneys.

b. Protection against $HgCl_2$-induced renal injury. In this model, mice are injected with a high dose of $HgCl_2$ and divided into treatment groups. Serum creatinine, BUN, and development of tubular necrosis are measured to indicate positive clinical activity.

c. Protection against ureteral obstruction. The effects of the compounds of invention on renal injury secondary to ureteral obstruction are examined in a mouse model of transient unilateral renal artery occlusion. Immunohistochemical staining is performed for fibronectin, proliferating cell nuclear antigen, and TUNEL (for an assessment of apoptosis). Trichrome staining is also performed to assess the extent of collagen formation as an indication of interstitial fibrosis.

d. Protection against Doxorubicin-induced Renal Fibrosis in Rats. Compounds of the invention attenuate renal dysfunction and reduce interstitial collagen accumulation in this model.

9. Cerebral Infarction/Stroke Model a. Neuroprotective Effects in Brain Tissue. Cerebral infarction was induced in rats by middle cerebral artery occlusion (MCAO) for 24 hr. Test compound or vehicle was administered i.p. Sections of the brain were then examined for cell death by staining with a tetrazolium compound. Normal rat brains exhibit a red staining due to TTC reduction whereas areas containing dead cells are white. The effect of inducing new vessel formation was determined by measuring blood flow using a laser Doppler imager.

10. Cardiovascular Disease Models a. Atherosclerosis in Apo E knock-out mice. Reduction in the extent of plaque and lipid content of vessels was observed, as well as a reduction in hair loss and skin lesions in this model.

b. Ischemia/reperfusion. Compounds of the invention have been shown effective in ischemia/reperfusion models, such as the isolated perfused heart model.

11. Transplantation and Organ Preservation

The viability of organs and tissues harvested and transported for transplant is currently optimally maintained by bathing and transport in storage solutions such as the University of Wisconsin (UW) cold storage solution (100 mM $KH_2PO_4$, 5 mM $MgSO_4$ 100 mM potassium lactobionate, 1 mM allopurinol, 3 mM glutathione, 5 mM adenosine, 30 mM raffinose, 50 g/liter of hydroxyethyl starch, 40 units/liter of insulin, 16 mg/liter of dexamethasone, 200,000 units/liter of penicillin, pH 7.4; 320-330 mOsM) (Ploeg R J, Goossens D, Vreugdenhil P, McAnulty J F, Southard J H, Belzer F O. Successful 72-hour cold storage kidney preservation with UW solution. Transplant Proc. Feb. 20, 1998; (1 Suppl 1):935-8.). To further enhance the viability of transplanted organs and tissues, inhibit apoptosis and promote vascularization thereof, one or more compounds of the invention can be included in this or any other storage solution, as well as perfused into the donor or donor organ prior to harvesting, and administered to the recipient systemically and/or locally into the transplanted organ or transplant site.

12. Lung Fibrosis Model a. Bleomycin-iduced lung injury. The effects of inventive compounds on pulmonary fibrosis can be assessed using a well-established mouse model of bleomycin-induced lung injury. The Ashcroft scale is used to obtain a numerical fibrotic score with each specimen being scored independently by two histopathologists, and the mean of their individual scores considered as the fibrotic score. In addition, reduction in lung hydroxyproline content was used to also assess efficacy of the compounds in reducing pulmonary fibrosis.

13. Diabetes Mellitus a. Hyperglycemia. The effect of the compounds of the invention on glycemia in streptozotocin induced diabetes was evaluated. Compounds of the invention reduced blood glucose levels.

14. Multiple Sclerosis and Neurodegenerative Diseases a. Effect on Schwann Cells. As noted above in section (1) above, compounds of the invention promote axonal growth. As will be shown in the examples below, compounds of the invention also increase myelin production thereby.

b. As noted above, compounds of the invention induce robust c-Met phosphorylation in Schwann cells.

c. Mouse model of multiple sclerosis. As is shown in the examples below, experimental autoimmune encephalomyelitis (EAE) was induced by immunization of female mice with MOG 35-55 emulsified in CFA containing 1 mg/ml M. tuberculosis. Drug administration started immediately after second injection of peptide. Disease severity was monitored in the blind scoring by two scientists and according to a standard scale. The result shows significant recovery effect from developing MS in this animal model.

15. Angiogenesis/Peripheral Ischemia Models a. Mouse and Rat hindlimb ischemia model. In a mouse hindlimb ischemia model treatment with a compound of the invention produces greater recovery of hindlimb blow flow (as measured by laser Doppler imaging). Improved flux is associated with an increased number of capillaries in the ischemic muscle. Similar findings are seen in a rat model.

b. Hindlimb ischemia in non-obese diabetic (NOD) mice. In female NOD mice subjected to hindlimb ischemia, hindlimb blood flow (measured using a Laser Doppler imager) demonstrates recovery by administration of a compound of the invention.

c. Angiogenesis in full-thickness cutaneous wounds. In full thickness cutaneous wounds in pigs significant increases are observed in capillary numbers after treatment with a compound of the invention.

As detailed in the exemplification herein, in assays to determine the ability of compounds to stimulate cell growth, myelin production, and axonal growth, induce angiogenesis, protect against apoptosis, and reduce fibrosis, certain inventive compounds exhibited ED50 values $\leq 50$ µM. In certain other embodiments, inventive compounds exhibit $ED_{50}$ values $\leq 40$ µM. In certain other embodiments, inventive compounds exhibit $ED_{50}$ values $\leq 30$ µM. In certain other embodiments, inventive compounds exhibit $ED_{50}$ values $\leq 20$ µM. In certain other embodiments, inventive compounds exhibit $ED_{50}$ values $\leq 10$ µM. In certain other embodiments, inventive compounds exhibit $ED_{50}$ values $\leq 7.5$ µM. In certain embodiments, inventive compounds exhibit $ED_{50}$ values $\leq 5$ µM. In certain other embodiments, inventive compounds exhibit $ED_{50}$ values $\leq 2.5$ µM. In certain embodiments, inventive compounds exhibit $ED_{50}$ values $\leq 1$ µM. In certain other embodiments, inventive compounds exhibit $ED_{50}$ values $\leq 750$ nM. In certain other embodiments, inventive compounds exhibit $ED_{50}$ values $\leq 500$ nM. In certain other embodiments, inventive compounds exhibit $ED_{50}$ values $\leq 250$ nM. In certain other embodiments, inventive compounds exhibit $ED_{50}$ values $\leq 100$ nM. In other embodiments, exemplary compounds exhibited $ED_{50}$ values $\leq 75$ nM. In other embodiments, exemplary compounds exhibited $ED_{50}$ values $\leq 50$ nM. In other embodiments, exemplary compounds exhibited $ED_{50}$ values $\leq 40$ nM. In other embodiments, exemplary compounds exhibited $ED_{50}$ values $\leq 30$ nM. In other embodiments, exemplary compounds exhibited $ED_{50}$ values $\leq 20$ nM. In other embodiments, exemplary compounds exhibited $ED_{50}$ values $\leq 10$ nM. In other embodiments, exemplary compounds exhibited $ED_{50}$ values $\leq 5$ nM.

Pharmaceutical Uses and Methods of Treatment

As discussed above, certain of the compounds as described herein induce endothelial cell proliferation or therapeutic angiogenesis, induce proliferation of cells such as epithelial cells, neuronal cells, Schwann cells, and oligodendrocyte cells, induce axonal growth, induce myelin production, protect cells against apoptosis, exhibit anti-fibrotic activity, or exhibit all or some of these activities. Thus, compounds of the invention are useful for the treatment of any condition, disease or disorder in which these beneficial activities would have a beneficial role. Accordingly, in another aspect of the invention, methods for the treatment of HGF/SF activity or other cytokine activity related disorders are provided comprising administering a therapeutically effective amount of a compound of the invention as described herein, to a subject in need thereof. In certain embodiments, a method for the treatment disorders related to these activities is provided comprising administering a therapeutically effective amount of an inventive compound, or a pharmaceutical composition comprising an inventive compound to a subject in need thereof, in such amounts and for such time as is necessary to achieve the desired result.

In certain embodiments, the method involves the administration of a therapeutically effective amount of the compound or a pharmaceutically acceptable derivative thereof to a subject (including, but not limited to a human or animal) in need of it. Subjects for which the benefits of the compounds of the invention are intended for administration include, in addition to humans, livestock, domesticated, zoo and companion animals.

As discussed above this invention provides novel compounds that have the beneficial activities In certain embodiments, the inventive compounds are useful for the treatment of wounds for acceleration of healing (wound healing may be accelerated by promoting cellular proliferation, particularly of vascular cells), normalization of myocardial perfusion as a consequence of chronic cardiac ischemia or myocardial infarction, development or augmentation of collateral vessel development after vascular occlusion or to ischemic tissues or organs, fibrotic diseases, hepatic disease including fibrosis and cirrhosis, lung fibrosis, renal failure, renal fibrosis, cerebral infarction (stroke), diabetes mellitus, and vascularization of grafted or transplanted tissues or organs. Renal conditions for which compounds of the invention may prove useful include: radiocontrast nephropathy; fibrosis secondary to renal obstruction; indication for renal trauma and transplantation; renal failure secondary to chronic diabetes and/or hypertension.

It will be appreciated that the compounds and compositions, according to the method of the present invention, may be administered using any amount-and any route of administration effective for the treatment of the conditions or diseases in which cytokines such as but not limited to HGF/SF, VEGF, EGF, or NGF, or the activities thereof have a therapeutically useful role. Thus, the expression "effective amount" as used herein, refers to a sufficient amount of agent to exhibit these activities modulate cytokine activity (e.g., mimic cytokine activity), and to exhibit a therapeutic effect. The exact amount required will vary from subject to subject, depending on the species, age, and general condition of the subject, the severity of the infection, the particular therapeutic agent, its mode and/or route of administration, and the like. The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, subcutaneously, intradermally, intra-ocularly, topically (as by powders, ointments, or drops), buccally, as an oral or nasal spray, or the like, depending on the severity of the disease or disorder being treated. In certain embodiments, the compounds of the invention may be administered at dosage levels of about 0.001 mg/kg to about 50 mg/kg, preferably from about 0.1 mg/kg to about 10 mg/kg for parenteral administration, or preferably from about 1 mg/kg to about 50 mg/kg, more preferably from about 10 mg/kg to about 50 mg/kg for oral administration, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Moreover, pharmaceutical compositions comprising one or more compounds of the invention may also contain other compounds or agents for which co-administration with the compound(s) of the invention is therapeutically advantageous. As many pharmaceutical agents are used in the treatment of the diseases and disorders for which the compounds of the invention are also beneficial, any may be formulated together for administration. Synergistic formulations are also embraced herein, where the combination of at least one compound of the invention and at least one other compounds act more beneficially than when each is given alone. Non-limiting examples of pharmaceutical agents that may be combined therapeutically with compounds of the invention include (non-limiting examples of diseases or conditions treated with such combination are indicated in parentheses): antivirals and antifibrotics, such as interferon alpha (hepatitis B, and hepatitis C), combination of interferon alpha and ribavirin (hepatitis C), Lamivudine (hepatitis B), Adefovir dipivoxil (hepatitis B), interferon gamma (idiopathic pulmonary fibrosis, liver fibrosis, and fibrosis in other organs); anticoagulants, e.g., heparin and warfarin (ischemic stroke); antiplatelets e.g., aspirin, ticlopidine and clopidogrel (ischemic stroke); other growth factors involved in regeneration, e.g., VEGF and FGF and mimetics of these growth factors; antiapoptotic agents; and motility and morphogenic agents.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of small molecule chemistry to draw upon, in combination with the information contained herein, for guidance on synthetic strategies, protecting groups, and other materials and methods useful for the synthesis of the compounds of this invention.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/ or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

1) Synthesis of Exemplary Compounds:

Compounds of Formula (I) and (II) of the invention can be prepared following the reaction schemes 1-4 shown below.

Preparation of 4-[3-nitro-4-(1-homopiperidinyl)phenyl]-1-(2H)-phthalazinone.

Step 1. Preparation of 2-(4'-chloro-3'-nitrobenzoyl)benzoic acid. As shown in Scheme 1 below, 2-(4-chlorobenzoyl) benzoic acid (80 g, 0.37 mol) was added to 98% sulphuric acid (210 ml) keeping the temperature below 10° C. A further volume of sulphuric acid (60 ml) was then added. The mixture was stirred for 2 hrs until complete solution. 90% Nitric acid (21 ml) was added to conc. sulphuric acid (50 ml) with cooling and stirring. The nitrating mixture was added to the benzoic acid solution dropwise keeping the temperature below 15° C. When the addition was complete the mixture was stirred at 5-10C. for 1 hr, the mixture was then poured onto crushed ice (2.5l) and the ice allowed to melt. The resulting white solid was filtered, washed with water (1.5 l) and dried. Yield 92.7 g (98%). The combined products from 2 runs of the above reaction were recrystallized by stirring in ethyl acetate (1.5l) at 70° C. and adding IMS (~90 ml) to obtain a clear solution. Pentane (1.5l) was added to yield a white crystalline solid (142.3 g)

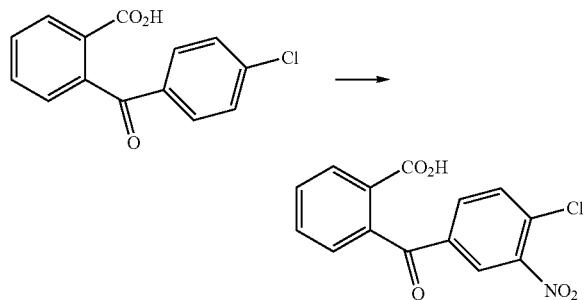

Scheme 1

Step 2. Preparation of 2-(4-(homopiperidin-1-yl)-3-nitrobenzoyl)benzoic acid (Scheme 2). To a solution of the 2-(4'-chloro-3'-nitrobenzoyl)benzoic acid (prepared in Step 1; 142 g, 0.465 mol) in acetonitrile (1400 ml) was added homopiperidine (138 g, 1.39 mol, 3 eq.). The mixture was heated to 80° C. for 4 hrs. The reaction mixture was then concentrated to ~500 ml and diluted with water to 2.5 l. The aqueous was made acidic with conc. HCl solution and extracted with a mixture of ether/ethyl acetate (1:1). This extract was separated from water, dried (MgSO$_4$), filtered and evaporated to dryness at reduced pressure to yield a viscous orange oil. This was triturated with a small volume of ether, then hexanes to yield a yellow solid.

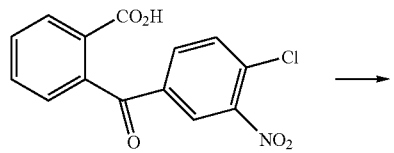

Scheme 2

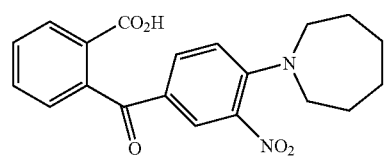

Step 3. Preparation of 4-[3-nitro-4-(1-homopiperidinyl) phenyl]-1-(2H)-phthalazinone (Scheme 3). To a suspension of 2-(4-(homopiperidin-1-yl)-3-nitrobenzoyl)benzoic acid (prepared in Step 2; 80 g, 0217 mol) in ethanol (450 ml) was added hydrazine hydrate (98%, 21.74 g, 0.435 mol, 2 eq.). After refluxing for 1.5 hrs, more hydrazine hydrate (8 ml) was added. It was refluxed for a further 2 hrs. The reaction mixture was cooled to ~15° C. and the orange crystals filtered, washed with IMS then ether before drying. The yield was 66.88 g (83.9%) Melting point 187-189° C.

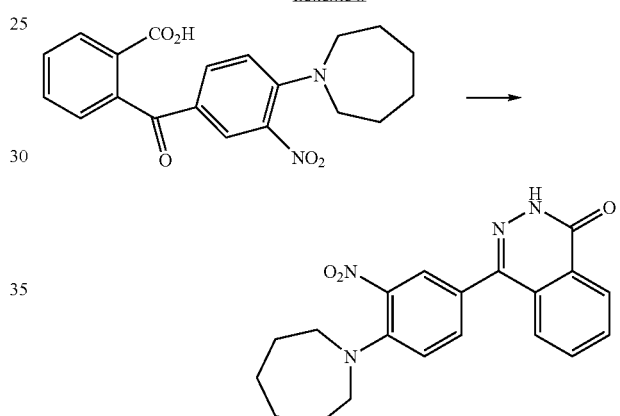

Scheme 3

As an example, compounds of Formula (I) and (II) where m is 1 and R$^1$ is nitro can be prepared in accordance with Scheme 4.

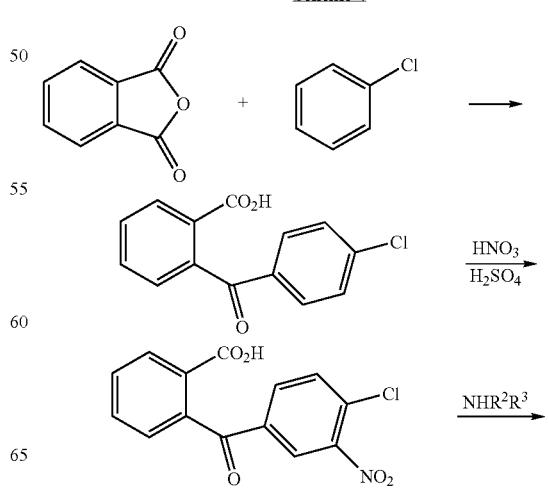

Scheme 4

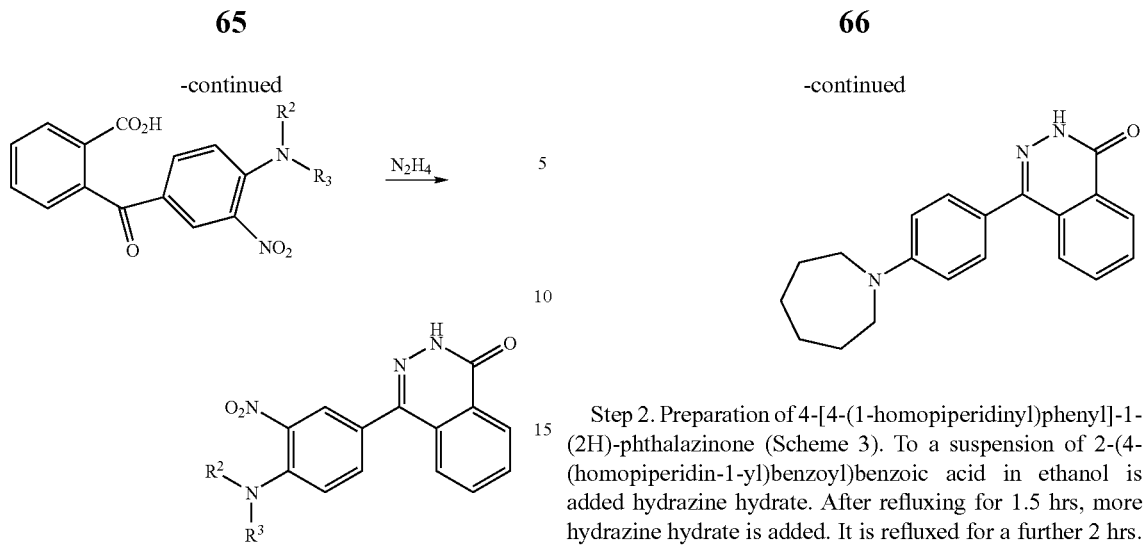

These compounds can be further derivatized to yield the corresponding amino derivatives (i.e., m=1 and $R^1$=$NH_2$).

Compounds of Formula (I) and (II) of the invention where $R^1$ is hydrogen can be prepared following the reaction scheme shown below.

Preparation of 4-[4-(1-homopiperidinyl)phenyl]-1-(2H)-phthalazinone.

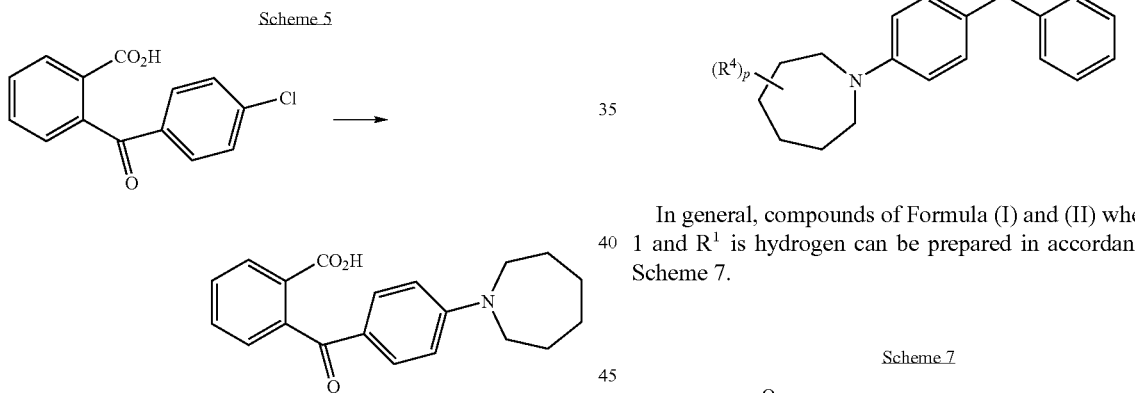

Step 1. Preparation of 2-(4-(homopiperidin-1-yl)benzoyl) benzoic acid (Scheme 1). To a solution of 2-(4'-chlorobenzoyl)benzoic acid in acetonitrile is added homopiperidine. The mixture is heated to 80° C. for 4 hrs. The reaction mixture is then concentrated and diluted with water. The aqueous is made acidic with conc. HCl solution and is extracted with a mixture of ether/ethyl acetate (1:1). This extract is separated from water, dried (MgSO$_4$), filtered and evaporated to dryness at reduced pressure to yield the product.

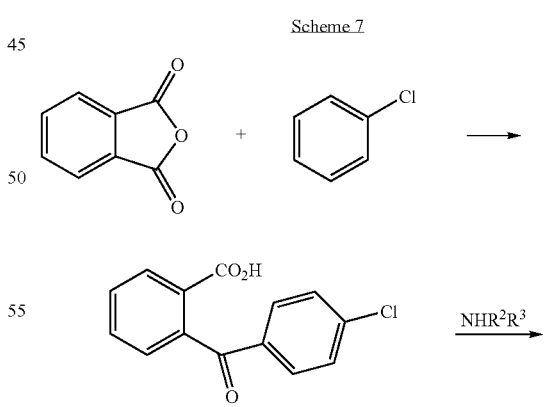

Step 2. Preparation of 4-[4-(1-homopiperidinyl)phenyl]-1-(2H)-phthalazinone (Scheme 3). To a suspension of 2-(4-(homopiperidin-1-yl)benzoyl)benzoic acid in ethanol is added hydrazine hydrate. After refluxing for 1.5 hrs, more hydrazine hydrate is added. It is refluxed for a further 2 hrs. The reaction mixture is cooled to ~15° C. and the product is filtered, washed with IMS then ether before drying.

It will be appreciated that the use of a substituted homopiperidine in Scheme 5 would lead to the preparation of corresponding substituted homopiperidinyl counterparts:

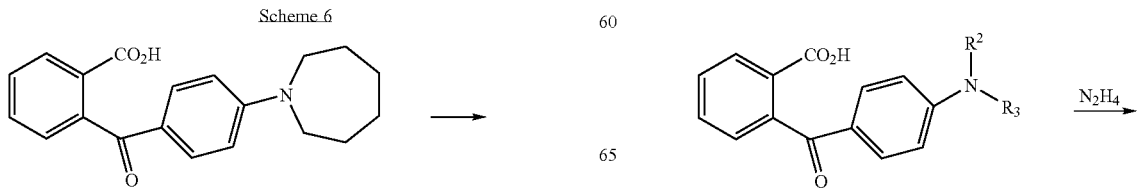

In general, compounds of Formula (I) and (II) where m is 1 and $R^1$ is hydrogen can be prepared in accordance with Scheme 7.

-continued

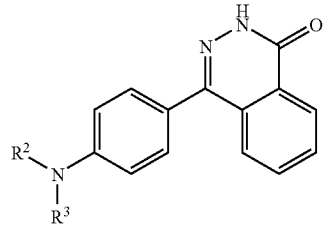

Non-limiting examples of R²R³NH reagents shown in Schemes 4 and 7 to produce compounds of the invention include: dimethylamine, diethylamine, dipropylamine, di-tert-butylamine, homopiperidine, 3-aminohomopiperidine, 2-methylhomopiperidine, 3-methylhomopiperidine, piperidine, 2-methylpiperidine, 3-methylpiperidine, diethylamine, 2,2,6,6,-tetramethylpiperidine, 4-benzylpiperidine, thiomorpholine, 4-methylpiperazine, 4-phenylpiperazine, 4-ethylsulfonylpiperazine, and pyrrolidone, etc.

Other compounds of Formula (I) and (II) of the invention can be prepared following the reaction scheme shown in Schemes 8 and 9 below.

Scheme 8

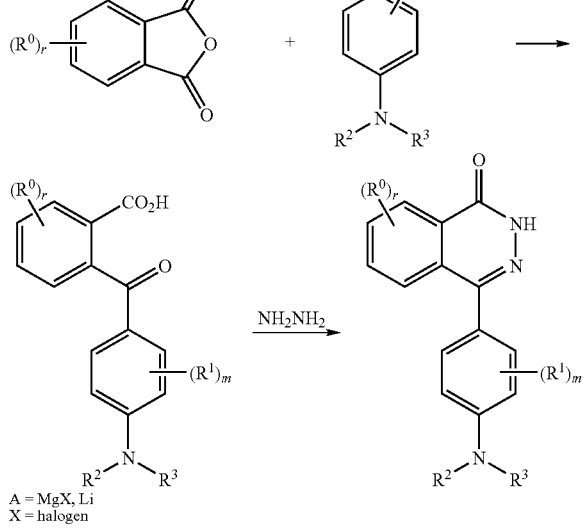

A = MgX, Li
X = halogen wherein r is 1-4 and $R^0$ take the definition of $R^1$.

Reaction of appropriately substituted phthalic anhydrides with aryl nucleophiles, such as Grignard reagents or aryl lithium species, would provide the 2-acylbenzoic acid intermediates. Treatment with hydrazine would afford ring closure to the desired phthalazinone analogues. Synthetic methods for such transformations are described in Yamaguchi, M. et al. *J. Med. Chem.* 1993, 36, 4052.

In cases where a nitro group is present, reduction of the nitro group using standard methods would provide the corresponding primary amine. Such amine could then be acylated using carboxylic acids/acyl halides, isocyanates, or isothiocyanates, to form amides, ureas, and thioureas, respectively.

Scheme 9

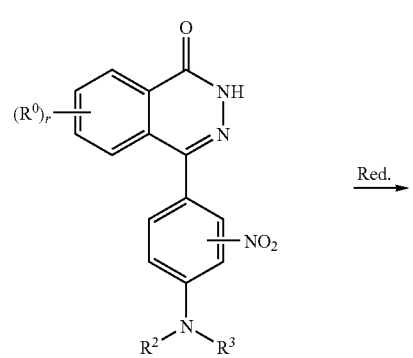

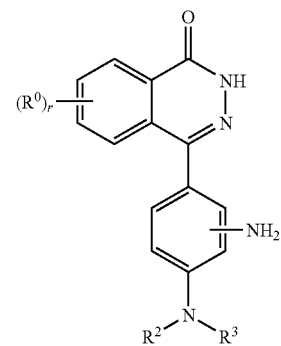

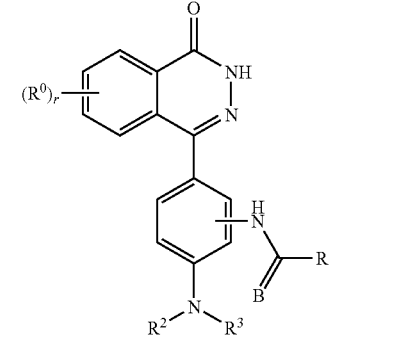

B = O, S
R = alkyl, aryl, NH-alkyl, NH-aryl, etc.

The foregoing schemes are merely exemplary of synthetic routes to the compound of the invention. They may be readily modified or varied to prepare the variety of compounds of the invention.

The invention encompasses compounds described herein substituted on the phthalazinone ring.

The foregoing compounds, compositions and methods of the invention are illustrated by the following examples, which are merely exemplary of aspects of the invention and are not limiting.

2) Biological Activity:

1. Compounds of the Invention Induce Endothelial Cell Proliferation and Migration:

a. Proliferation. The following assay was performed to assess the activity of the compounds of the invention in cell proliferation. Endothelial cells (HUVECs) were seeded in 96-well plates at a density of 10,000 cells per well in the normal growth medium (EGM-2-Clonetics) containing 2% fetal bovine serum, FGF, VEGF, IGF, ascorbic acid, EGF, GA, heparin and hydrocortisone. The cells were grown normally in the growth medium for 24 hr at 37° C. and 5% $CO_2$. The cells were then rinsed with RPMI-1% BSA and starved for 1-2 hr. The stock solutions of the compounds of the invention were made at a concentration of 10 mg/ml in DMSO and diluted in RPMI-1% BSA at final concentrations of 0.001 uM to 50 uM. The cells were then washed and treated with the compounds and incubated for another 20 hr at 37° C. Then $^3$H thymidine (0.5 microgram/ml in RPMI-BSA) was added to the cells and incubated at 37° C. for 4 hr. The unincorporated thymidine was removed by washing the cells four times with 1×PBS. Then the cells were lysed with 0.5M NaOH for 30 min and the radioactivity counted in the beta counter. A similar proliferation assay using monkey bronchial epithelial cells (4MBR-5) and oligodendrocyte cells was also employed.

As shown in FIG. 1A, compound of the invention induced a very large increase in HIVEC proliferation as measured by thymidine incorporation. Typically, compounds of the invention show an 8 to 20 fold increase in HUVEC proliferation over control, a magnitude not seen by HGF (shown in figure) or other molecules.

Dose response curves for three compounds of the invention are shown in FIGS. 1B-D, and show stimulated HUVEC (endothelial cell) proliferation at an $ED_{50}$ (effective dose giving 50% stimulation) of about 5-10 uM. Compounds also synergistically stimulated HUVEC proliferation together with HGF, FGF, EGF, and VEGF, which are angiogenic cytokines.

The following compounds induced proliferation of HUVEC and oligodendrocytes with the $ED_{50}$ shown in Tables 1 and 2, respectively:

TABLE 1

| Compound | HUVEC $ED_{50}$ |
|---|---|
| 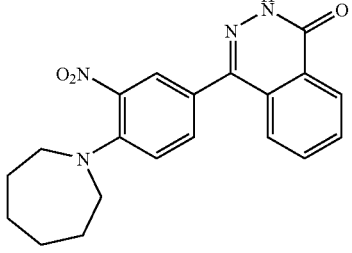 | 2.5 μM |
| 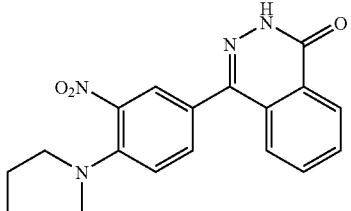 | 10 μM |
| 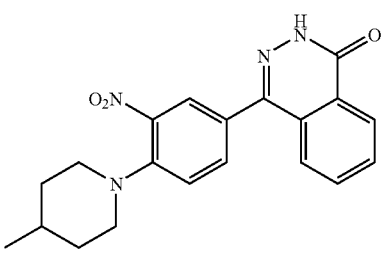 | 5 μM |

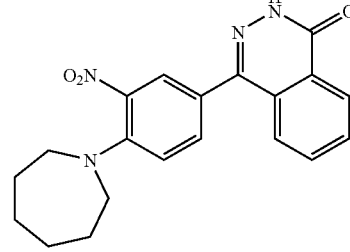

TABLE 1-continued

| Compound | HUVEC $ED_{50}$ |
|---|---|
|  | 2 μM |
|  | 3 μM |
|  | 4 μM |
|  | 3 μM |

TABLE 2

| Compound | Oligodendrocyte $ED_{50}$ |
|---|---|
|  | 0.2 μM |

TABLE 2-continued

| Compound | Oligodendrocyte ED$_{50}$ |
|---|---|
| (structure: 4-(3-nitro-4-piperidin-1-yl-phenyl)-phthalazin-1(2H)-one) | 0.2 µM |
| (structure: 4-(3-nitro-4-(4-methylpiperidin-1-yl)phenyl)-phthalazin-1(2H)-one) | 0.2 µM |

Figure 2:
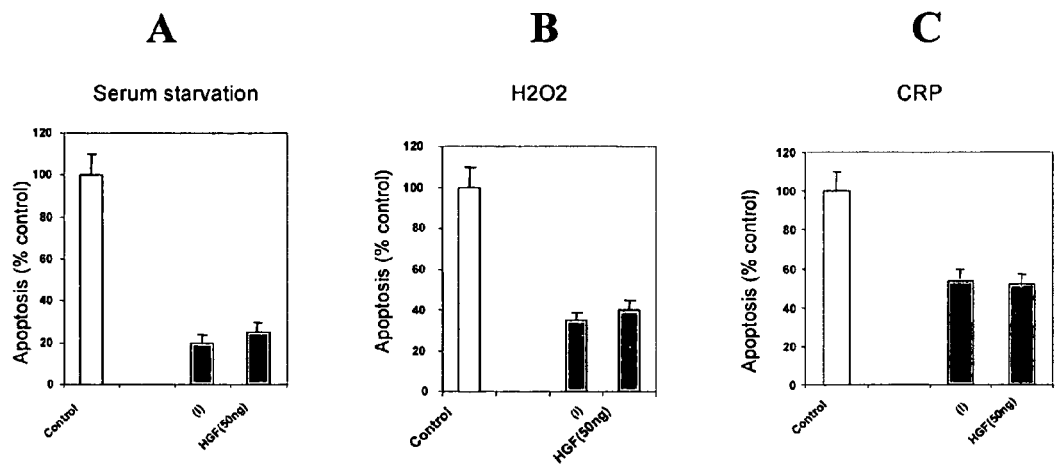
FIG. 2A-C show that a compound of the invention protects HUVEC from apoptosis induced by serum starvation (A), hydrogen peroxide (B) and CRP (C), respectively.

2. Compounds of the Invention Protect HUVEC Cells Against Apoptosis. Inventive compounds also protect HUVEC against apoptosis (programmed cell death) induced by serum starvation, hydrogen peroxide or CRP. Endothelial cell (EC) apoptosis is an initiating event in the pathogenesis of atherosclerosis. In fact, C-reactive protein (CRP, which is elevated in atherosclerotic patients, is known to induce endothelial apoptosis. It was determined whether compounds of the invention protect ECs against apoptosis induced by serum starvation, $H_2O_2$ (oxidative stress), or CRP. HUVECs (Cambrex, Calif.) were grown to 80% confluence in 6-well plates in complete serum medium. Cells were then washed with RPMI-1% BSA and treated with vehicle, compound (10 uM) or SF/HGF (50 ng/ml) and incubated for 24 hours. Apoptosis was induced by serum starvation or addition of $H_2O_2$ (100 uM) or addition of CRP (10 ug/ml). Apoptotic cells were identified using the Vybrant Assay Kit (Molecular Probes, Oreg.). As seen in FIGS. 2A, 2B and 2C, inventive compound attenuated apoptosis in ECs Induced by serum starvation, $H_2O_2$ and CRP, respectively.

3. Compounds of the Invention Activate HGF/SF Signaling Pathways.

Figure 3:
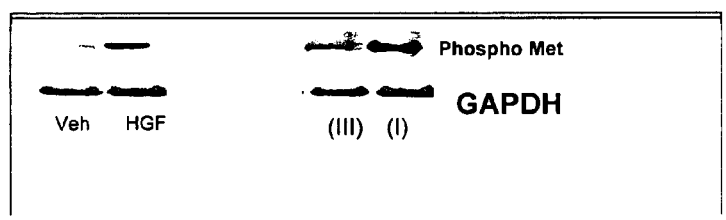
FIG. 3 shows that a compound of the invention increases phosphorylation of the HGF/SF receptor, c-met, in Schwann cells.

One possible mechanism of the activities of the compounds of the invention (which Applicants have no duty of disclosure thereof and to which Applicants are not bound) is activation of the HGF receptor, c-Met. Since the biological activity of HGF is mediated through phosphorylation of its receptor, c-met, the ability of compounds of the invention to phosphorylate c-met was tested.

a. Phosphorylation of c-met in Schwann cells. SF/HGF bioactivity is mediated via phosphorylation and activation of its receptor, c-Met. Schwann cells were purchased from ATCC, VA and incubated with SF/HGF (50 ng/ml) or inventive compounds at 10 uM concentration for one hour in serum-free medium. C-Met phosphorylation was determined by performing SDS PAGE followed by Western blotting using phosphor met antibody from Cell Signaling. As seen in FIG. 3, compounds of the invention induced robust phosphorylation of c-Met, indicating activation of the SF/HGF/c-Met pathways.

b. Phosphorylation of c-met in HUVECs and MDCK cells. HUVECs and MDCK cells were incubated with either HGF (80 ng) or instant compounds (10 uM) for 1 hr, followed by Western blot analysis. Compounds of the invention compounds phosphorylated c-Met in these cells.

c. Intracellular Signaling Induced by Compounds and HGF. To determine whether compound-mediated c-met phosphorylation induces the same intracellular signaling cascades as HGF, endothelial cells were stimulated with the instant compounds, and extracellular receptor kinase (ERK) phosphorylation was then assayed by Western blot analysis. Western blot analyses are then performed by probing for total ERK using antibodies that do not distinguish between the phosphorylated and non-phosphorylated forms; the membranes were then stripped and re-probed with antibodies that recognize only phosphorylated ERK. Unstimulated cells contain little phosphorylated ERK. Under identical cell culture conditions, however, instant compounds significantly increase the intracellular levels of phosphorylated ERK, while total ERK remains unaffected. These results are similar to phosphorylated ERK levels observed in the presence of HGF.

Figure 4:
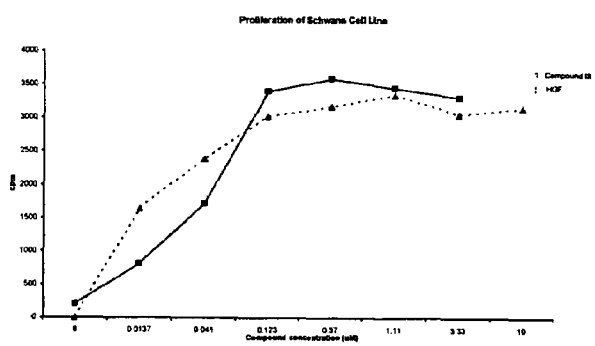
FIG. 4A-C show the a compound of the invention stimulates proliferation of Schwann cells (A) and PC12 neuronal cells (B), and stimulates myelin production by Schwann cells (C).
Figure 4:
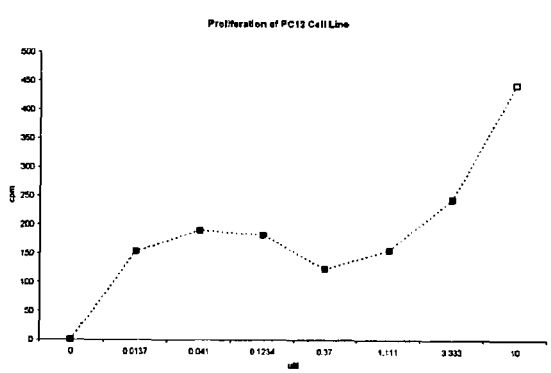
Figure 4:
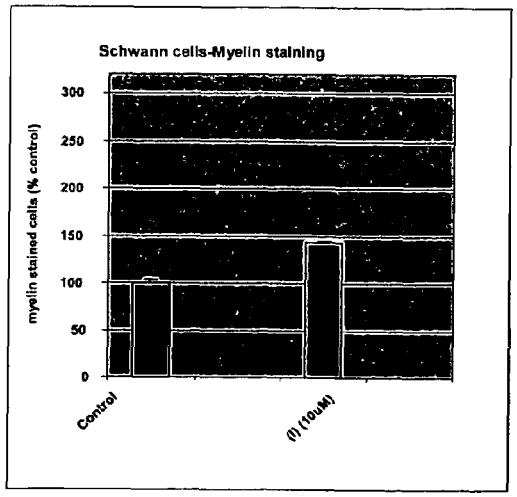
Figure 5:
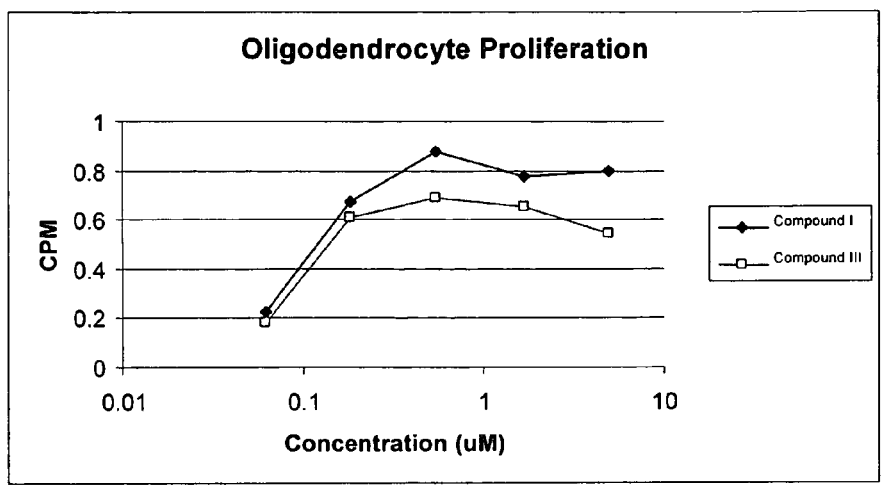
FIG. 5 shows oligodendrocyte proliferation is stimulated by two compounds of the invention.
Figure 6:
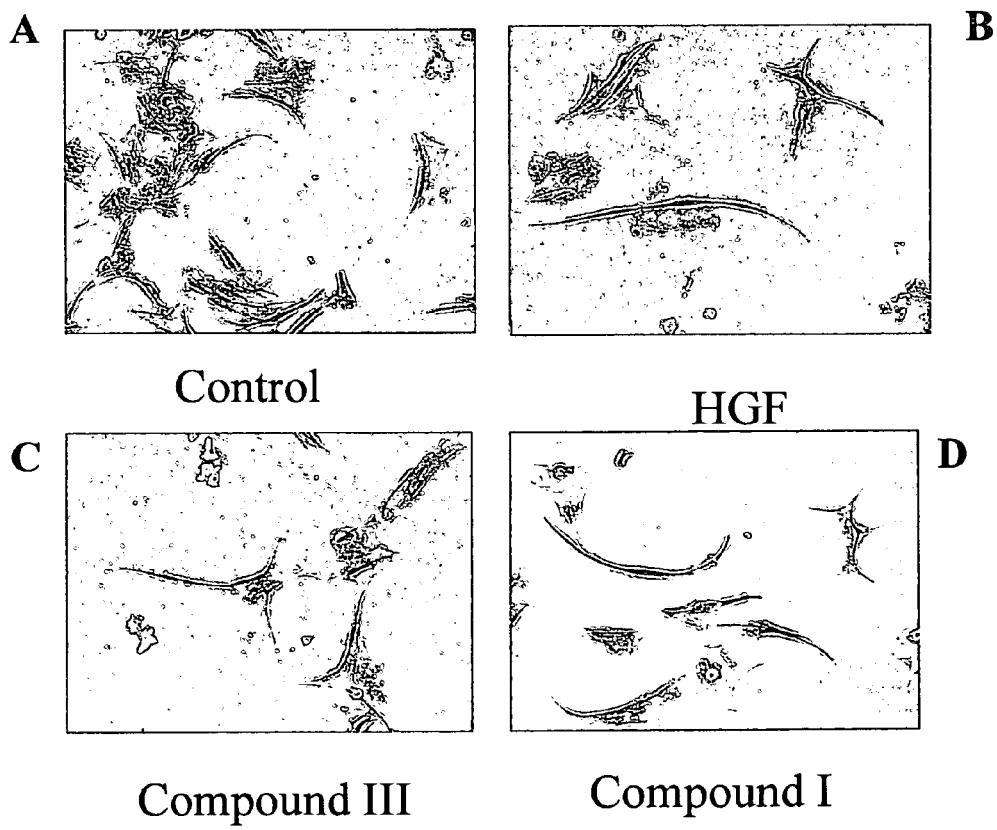
FIG. 6A-D show the effect of two compounds of the invention on axonal growth in vitro.

4. Schwann Cells, Neuronal Cells and Oligodendrocytes: Proliferation, Migration and Myelin Production a. Proliferation of Schwann Cells. Rat neuronal Schwann cells (RSC96 from ATCC) were seeded in 96-well plate ($10^4$ cell/well) in serum free medium for 16 hours. Cells were then treated with compound of the invention or HGF (positive control) at different concentrations for addition 16 hours. $^3$H-thymidine was added to the medium and incubation continued for another 4-5 hours. The cells were washed with PBS, harvested, and $^3$H-thymidine incorporation determined as a measure of proliferation. Compound of the invention stimulates [$^3$H]-thymidine incorporation, indicating stimulation of Schwann cell proliferation (FIG. 4A).

b. Proliferation of PC12 neuronal cells. In a similar assay to that described above, it was shown that inventive compound stimulated proliferation of PC12 cells, a neuronal cell type (FIG. 4B).

c. Migration of Schwann cells. In a cell migration assay (Boyden Chamber, BD Bioscience), 50000 Schwann cells were seeded in the inner chamber for 22 hours in the presence of 0.4% or 10% FBS, in the presence of compounds of invention. The cell number was quantified with 4.5 mg/ml Calcein following fluorescence reading. Compounds of the invention stimulated Schwann cell migration in this assay.

d. Myelin Production by Schwann Cells. Compounds of the invention induce myelin production by Schwann cells in vitro. Schwann cells at a density of 50,000 cells per well were seeded into 3-well chamber slides in serum-free medium for 24 hours. Test compounds (5 uM) or HGF/SF (50 ng/ml) were the added to the medium and the incubation continued for an additional 4 hours. Cells were washed and fluoromyelin (Molecular Probes) was added to each well. Images were obtained using a confocal microscope. Inventive compound induced over a three-fold increase in myelin production, similar to the extent of induction by HGF/SF (FIG. 4C).

e. Stimulation of Oligodendrocyte Proliferation. Mouse primary oligodendrocytes (Celprogen, Calif.) were seeded in 96-well plates at 5000 cells/well in serum-free medium for 16 hours. Cells were treated with test compound or HGF/SF (positive control) for 16-24 hours. WST1 cell proliferation reagent (Roche, N.J.) was added to oligodendrocytes, and incubation was continued for another 4-5 hours. Cells with WST1 reagent were read using a plate reader at an OD of 490 nm. Compounds and HGF/SF produced similar effects on cell proliferation (FIG. 5).

5. Axonal Growth.

Human HCN-2 neurons and Schwann cells were obtained from the American Type Culture Collection (Manassas, Va.). Cells were cultured in Dulbecco's modified Eagle's medium with 4 mM L-glutamine adjusted to contain 1.5 g/L sodium bicarbonate and 4.5 g/L glucose supplemented with 0.2 mg/ml G418 and 0.001 mg/ml puromycin, 90%, fetal bovine serum 10%. Cells are sub-cultured by removing media, rinsing with 0.25% trypsin, 0.03% EDTA solution followed by addition of fresh culture medium and plated onto poly-1-lysine coated culture flasks.

Human neurons (HCN-2) were seeded in 6 well plates (1000 cell/well) and incubated in 1% FBS with HGF/SF (50 ng/ml) or Compound of the invention (10 uM) over a 48 hour period. As shown in FIG. 6A-D, compounds of the invention promote axonal growth. In the presence of Schwann cells, the compounds stimulated axonal growth to a greater extent.

Figure 7:
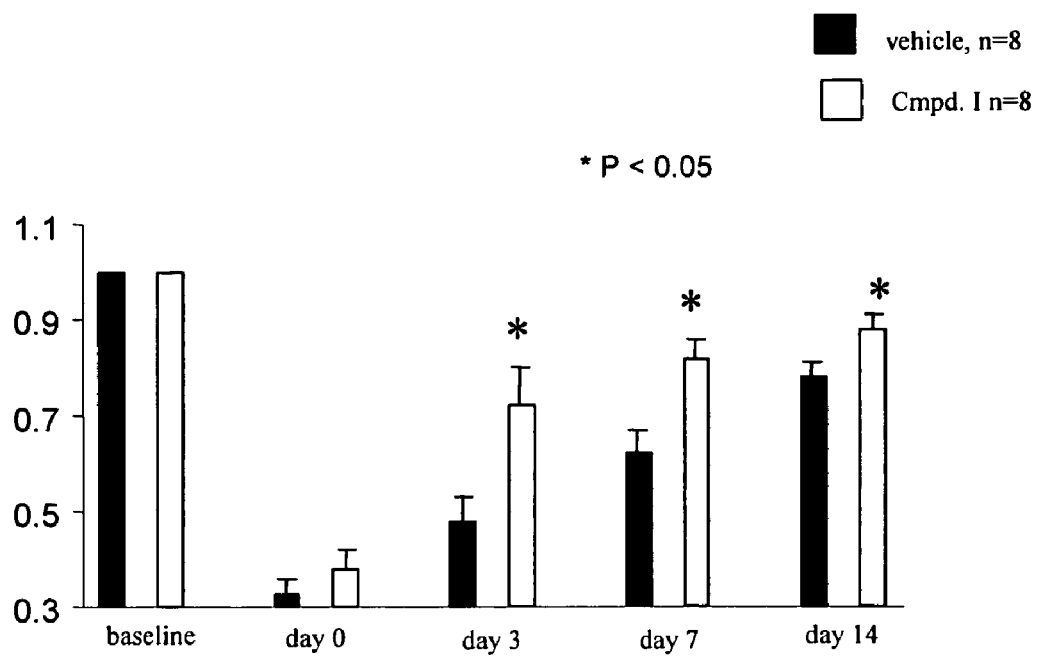
FIG. 7 shows that a compound of the invention increases affected limb blood flow in rats in a hindlimb ischemia model.

6. Peripheral Ischemia Model: Therapeutic Angiogenesis in Mouse and Rat Hindlimb Ischemia (Peripheral Vascular Insufficiency) Models.

a. Rats. To determine the time-dependent effects of inventive compounds in augmenting distal flow, male Sprague-Dawley rats (275-300 g) were subjected to left hindlimb ischemia and treated with vehicle or compound (2 mg/kg, i.p.) daily until sacrifice at day 14. Distal flow measurements using Laser Doppler scanning (Moor Instruments, Inc.) were obtained and normalized to pre-ischemic flow before and after the surgery. In the can, low power laser light is directed across the tissue surface in a raster pattern to construct a 2 dimensional image. Moving blood cells shift the frequency of incident light according to the Doppler principle. The backscattered light at the detectors causes constructive and destructive mixing of shifted light from moving blood and non-shifted light from static tissue. Intensity fluctuations are processed to give parameters of flux, which is proportional to tissue blood flow. Flux values of the areas of interest in the hindlimb are then compared between the left, ischemic hindlimb and the right, non-ischemic hindlimb and expressed as a fraction (ischemic/non-ischemic), with a value of 1 representing normal flow. As seen in FIG. 7, compared to the vehicle-treated group, compound-treated animals exhibited an enhanced recovery of blood flow.

7. Stroke Model.

Figure 8:
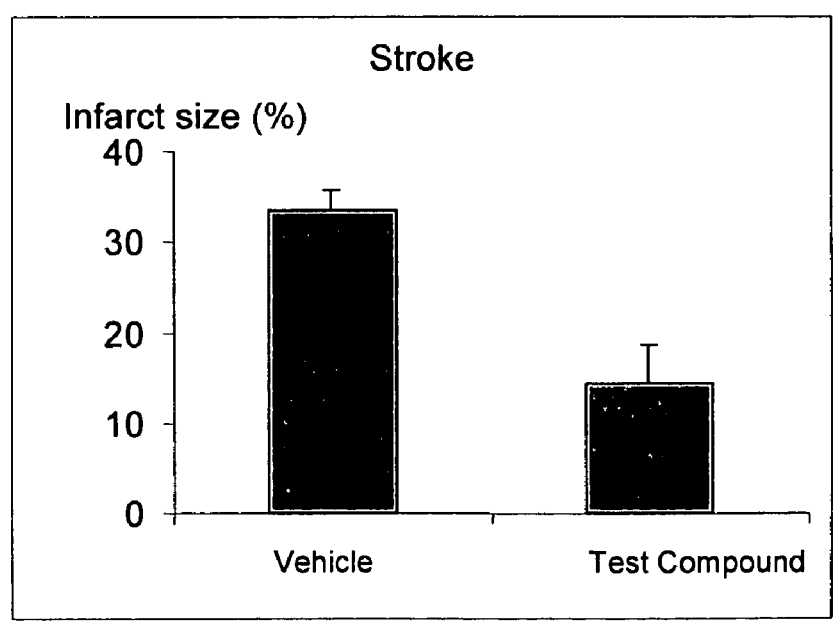
FIG. 8 shows that a compound of the invention administered to rats in which a stroke has been induced, reduces the infarct size.

Ischemia was induced in rats by middle cerebral artery occlusion (MCAO) for 24 hr. A compound of the invention, or placebo (saline), was administered i.v. at 2 mg/kg at 1-2, and 20 hr or in a delayed fashion at 4 hr and 20 hr post infarct induction. The extent of cerebral infarction was determined by staining brain sections with the mitochondrial activity indicator 2,3,5-triphenyltetrazolium chloride (TTC). As shown in FIG. 8, a large portion of the untreated rat brain displayed cerebral infarction, while inventive compound protects rats from such injury. In addition, the compound also increased blood flow in the injured area at day 7 and day 14 as detected by laser Doppler imaging, indicating that it promotes neovascularization following the injury.

8. Cardiovascular Disease Model.

a. Atherosclerosis: Immediate Treatment. Male apolipoprotein E (apoE)-deficient C57BL/6J mice were treated with a high fat diet for 16 weeks. Vehicle (n=15) or compound of the invention (2 mg/kg) (n=15) were administered daily, i.p. starting with the onset of high-fat diet. Animals were sacrificed (week 16) and atherosclerosis assays were performed on the aortic roots. Plaque formation was assessed in transverse aortic sections using H&E staining; Oil-Red-O staining was used to identify lipid deposits en face. Blood samples were collected at the time of death and analyzed for plasma cholesterol levels. ApoE deficient mice on regular chow diet served as normal controls.

Figure 9:
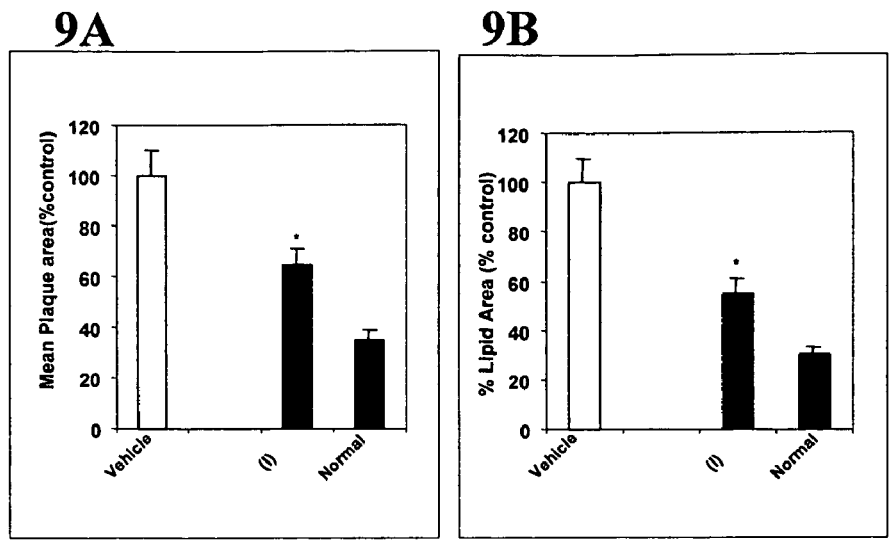
FIG. 9A-B show the reduction in plaque area in the arteries of ApoE knockout mice by a compound of the invention.
Figure 10:
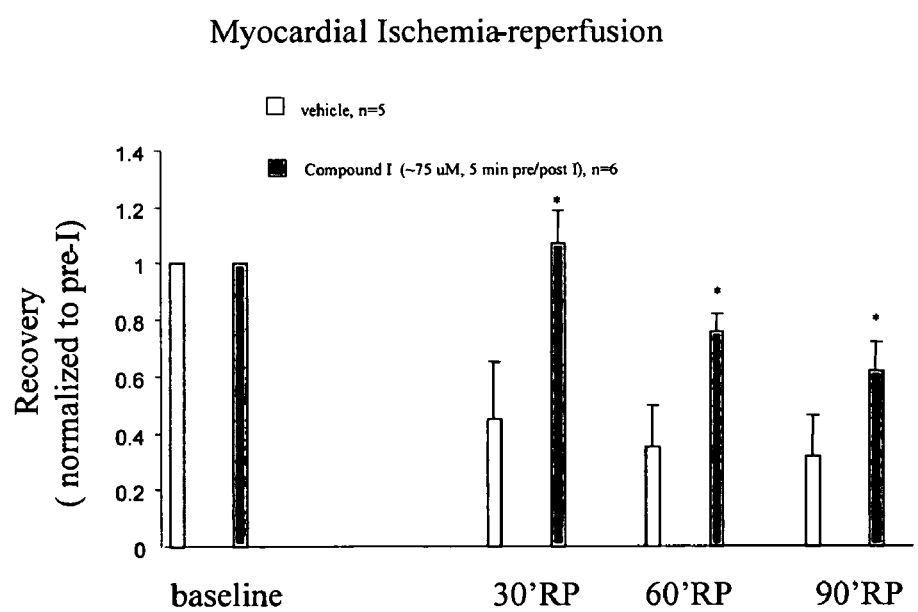
FIG. 10 shows that a compound of the invention improves cardiac function after ischemia-reperfusion in vitro.

At the time of sacrifice, there was no difference in plasma cholesterol levels (1200-1600 mg/dL) within the high-fat-treated groups. Treatment with a compound of the invention significantly reduced both plaque formation ($p<0.05$ vs. vehicle) and lipid deposits ($p<0.05$ vs. vehicle) in these high-fat treated mice (FIG. 9).

b. Delayed Treatment. In this series, mice were fed with high fat diet for 10 weeks. Diet was then switched to regular chow and animals were administered daily i.p injections of vehicle or compound of the invention (2 mg/kg) for 8 weeks. Blood and aortic sections were collected for analysis at the time of sacrifice (8 weeks into delayed treatment). There was no difference in the lipid profile between the vehicle and the compound-treated groups. Delayed treatment with inventive compound resulted in a significant decrease in both plaque formation and lipid deposition.

c. Myocardial Ischemia/Reperfusion. Hearts from male Sprague-Dawley rats were perfused in the Langendorrf Mode under constant pressure. Normothermic, isovolumic contracting hearts were subjected to 30 min global ischemia and 90 min reperfusion. Hearts were treated 5 min prior to ischemia and 5 min into reperfusion with vehicle or compound of the invention. As shown in FIG. 10, the product of left ventricular diastolic pressure and heart rate during reperfusion was normalized to pre-ischemic values.

Figure 11:
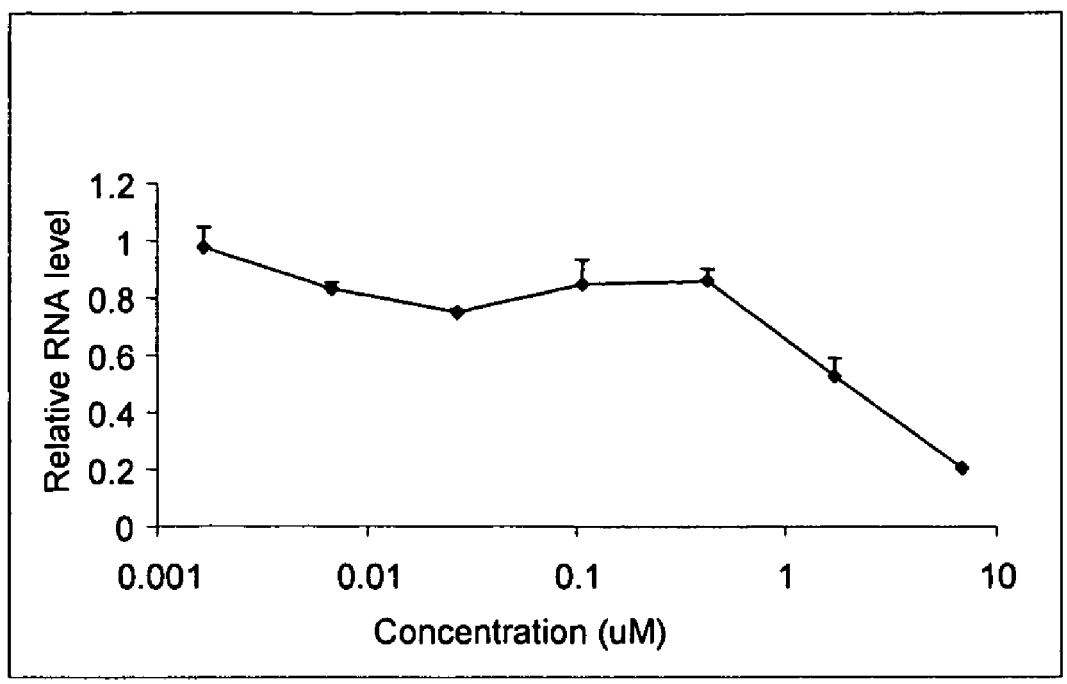
FIG. 11 shows the reduction in alpha-SMA RNA expression in TGFbeta1-induced renal fibrosis treated with a compound of the invention.
Figure 12:
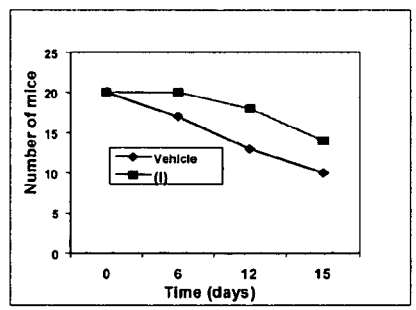
FIG. 12A-D show the effect of a compound of the invention on bleomycin-induced pulmonary fibrosis in mice, through survival (A), lung collagen-1 gene expression (B), lung collagen content measured by hydroxyproline (C), and fibrotic score (D).
Figure 12:
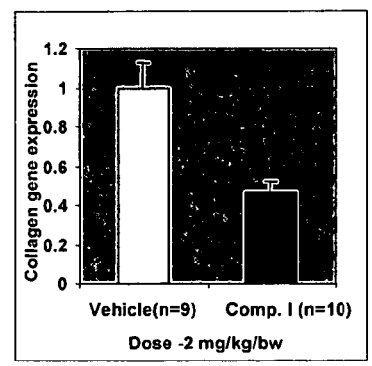
Figure 12:
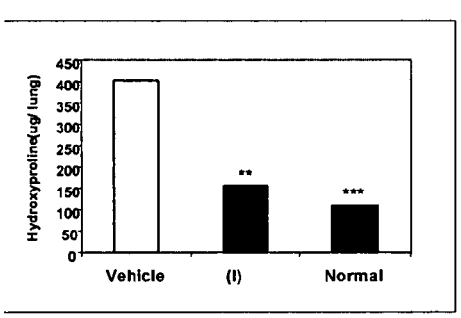
Figure 12:
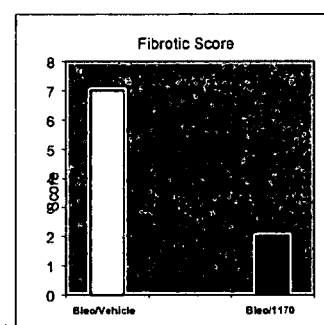

9. Fibrosis a. Anti-fibrotic Effects In Vitro: Initiation of a fibrotic cascade is crucial to atherosclerotic plaque formation. Consequently, anti-fibrotic therapies may find use against atherosclerotic plaque formation as well as in renal and pulmonary fibrotic diseases. The effects of a compound of the invention on TGFbeta1-induced alpha-smooth muscle actin (alpha SMA, fibrotic marker) expression in rat kidney fibroblasts was evaluated. Rat kidney fibroblasts cells (NRK-49F from ATCC) were activated by the treatment with TGFbeta1 at 2 ng/ml for 2 days. Compound of the invention was added and incubated for the same time period. Total cellular RNA was isolated and alpha smooth muscle actin (alphaSMA) mRNA was measured by reverse transcription-real time polymerase chain reaction (RT-PCR). AlphaSMA is upregulated during fibroblast activation and is a marker of fibrosis. The test compound inhibited the alphaSMA level, indicating that it has an anti-fibrotic potential (FIG. 11).

b. Anti-Fibrotic Effects In Vivo—Lung—Bleomycin Model: Fibrogenesis in different tissues shares common features and mechanisms including TGFbeta-stimulated pathological extracellular matrix build up. The activity of inventive compounds in other fibrosis models sheds light on an understanding in a fibrosis condition in atherosclerotic plaque regression. The anti-fibrotic activity of compounds of the invention was tested in a widely used model of pulmonary fibrosis, viz. bleomycin-induced pulmonary fibrosis. Briefly, C57BL/6 mice were anesthetized then administered intratracheally 100 µl of a solution containing bleomycin hydrochloride (Sigma; 0.1 U/20 gm body weight). Mice were then divided into vehicle or compound (2 mg/kg, i.p. daily)-treated groups. Survival in these mice was recorded. After two weeks, surviving mice were sacrificed and lungs harvested for determination of hydroxyproline, a key index of fibrosis. Treatment with inventive compound (I) to bleomycin-treated mice increased survival rate (FIG. 12A), decreased lung collagen expression as measured by RT-PCT (FIG. 12B), and decreased lung collagen content as measured in the hydroxyproline assay (FIG. 12C). Quantitation of histological analysis confirmed that treatment with inventive compound effectively prevented the fibrotic injury seen in bleomycin+vehicle-treated animals (FIG. 12D).

c. Anti-Fibrotic Effects In Vivo—Kidney—Doxorubicin Model. Doxorubicin administration results in progressive renal dysfunction and accumulation of interstitial collagen.

Figure 13:
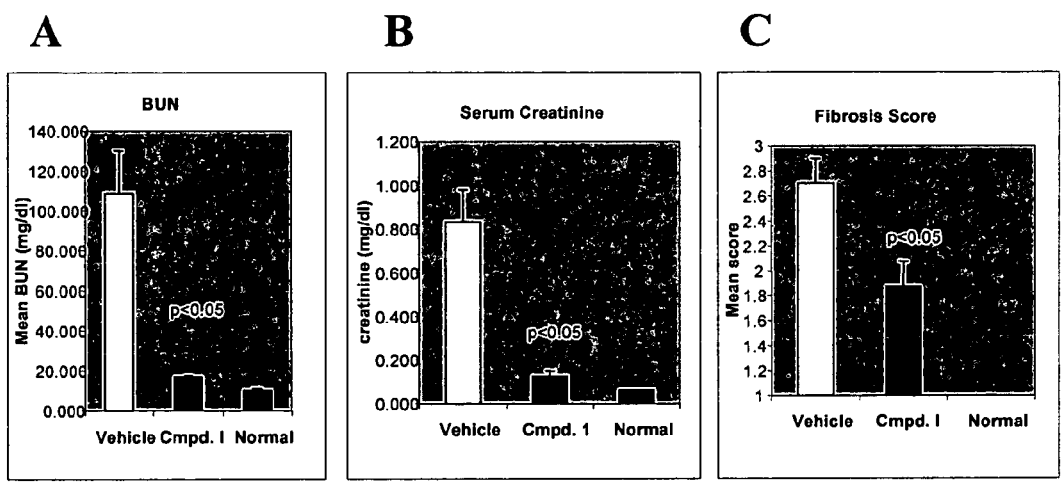
FIG. 13A-C shows the effects of a compound of the invention on renal fibrosis in a doxorubicin induction model, with regard to BUN (A), serum creatinine (B) and prefibrotic score (C).
Figure 14:
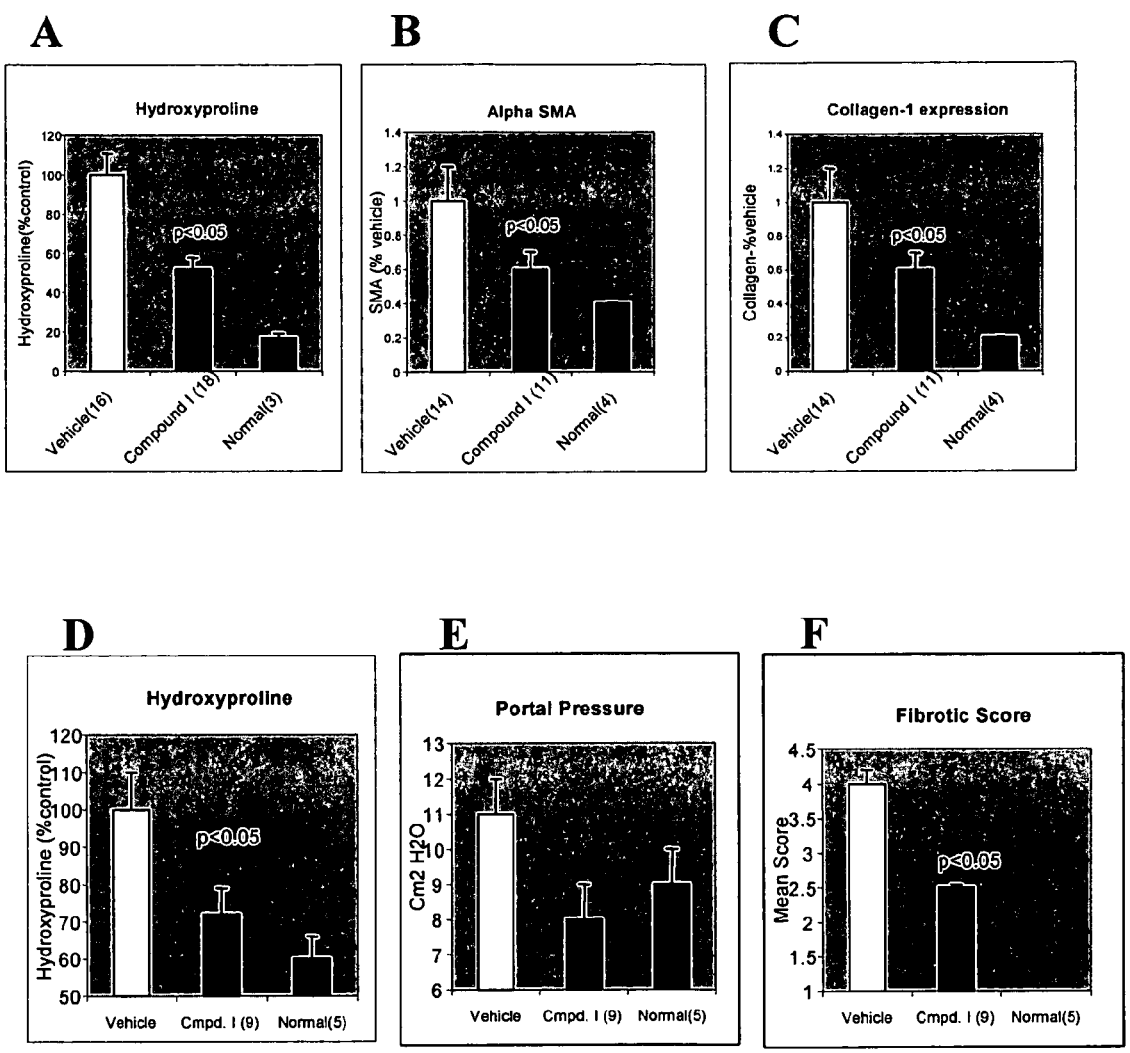
FIG. 14A-F show the effect of a compound of the invention on liver fibrosis induced by TAA.

This is a model for chronic renal failure and fibrosis. Male Sprague-Dawley rats (~300 g) were administered doxorubicin (10 mg/kg, iv). Starting twenty-four hours later, animals were treated daily with vehicle or a compound of the invention (2 mg/kg, i.p., n=8/group). Three weeks later animals were sacrificed for evaluation of renal function and histopathology. As seen in FIG. 13, treatment compound attenuates the renal dysfunction observed in the vehicle-treated cohort as measured by BUN (FIG. 13A), serum creatinine (FIG. 13B) and fibrotic score (FIG. 13C). Furthermore, interstitial collagen accumulation (Masson's trichrome stain) was reduced.

d. Anti-fibrotic effects: liver. Since fibrogenesis in different tissues shares common features and mechanisms including TGFbeta1-stimulated pathological extracellular matrix build up, compounds of the invention have been examined in the thioacetamide (TAA) induced liver fibrosis model. Sprague Dawley rats were treated with TAA at 200 mg/kg, i.p., three times a week for 8 weeks to induce liver fibrosis. At the time of TAA treatment, rats were also treated with compound of the invention via i.p route at 2 mg/kg body weight or vehicle (PEG300), daily, five times a week for 4 weeks, followed by sacrifice. In the co-treatment group, a panel of fibrotic markers was measured including collagen content (hydroproxyproline, FIG. 14A), and alpha SMA (FIG. 14B) and collagen-1 gene expression (RT-PCR; FIG. 14C).

In a separate group of rats, compound (25 mg/kg) was administered orally, with treatment onset delayed by 8 weeks following TAA onset. Hydroxyproline, portal pressure, and fibrotic score were measured to examine the oral efficacy of inventive compound in reducing liver fibrosis by hydroxyproline content (FIG. 14D), portal pressure (FIG. 14E) and fibrotic score (FIG. 14F). A fibrotic score of 4 indicates severe fibrosis while a score of 0 indicates no fibrosis.

10. Renal Ischemia.

a. In a mouse model of transient unilateral renal artery occlusion, male ICR mice are anesthetized and the left renal artery occluded with a microvascular clamp. After 30 minutes, the clamp is removed and the kidney allowed to reperfuse. Ten minutes into reperfusion the nonischemic contralateral kidney is excised. Animals are treated daily with vehicle or compound of the invention (2 mg/kg, i.p.) until the day of sacrifice. Serum creatinine, BUN and urine protein levels, measured at 1, 4 and 7 days post-ischemia are used to determine the ability of compounds of the invention to restore function to injured kidneys. In order to create a more severe renal injury, animals are subjected to 45 minutes of ischemia.

b. Protection against $HgCl_2$-induced renal injury. In a study mice are injected with a high dose of $HgCl_2$ (7 mg/kg, s.c.) and divided into treatment groups. Animals in the first group receive vehicle or a compound of the invention (2 mg/kg, i.p.) on the day of toxin injection and daily thereafter for 3 days, and are euthanized on day 4. Blood samples collected prior to $HgCl_2$ injection, on day 2 and on day 4 are analyzed for serum creatinine. In the second group, treatment with vehicle or compound begins on the day following toxin injection (i.e., 24 h delayed treatment) and daily thereafter until day 6. Mice are euthanized on day 7. Blood samples collected prior to $HgCl_2$ injection, on day 4 and day 7 are analyzed for serum creatinine and BUN. Serum creatinine, BUN, and development of tubular necrosis are measured to indicate positive clinical activity.

c. Protection against ureteral obstruction. The effects of the compounds of invention on renal injury secondary to ureteral obstruction are examined in a mouse model of transient unilateral renal artery occlusion. Kidneys from mice subjected to unilateral ureteral obstruction for 2 weeks are examined for histological evidence of injury and protection by compound treatment. Immunohistochemical staining is performed for fibronectin, proliferating cell nuclear antigen, and TUNEL (for an assessment of apoptosis). Trichrome staining is also performed to assess the extent of collagen formation as an indication of interstitial fibrosis.

11. Diabetes.

Figure 15:
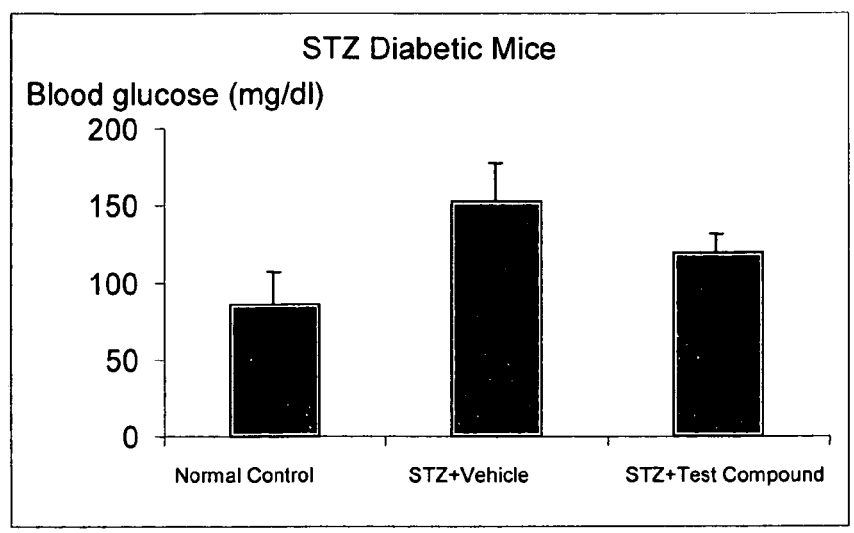
FIG. 15 shows that a compound of the invention reduces hyperglycemia in streptozotocin-treated (diabetic) mice.

Normal CD-1 mice were injected i.p. once with 100 mg/kg streptozotocin (STZ) and then treated with a compound of the invention at 2 mg/kg i.p. daily for seven days. At day 7, blood samples were harvested and blood glucose determined. STZ treatment resulted in hyperglycemia (high blood glucose). Treatment with compound of the invention treatment ameliorated the hyperglycemia in the diabetic mice (FIG. 15).

Figure 16:
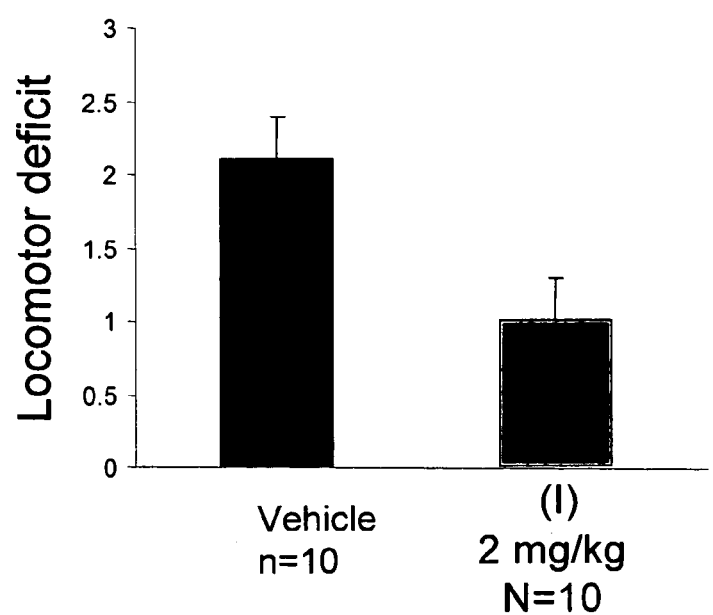
FIG. 16 shows that a compound of the invention improves the locomotor deficit induced in mice in the EAE multiple sclerosis model.

12. Mouse model of multiple sclerosis. EAE was induced by immunization of male C57 BL6 mice with 200 μg MOG 35-55 emulsified in complete Freund's adjuvant (CFA) containing 5 mg/ml M. tuberculosis (Difco, Mich.) on days 0 and 7 subcutaneously in the hind flank as described by Ford, M. L. and B. D. Evavold, Specificity, magnitude, and kinetics of MOG-specific CD8+ T cell responses during experimental autoimmune encephalomyelitis. Eur. J. Immunol 35, 76-85, 2005. Compound of the invention (2 mg/kg) or vehicle was administered i.p., daily for 3 weeks. Compound and vehicle administration started on day 7, immediately after the second injection of MOG 35-55. At the end of the 3-week treatment period, disease severity with respect to locomotor deficit was monitored in the blind scoring by two scientists according to the following scale: 0, no disease; 1, flaccid tail; 2, hind limb weakness; 3, hind limb paralysis; 4, forelimb weakness; 5, moribund. As shown in FIG. 16, the test compound reduced locomotor deficit.

Figure 17:
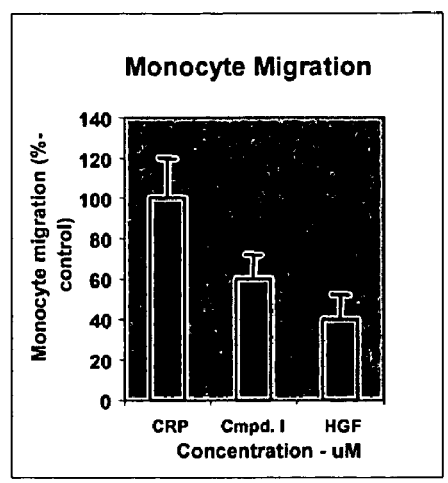
FIG. 17 shows that a compound of the invention decreases migration of monocytes.

13. Inventive Compounds Decrease Monocytes Migration.

a. Compound treatment decreases monocyte migration and binding to ECs. Elevated CRP has been shown to exert pro-atherogenic effects on vascular cells exemplified by increasing the secretion of monocyte chemoattractant protein (MCP-1) and reducing nitric oxide bioactivity, and induce adhesion molecules, such as vascular cell adhesion molecule-1 (VCAM-1), and increase monocyte binding/migration to endothelial cells. HUVECs were incubated with CRP (25 ug/ml), CRP together with test compound (10 uM) or HGF (50 ng/ml). The cellular extracts with lysis buffer and analyzed for VCAM-1 and MCP-1 expression via Western blot analysis. For Monocyte binding and migration experiments, monocytes were labeled with a fluorescent dye Vybrant Did (Molecular Probes) and treated to the HUVECs treated as above. Monocyte migration and binding to ECs decreased with test compound treatment as shown in FIG. 17. Test compound and HGF treatment also decreased VCAM-1 expression and MCP-1 expression and decreased monocyte migration and binding to endothelial cells.

14. Compound-mediated therapeutic angiogenesis. Compounds of the invention induce angiogenesis in vivo, providing clear evidence that compounds can at least mediate HGF-like biologic activity by inducing c-met phosphorylation and activating specific intracellular signaling cascades. To test whether this activity can be used to therapeutic advantage, the ability of compounds to induce blood vessel growth was tested in vivo. In this assay compounds or vehicle (control, RPMI media+1% BSA) was mixed with Matrigel, a matrix of reconstituted basement membrane. Samples were injected subcutaneously into mice. After 10 days, mice were sacrificed for histologic and morphometric analysis of Matrigel plugs. Plugs containing compound show a greater density of cells. These results are similar to above studies that demonstrated that HGF dose-dependently increases the vessel area in this in vivo assay. Such findings are also applicable to other cytokines and the observations are generally applicable to other cytokines such as but not limited to those described above.

What is claimed is:

1. An isolated compound having the structure:

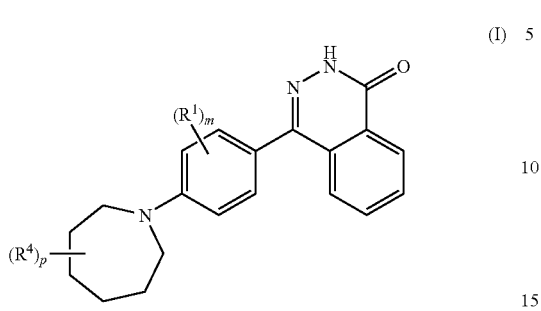

or pharmaceutically acceptable salt, ester, or salt of such an ester thereof;

wherein m is an integer from 1 to 4;

p is an integer from 1 to 6;

each occurrence of $R^1$ and $R^4$ is independently hydrogen, halogen, hydroxyl, —$NO_2$, —$NH_2$, —CN, —$CONH_2$, —$SO_2OH$, an optionally substituted aliphatic, alicyclic, heteroaliphatic, heterocyclic, aromatic or heteroaromatic moiety, —$OR^R$, —$S(=O)_nR^d$, —$NR^bR^c$, —C(=O)$R^a$, —$OPO_2OR^a$ or —C(=O)$OR^a$; wherein n is 0-2, $R^R$ is an optionally substituted aliphatic, alicyclic, heteroaliphatic, heterocyclic, aromatic, heteroaromatic or acyl moiety;

$R^a$, for each occurrence, is independently selected from the group consisting of hydrogen and an optionally substituted aliphatic, alicyclic, heteroaliphatic, heterocyclic, aromatic, or heteroaromatic moiety;

$R^b$ and $R^c$, for each occurrence, are independently selected from the group consisting of hydrogen; hydroxy; $SO_2R^d$; and aliphatic, alicyclic, heteroaliphatic, heterocyclic, aromatic, heteroaromatic or acyl moiety;

$R^d$, for each occurrence, is independently selected from the group consisting of hydrogen; —N($R^e$)$_2$; aliphatic, alicyclic, heteroaliphatic, heterocyclic, aromatic or heteroaromatic; and $R^e$, for each occurrence, is independently hydrogen or aliphatic.

2. The compound of claim 1, wherein:

m is an integer from 1 to 4;

p is an integer from 1 to 6;

each occurrence of $R^1$ and $R^4$ is independently hydrogen, halogen, hydroxyl, —$NO_2$, —$NH_2$, —CN, an optionally substituted alkyl, heteroalkyl, cycloalkyl, heterocyclic, aryl or heteroaryl moiety, —$OR^R$, —$S(=O)_nR^d$, —$NR^bR^c$, —C(=O)$R^a$, —$OPO_2OR^a$ or —C(=O)$OR^a$; wherein n is 0-2, $R^R$ is an optionally substituted alkyl, heteroalkyl, cycloalkyl, heterocyclic, aryl, heteroaryl or acyl moiety;

$R^a$, for each occurrence, is independently hydrogen or an optionally substituted alkyl, heteroalkyl, cycloalkyl, heterocyclic, aryl or heteroaryl moiety;

$R^b$ and $R^c$, for each occurrence, are independently hydrogen hydroxy, $SO_2R^d$, or an alkyl, heteroalkyl, cycloalkyl, heterocyclic, aryl, heteroaryl or acyl moiety;

$R^d$, for each occurrence, is independently hydrogen, —N($R^e$)$_2$, alkyl, heteroalkyl, cycloalkyl, heterocyclic, aryl or heteroaryl; and $R^e$, for each occurrence, is independently hydrogen or alkyl.

3. The compound of claim 2 having the structure:

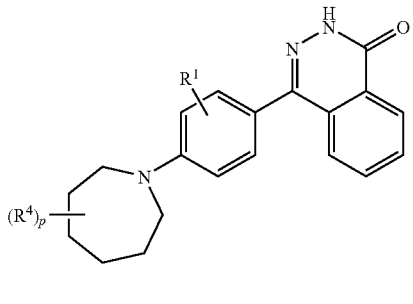

wherein p, $R^1$ and $R^4$ are as defined in claim 2.

4. The compound of claim 2 having the structure:

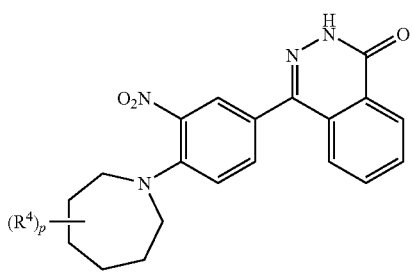

wherein p and $R^4$ are as defined in claim 2.

5. The compound of claim 2 having the structure:

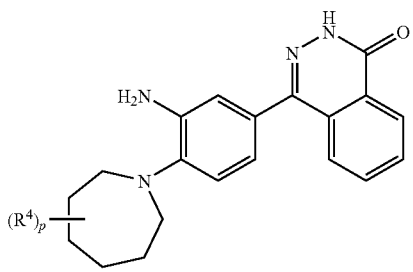

wherein p and $R^4$ are as defined in claim 2.

6. The compound of claim 2 having the structure:

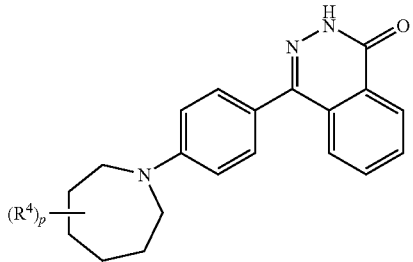

wherein p and $R^4$ are as defined in claim 2.

7. The compound of claim 2 having the structure:

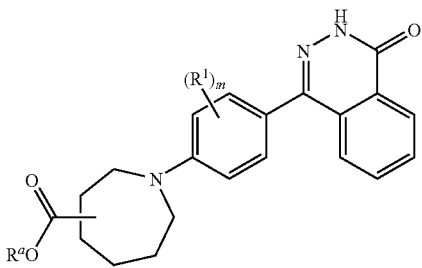

wherein m, $R^1$ and $R^a$ are as defined in claim 2.

8. The compound of claim 2 having the structure:

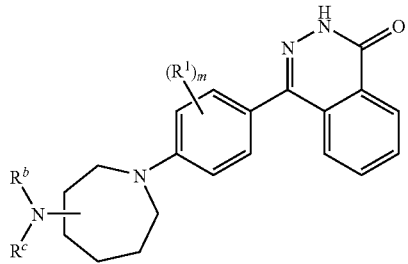

wherein m, $R^1$, $R^b$ and $R^c$ are as defined in claim 2.

9. The compound of claim 1, wherein at least one occurrence of $R^1$ is —$NO_2$.

10. The compound of claim 1, wherein at least one occurrence of $R^1$ is —$NH_2$.

11. The compound of claim 1, wherein at least one occurrence of $R^1$ is —COOH, —C(=O)$OCH_3$, —$COCH_3$, —$CONH_2$, —$SO_2OH$, —$SO_2CH_3$, —$SO_2CF_3$, —$OPO_2OH$, —NHC(=O)$CH_3$, —NHC(=O)$CF_3$, —$NHSO_2CH_3$ or —$NHSO_2CF_3$.

12. The compound of claim 1, wherein at least one occurrence of $R^1$ is halogen.

13. The compound of claim 1, wherein at least one occurrence of $R^1$ is an optionally substituted N-linked heterocyclic group.

14. The compound of claim 13, wherein the N-linked heterocyclic group is an optionally substituted N-pyrrolyl.

15. The compound of claim 1, wherein at least one occurrence of $R^1$ is an aliphatic moiety.

16. The compound of claim 1, wherein at least one occurrence of $R^1$ is a lower alkyl moiety.

17. The compound of claim 1, wherein at least one occurrence of $R^4$ is an aliphatic group.

18. The compound of claim 1, wherein each occurrence of $R^4$ is independently an aliphatic group.

19. The compound of claim 18, wherein the aliphatic group is an optionally substituted cyclic or acyclic $C_{6-12}$alkyl, $C_{6-12}$alkenyl, or $C_{6-12}$alkynyl group.

20. The compound of claim 18, wherein $R^4$ an optionally substituted -(alkyl)aryl group.

21. The compound of claim 1, wherein at least one occurrence of $R^4$ is —$NR^bR^c$; wherein $R^b$ and $R^c$ are independently hydrogen, hydroxy, $SO_2R^d$, or an alkyl, heteroalkyl, cycloalkyl, heterocyclic, aryl, heteroaryl or acyl moiety; $R^d$ is hydrogen, —$N(R^e)_2$, alkyl, heteroalkyl, cycloalkyl, heterocyclic, aryl or heteroaryl; and $R^e$ is hydrogen or alkyl.

22. The compound of claim 1, wherein at least one occurrence of $R^4$ is —$NH_2$.

23. The compound of claim 1, wherein at least one occurrence of $R^4$ is —C(=O)$OR^a$; wherein $R^a$ is hydrogen or an optionally substituted alkyl, heteroalkyl, cycloalkyl, heterocyclic, aryl or heteroaryl moiety.

24. The compound of claim 1, wherein at least one occurrence of $R^4$ is —$CO_2H$.

25. The compound of claim 1, wherein m is 0 or 1.

26. The compound of claim 1, wherein p is 0 or 1.

27. The compound of claim 1 having one of the following structures:

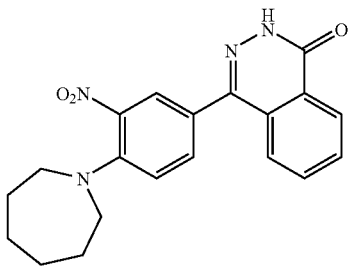

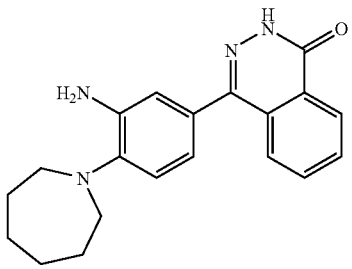

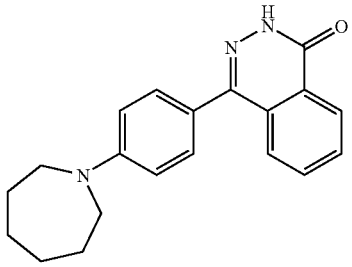

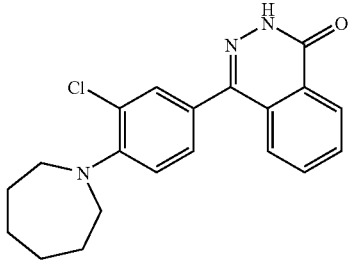

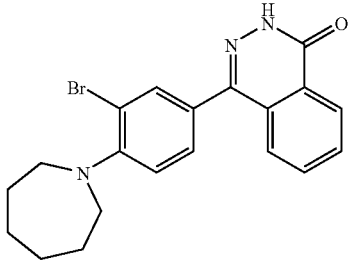

-continued
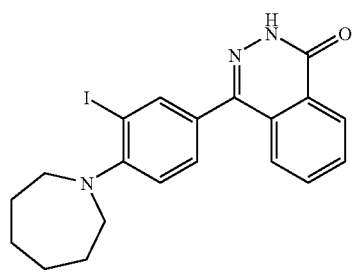
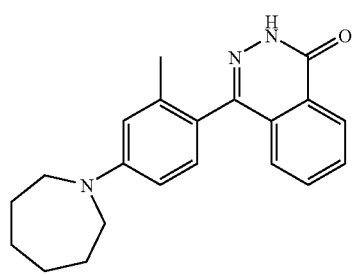
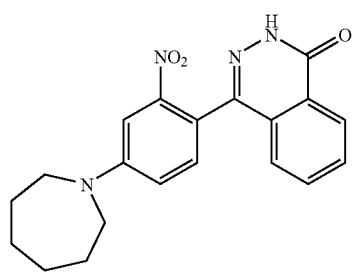
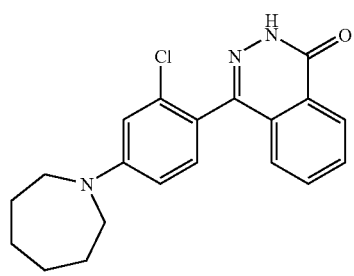
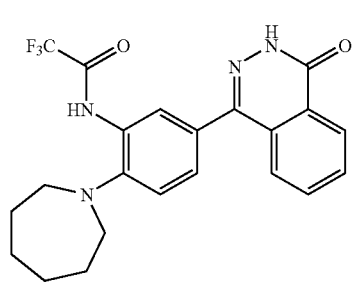
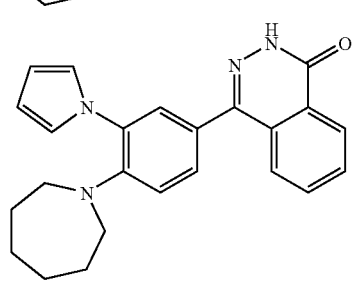
-continued
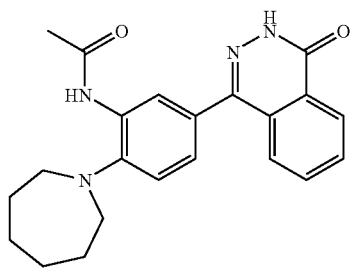
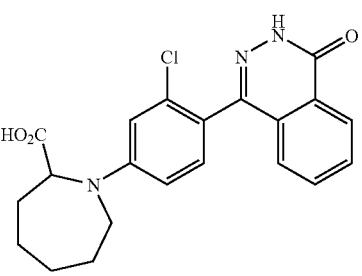
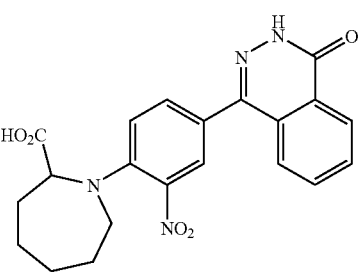
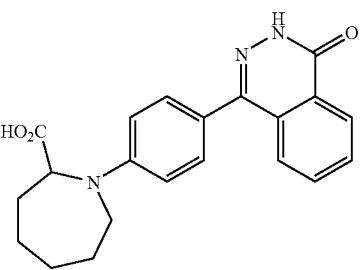
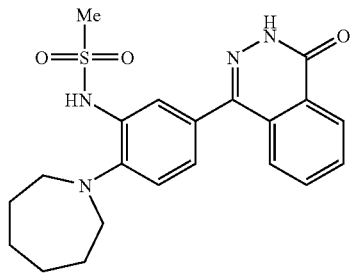
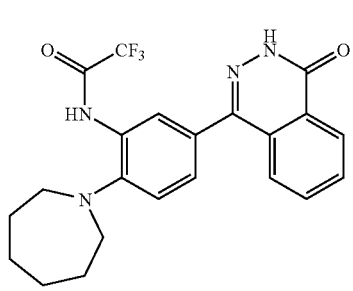

-continued

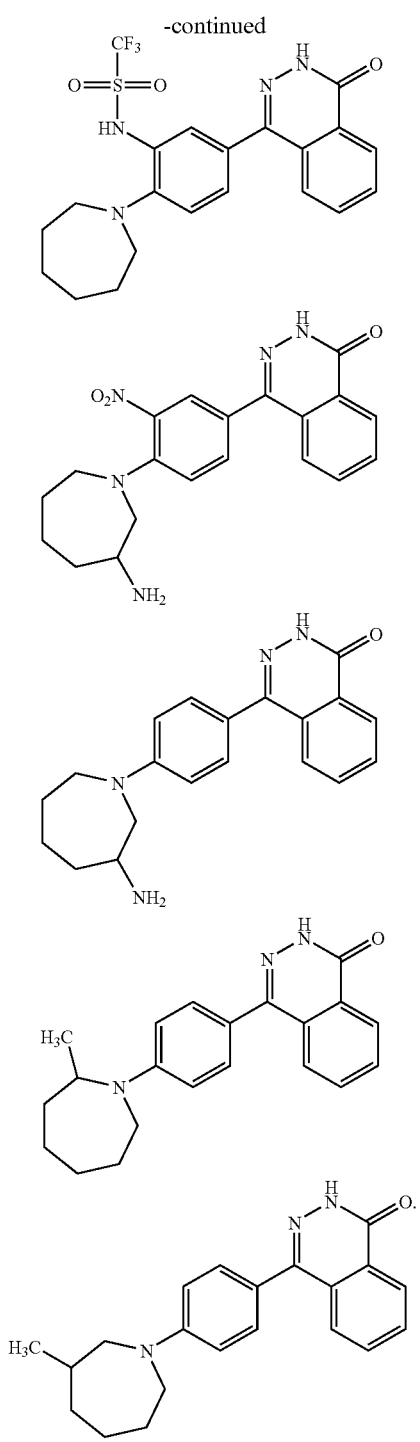

28. A pharmaceutical composition comprising:
a pharmaceutically acceptable carrier, adjuvant or vehicle; and
a compound of claim 1.

29. A method for treating or lessening the severity of fibrotic liver disease, hepatic ischemia-reperfusion injury, cerebral infarction, ischemic heart disease, renal disease or lung (pulmonary) fibrosis, multiple sclerosis, metachromatic leukodystrophy, Refsum's disease, adrenoleukodystrophy, Krabbe's disease, phenylketonuria, Canavan disease, Pelizaeus-Merzbacher disease, or Alexander's disease in a subject comprising administering to a subject in need thereof, optionally with a pharmaceutically acceptable carrier, adjuvant or vehicle, a therapeutically effective amount of a compound according to claim 1.

30. The method of claim 29 wherein the method is for treating or lessening the severity of a disease or condition selected from liver fibrosis associated with hepatitis C, hepatitis B, delta hepatitis, chronic alcoholism, non-alcoholic steatohepatitis, extrahepatic obstructions (stones in the bile duct), cholangiopathies (primary biliary cirrhosis and sclerosing cholangitis), autoimmune liver disease, and inherited metabolic disorders (Wilson's disease, hemochromatosis, and alpha-1 antitrypsin deficiency); damaged and/or ischemic organs, transplants or grafts; ischemia/reperfusion injury; stroke, traumatic head injury, spinal cord injury, and other cerebrovascular diseases; myocardial ischemia; atherosclerosis; peripheral vascular disease; diabetes; renal failure; renal fibrosis, lung fibrosis or idiopathic pulmonary fibrosis; and multiple sclerosis.

31. The method of claim 29 wherein the method is for the treatment of wounds for acceleration of healing; promoting vascularization of a damaged and/or ischemic organ, transplant or graft; amelioration of isehemia/reperfusion injury in the brain, heart, liver, kidney, or other tissues or organs; normalization of myocardial perfusion as a consequence of chronic cardiac ischemia or myocardial infarction; development or augmentation of collateral vessel development after vascular occlusion or to ischemic tissues or organs; fibrotic diseases; hepatic disease including fibrosis and cirrhosis; lung fibrosis; radiocontrast nephropathy; fibrosis secondary to renal obstruction; renal trauma and transplantation; renal failure secondary to chronic diabetes and/or hypertension; and/or diabetes mellitus.

32. The method of claim 29 wherein the compound has one of the following structures:

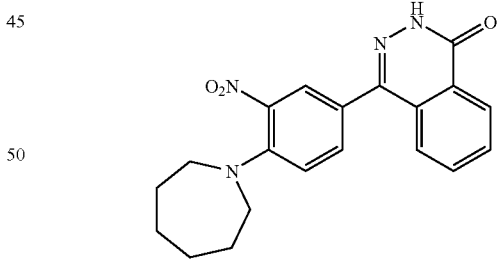

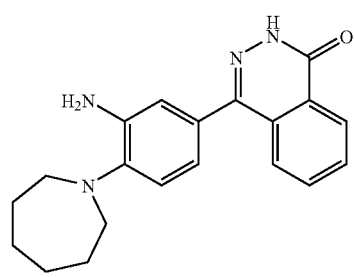

-continued
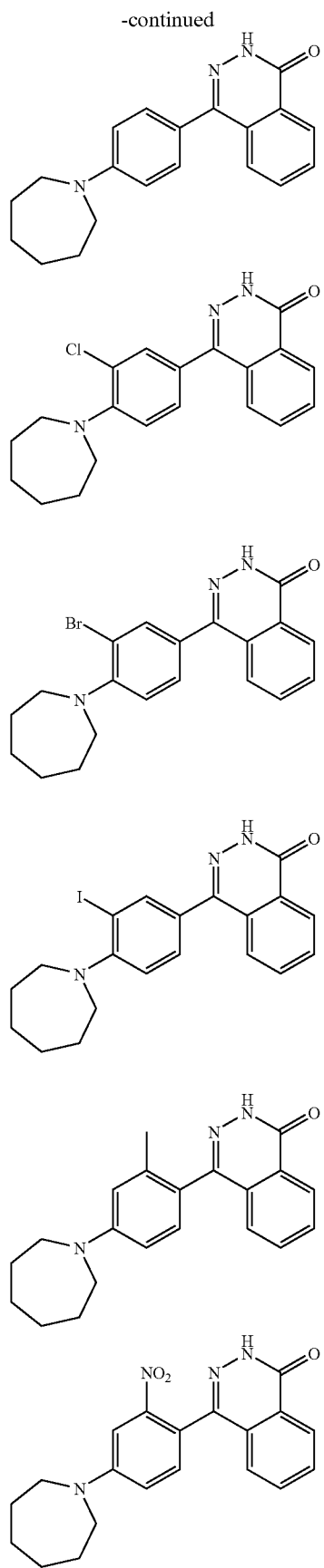
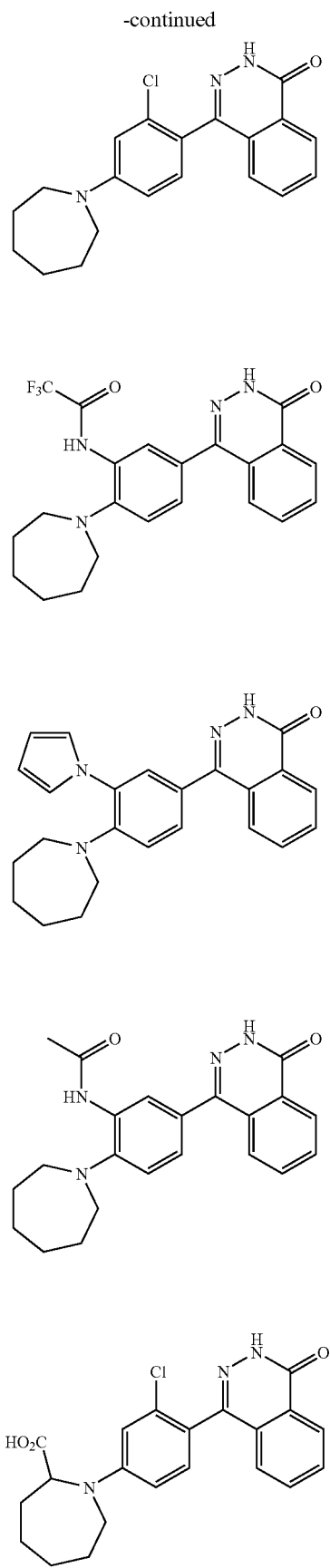

-continued
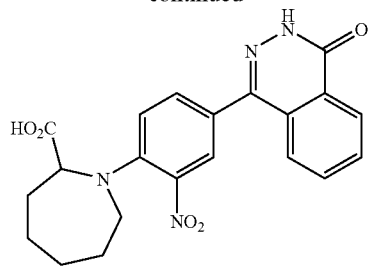
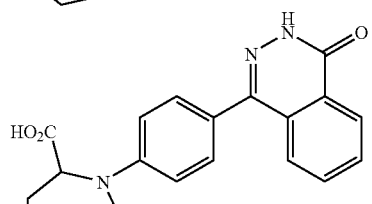
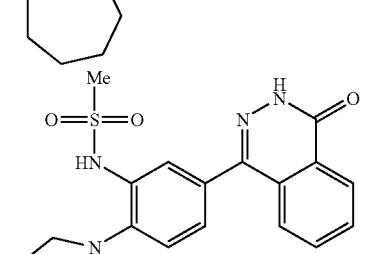
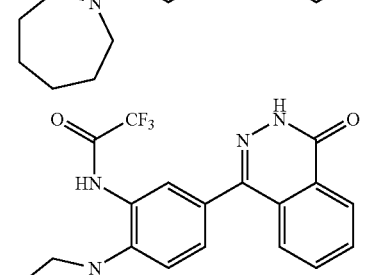
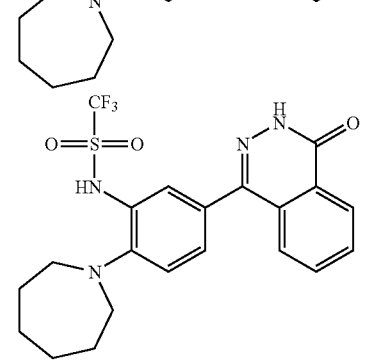
-continued
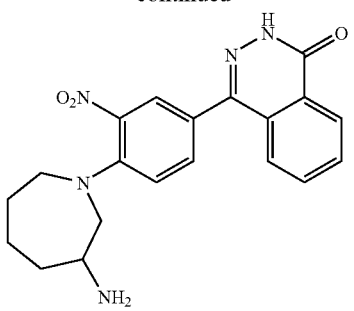
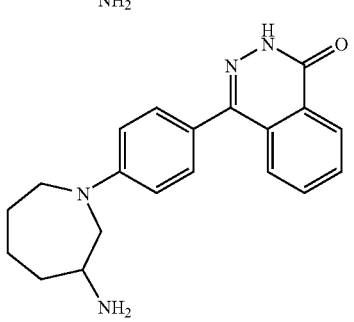
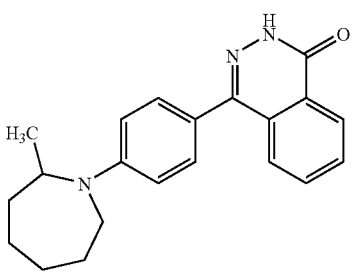
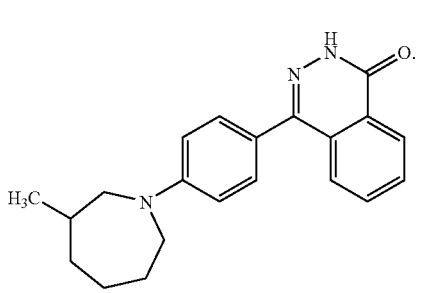
* * * * *

UNITED STATES PATENT AND TRADEMARK OFFICE
CERTIFICATE OF CORRECTION

PATENT NO. : 7,648,978 B2 Page 1 of 1
APPLICATION NO. : 11/238285
DATED : January 19, 2010
INVENTOR(S) : Zembower et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,648,978 B2  
APPLICATION NO. : 11/238285  
DATED : January 19, 2010  
INVENTOR(S) : Zembower et al.

It is certified that error appears in the above-identified patent and that said Letters Patent is hereby corrected as shown below:

Specification

In Column 1, replace lines 10-15 with the following:

-- GOVERNMENT SUPPORT

This invention was made with U.S. government support under Grant no. CA096077 awarded by the National Institutes of Health. The U.S. government has certain rights in the invention. --

Signed and Sealed this  
Fifth Day of January, 2016

Michelle K. Lee  
*Director of the United States Patent and Trademark Office*